(12) United States Patent
Sah et al.

(10) Patent No.: US 11,193,129 B2
(45) Date of Patent: Dec. 7, 2021

(54) MODULATORY POLYNUCLEOTIDES

(71) Applicant: VOYAGER THERAPEUTICS, INC., Cambridge, MA (US)

(72) Inventors: Dinah Wen-Yee Sah, Cambridge, MA (US); Jinzhao Hou, Cambridge, MA (US); Mathieu E. Nonnenmacher, Cambridge, MA (US)

(73) Assignee: VOYAGER THERAPEUTICS, INC., Cambridge, MA (US)

( * ) Notice: Subject to any disclaimer, the term of this patent is extended or adjusted under 35 U.S.C. 154(b) by 11 days.

(21) Appl. No.: 16/749,293

(22) Filed: Jan. 22, 2020

(65) Prior Publication Data
US 2020/0149045 A1 May 14, 2020

Related U.S. Application Data

(63) Continuation of application No. 16/302,146, filed as application No. PCT/US2017/033268 on May 18, 2017, now Pat. No. 10,584,337.

(60) Provisional application No. 62/338,137, filed on May 18, 2016, provisional application No. 62/485,050, filed on Apr. 13, 2017.

(51) Int. Cl.
| | | |
|---|---|---|
| *C12N 15/113* | (2010.01) | |
| *C12N 15/11* | (2006.01) | |
| *C12N 15/85* | (2006.01) | |

(52) U.S. Cl.
CPC .......... *C12N 15/113* (2013.01); *C12N 15/111* (2013.01); *C12N 15/85* (2013.01); *C12N 2310/14* (2013.01); *C12N 2310/141* (2013.01); *C12N 2310/3519* (2013.01); *C12N 2310/531* (2013.01); *C12N 2310/533* (2013.01); *C12N 2320/52* (2013.01); *C12N 2750/14143* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 5,064,764 A | 11/1991 | Besnainon | |
| 5,474,935 A | 12/1995 | Chatterjee | |
| 5,587,308 A | 12/1996 | Carter | |
| 5,652,224 A | 7/1997 | Wilson | |
| 5,658,785 A | 8/1997 | Johnson | |
| 5,688,676 A | 11/1997 | Zhou | |
| 5,691,176 A | 11/1997 | Lebkowski | |
| 5,693,531 A | 12/1997 | Chiorini | |
| 5,741,683 A | 4/1998 | Zhou | |
| 5,756,283 A | 5/1998 | Wilson | |
| 5,856,152 A | 1/1999 | Wilson | |
| 5,858,351 A | 1/1999 | Podsakoff | |
| 5,858,775 A | 1/1999 | Johnson | |
| 5,866,552 A | 2/1999 | Wilson | |
| 5,866,696 A | 2/1999 | Carter | |
| 5,871,982 A | 2/1999 | Wilson | |
| 5,952,221 A | 9/1999 | Kurtzman | |
| 5,962,313 A | 10/1999 | Podsakoff | |
| 5,989,540 A | 11/1999 | Carter | |
| 6,083,716 A | 7/2000 | Wilson | |
| 6,143,548 A | 11/2000 | ORiordan | |
| 6,143,567 A | 11/2000 | Van Agthoven | |
| 6,146,874 A | 11/2000 | Zolotukhin | |
| 6,156,303 A | 12/2000 | Russell | |
| 6,174,527 B1 | 1/2001 | Wilson | |
| 6,180,613 B1 | 1/2001 | Kaplitt | |
| 6,194,191 B1 | 2/2001 | Zhang | |
| 6,200,560 B1 | 3/2001 | Couto | |
| 6,204,059 B1 | 3/2001 | Samulski | |
| 6,211,163 B1 | 4/2001 | Podsakoff | |
| 6,251,677 B1 | 6/2001 | Wilson | |
| 6,258,595 B1 | 7/2001 | Gao | |
| 6,261,551 B1 | 7/2001 | Wilson | |
| 6,265,389 B1 | 7/2001 | Burke | |
| 6,270,996 B1 | 8/2001 | Wilson | |
| 6,274,354 B1 | 8/2001 | Wilson | |
| 6,281,010 B1 | 8/2001 | Gao | |
| 6,325,998 B1 | 12/2001 | Podsakoff | |
| 6,335,011 B1 | 1/2002 | Podsakoff | |
| 6,365,394 B1 | 4/2002 | Gao | |
| 6,387,368 B1 | 5/2002 | Wilson | |
| 6,399,385 B1 | 6/2002 | Croyle | |
| 6,410,300 B1 | 6/2002 | Samulski | |
| 6,416,992 B1 | 7/2002 | Mejza | |
| 6,428,988 B1 | 8/2002 | Wilson | |
| 6,436,392 B1 | 8/2002 | Engelhardt | |
| 6,436,394 B1 | 8/2002 | Henderson | |
| 6,468,524 B1 | 10/2002 | Chiorini | |
| 6,468,771 B1 | 10/2002 | Einerhand | |

(Continued)

FOREIGN PATENT DOCUMENTS

| | | |
|---|---|---|
| EP | 1015619 | 7/2000 |
| EP | 1046711 | 10/2000 |

(Continued)

OTHER PUBLICATIONS

Krhac Levacic A, et al. Minicircle versus plasmid DNA delivery by receptor-targeted polyplexes. Hum Gene Ther. Aug. 21, 2017 Epub ahead of print.

(Continued)

*Primary Examiner* — Brian Whiteman
(74) *Attorney, Agent, or Firm* — Lando & Anastasi, LLP

(57) ABSTRACT

The invention relates to compositions and methods for the preparation, manufacture and therapeutic use of modulatory polynucleotides.

20 Claims, 2 Drawing Sheets
Specification includes a Sequence Listing.

(56) References Cited

U.S. PATENT DOCUMENTS

| | | |
|---|---|---|
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,186,552 B2 | 3/2007 | Wilson |
| 7,198,951 B2 | 4/2007 | Gao |
| 7,214,533 B2 | 5/2007 | Ferrandis |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,579,181 B2 | 8/2009 | ORiordan |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Fontanellas Rom |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,095,126 B2 | 8/2015 | Flavell |
| 9,101,645 B2 | 8/2015 | Watts |
| 9,102,943 B2 | 8/2015 | Shinmura |
| 9,107,884 B2 | 8/2015 | Chedotal |
| 9,115,373 B2 | 8/2015 | Hermens |
| 9,163,260 B2 | 10/2015 | Wilson |
| 9,169,483 B2 | 10/2015 | Davidson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,415,121 B2 | 8/2016 | Kaspar |
| 9,434,776 B2 | 9/2016 | Ando |
| 9,434,930 B2 | 9/2016 | Doudna |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,464,322 B2 | 10/2016 | Landfield |
| 9,475,845 B2 | 10/2016 | Asokan |
| 9,487,779 B2 | 11/2016 | Davidson |
| 9,493,788 B2 | 11/2016 | Gao |
| 9,499,597 B2 | 11/2016 | Miller |
| 9,506,068 B2 | 11/2016 | Inturrisi |
| 9,506,083 B2 | 11/2016 | Arbetman |
| 9,523,093 B2 | 12/2016 | Davidson |
| 9,528,126 B2 | 12/2016 | Qu |
| 9,539,307 B2 | 1/2017 | Kaspar |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |

(56) References Cited

U.S. PATENT DOCUMENTS

| | | |
|---|---|---|
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,616,090 B2 | 4/2017 | Conway |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,650,631 B2 | 5/2017 | Davidson |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Hermens |
| 9,719,070 B2 | 8/2017 | Vandenberghe |
| 9,719,106 B2 | 8/2017 | Wilson |
| 9,725,485 B2 | 8/2017 | Srivastava |
| 9,732,345 B2 | 8/2017 | Martin |
| 9,733,237 B2 | 8/2017 | Wichterle |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,824 B2 | 10/2017 | Kay |
| 9,783,825 B2 | 10/2017 | Chatterjee |
| 9,790,472 B2 | 10/2017 | Gao |
| 9,803,218 B2 | 10/2017 | Chatterjee |
| 10,041,090 B2 | 8/2018 | Gao |
| 10,047,377 B2 | 8/2018 | Piedras-Renteria |
| 10,093,927 B2 | 10/2018 | Davidson |
| 10,174,321 B2 | 1/2019 | Konstantinova |
| 10,208,318 B2 | 2/2019 | Barkats |
| 10,584,337 B2 * | 3/2020 | Sah .................. A61P 43/00 |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2003/0180756 A1 | 9/2003 | Shi |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0059005 A1 | 3/2005 | Tuschl |
| 2005/0064489 A1 | 3/2005 | Zhang |
| 2005/0261218 A1 | 11/2005 | Esau |
| 2006/0003451 A1 | 1/2006 | Gao |
| 2006/0204479 A1 | 9/2006 | Wilson |
| 2006/0229268 A1 | 10/2006 | Benjamin |
| 2007/0004042 A1 | 1/2007 | Gao |
| 2008/0008684 A1 | 1/2008 | Wilson |
| 2008/0015158 A1 | 1/2008 | Ichiro |
| 2008/0020992 A1 | 1/2008 | Rao |
| 2008/0050343 A1 | 2/2008 | Wilson |
| 2008/0050345 A1 | 2/2008 | Wilson |
| 2008/0075737 A1 | 3/2008 | Gao |
| 2008/0113375 A1 | 5/2008 | Khvorova |
| 2009/0118206 A1 | 5/2009 | Aronin |
| 2009/0215871 A1 | 8/2009 | Wilson |
| 2009/0275107 A1 | 11/2009 | Lock |
| 2009/0317417 A1 | 12/2009 | Vandenberghe |
| 2010/0004320 A1 | 1/2010 | Elmen |
| 2010/0036107 A1 | 2/2010 | Clawson |
| 2010/0247490 A1 | 9/2010 | Roy |
| 2010/0278791 A1 | 11/2010 | Wilson |
| 2010/0286378 A1 | 11/2010 | Li |
| 2011/0020816 A1 | 1/2011 | Chen |
| 2011/0039914 A1 | 2/2011 | Pavco |
| 2011/0111496 A1 | 5/2011 | Li |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2012/0046349 A1 | 2/2012 | Bell |
| 2012/0058102 A1 | 3/2012 | Wilson |
| 2012/0093853 A1 | 4/2012 | Wilson |
| 2012/0137379 A1 | 5/2012 | Gao |
| 2012/0258046 A1 | 10/2012 | Mutzke |
| 2012/0309050 A1 | 12/2012 | Kumon |
| 2013/0023033 A1 | 1/2013 | Wilson |
| 2013/0045186 A1 | 2/2013 | Gao |
| 2013/0101558 A1 | 4/2013 | Gao |
| 2013/0129668 A1 | 5/2013 | Firestein |
| 2013/0171726 A1 | 7/2013 | Roelvink |
| 2013/0195801 A1 | 8/2013 | Gao |
| 2013/0267582 A1 | 10/2013 | Kollipara |
| 2013/0296532 A1 | 11/2013 | Hermens |
| 2013/0323226 A1 | 12/2013 | Wilson |
| 2013/0323302 A1 | 12/2013 | Constable |
| 2014/0004565 A1 | 1/2014 | Rossomando |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0221462 A1 | 8/2014 | Puccio |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0152127 A1 | 6/2015 | Seinick |
| 2015/0159173 A1 | 6/2015 | Vandenberghe |
| 2015/0164906 A1 | 6/2015 | Zack |
| 2015/0183850 A1 | 7/2015 | Davidson |
| 2015/0197751 A1 | 7/2015 | Roelvink |
| 2015/0232840 A1 | 8/2015 | Aronin |
| 2015/0238610 A1 | 8/2015 | Sista |
| 2015/0301068 A1 | 10/2015 | Strooper |
| 2015/0307898 A2 | 10/2015 | Hermens |
| 2015/0315610 A1 | 11/2015 | Nishie |
| 2015/0335708 A1 | 11/2015 | Froelich |
| 2015/0374803 A1 | 12/2015 | Wolfe |
| 2015/0376612 A1 | 12/2015 | Lee |
| 2016/0032319 A1 | 2/2016 | Wright |
| 2016/0108373 A1 | 4/2016 | Bennett |
| 2016/0153992 A1 | 6/2016 | Buening |
| 2016/0166709 A1 | 6/2016 | Davidson |
| 2016/0251653 A1 | 9/2016 | Davidson |
| 2016/0264994 A1 | 9/2016 | Lawrence |
| 2016/0271192 A1 | 9/2016 | Roy |
| 2016/0272976 A1 | 9/2016 | Kaspar |
| 2016/0273058 A1 | 9/2016 | Akashika |
| 2016/0281084 A1 | 9/2016 | Davidson |
| 2016/0289275 A1 | 10/2016 | Chiorini |
| 2016/0289676 A1 | 10/2016 | Kaspar |
| 2016/0296605 A1 | 10/2016 | Zhang |
| 2016/0296694 A1 | 10/2016 | Bankiewicz |
| 2016/0319278 A1 | 11/2016 | Khvorova |
| 2016/0326524 A1 | 11/2016 | Flotte |
| 2016/0331897 A1 | 11/2016 | Anand |

(56) References Cited

U.S. PATENT DOCUMENTS

| | | |
|---|---|---|
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0346359 A1 | 12/2016 | Buchlis |
| 2016/0348106 A1 | 12/2016 | Harper |
| 2016/0354487 A1 | 12/2016 | Zhang |
| 2016/0355577 A1 | 12/2016 | Kelley |
| 2016/0355796 A1 | 12/2016 | Davidson |
| 2016/0355808 A1 | 12/2016 | Khvorova |
| 2016/0361439 A1 | 12/2016 | Agbandje-McKenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0004254 A1 | 1/2017 | Rossi |
| 2017/0007645 A1 | 1/2017 | Handa |
| 2017/0007669 A1 | 1/2017 | Sarkar |
| 2017/0007720 A1 | 1/2017 | Boye |
| 2017/0008939 A1 | 1/2017 | Khanna |
| 2017/0022498 A1 | 1/2017 | Cullen |
| 2017/0022507 A1 | 1/2017 | Reyon |
| 2017/0028082 A1 | 2/2017 | Wilson |
| 2017/0029849 A1 | 2/2017 | Harper |
| 2017/0035839 A1 | 2/2017 | Miller |
| 2017/0037410 A1 | 2/2017 | Swayze |
| 2017/0044504 A1 | 2/2017 | Schaffer |
| 2017/0044530 A1 | 2/2017 | Kay |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088819 A1 | 3/2017 | Vandendriessche |
| 2017/0088858 A1 | 3/2017 | Gao |
| 2017/0096460 A1 | 4/2017 | Froelich |
| 2017/0096646 A1 | 4/2017 | Roy |
| 2017/0105927 A1 | 4/2017 | Thorne |
| 2017/0107536 A1 | 4/2017 | Zhang |
| 2017/0112946 A1 | 4/2017 | Ikeda |
| 2017/0114340 A1 | 4/2017 | Mueller |
| 2017/0121734 A1 | 5/2017 | Cairns |
| 2017/0128581 A1 | 5/2017 | Freskgard |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Hermens |
| 2017/0151348 A1 | 6/2017 | Kaspar |
| 2017/0151416 A1 | 6/2017 | Kutikov |
| 2017/0152517 A1 | 6/2017 | Barkats |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Soumitra |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0218395 A1 | 8/2017 | Byrne |
| 2017/0226160 A1 | 8/2017 | Sonntag |
| 2017/0232072 A1 | 8/2017 | Yasuhiro |
| 2017/0232117 A1 | 8/2017 | Arbetman |
| 2017/0240885 A1 | 8/2017 | Deverman |
| 2017/0240921 A1 | 8/2017 | Gao |
| 2017/0246322 A1 | 8/2017 | Mendell |
| 2017/0247664 A1 | 8/2017 | Wright |
| 2017/0258996 A1 | 9/2017 | Anand |
| 2017/0260263 A1 | 9/2017 | Novák |
| 2017/0260545 A1 | 9/2017 | Qu |
| 2017/0274024 A1 | 9/2017 | McCown |
| 2017/0275337 A1 | 9/2017 | Srivastava |
| 2017/0298323 A1 | 10/2017 | Vandenberghe |
| 2017/0304464 A1 | 10/2017 | Kugler |
| 2017/0306354 A1 | 10/2017 | Gao |
| 2017/0306355 A1 | 10/2017 | Davidson |
| 2017/0321290 A1 | 11/2017 | Lubelski |
| 2018/0230490 A1 | 8/2018 | O'Riordan |
| 2018/0237772 A1 | 8/2018 | Yu |
| 2018/0298380 A1 | 10/2018 | Gao |

FOREIGN PATENT DOCUMENTS

| | | |
|---|---|---|
| EP | 1078096 | 2/2001 |
| EP | 1164195 | 12/2001 |
| EP | 1183380 | 3/2002 |
| EP | 1218035 | 7/2002 |
| EP | 1240345 | 9/2002 |
| EP | 1279740 | 1/2003 |
| EP | 1453547 | 9/2004 |
| EP | 1692262 B1 | 8/2006 |
| EP | 1696036 | 8/2006 |
| EP | 1847614 | 10/2007 |
| EP | 1849872 | 10/2007 |
| EP | 1857552 | 11/2007 |
| EP | 1900815 | 3/2008 |
| EP | 1944043 | 7/2008 |
| EP | 2007795 | 12/2008 |
| EP | 2164967 | 3/2010 |
| EP | 2172549 | 4/2010 |
| EP | 2198016 | 6/2010 |
| EP | 2220241 | 8/2010 |
| EP | 2220242 | 8/2010 |
| EP | 2250256 | 11/2010 |
| EP | 2292779 | 3/2011 |
| EP | 2292780 | 3/2011 |
| EP | 2301582 | 3/2011 |
| EP | 2325298 | 5/2011 |
| EP | 2359866 | 8/2011 |
| EP | 2360251 | 8/2011 |
| EP | 2383346 | 11/2011 |
| EP | 2453735 | 5/2012 |
| EP | 2497500 | 9/2012 |
| EP | 2524037 | 11/2012 |
| EP | 2531604 | 12/2012 |
| EP | 2660325 | 11/2013 |
| EP | 2699270 | 2/2014 |
| EP | 2737071 | 6/2014 |
| EP | 2814958 | 12/2014 |
| EP | 2871239 | 5/2015 |
| EP | 2879719 | 6/2015 |
| EP | 2906580 | 8/2015 |
| EP | 2933336 | 10/2015 |
| EP | 2943567 | 11/2015 |
| EP | 3058959 | 8/2016 |
| EP | 3067417 | 9/2016 |
| EP | 2176283 | 11/2016 |
| EP | 3108000 | 12/2016 |
| EP | 3117005 | 1/2017 |
| EP | 3134431 | 3/2017 |
| EP | 3168298 | 5/2017 |
| EP | 3174981 | 6/2017 |
| EP | 3209311 | 8/2017 |
| EP | 2311967 | 9/2017 |
| EP | 3215602 | 9/2017 |
| EP | 3221453 | 9/2017 |
| EP | 3221456 | 9/2017 |
| EP | 3224376 | 10/2017 |
| EP | 3230441 | 10/2017 |
| EP | 3235827 | 10/2017 |
| EP | 3237618 A1 | 11/2017 |
| WO | 1993009239 | 5/1993 |

(56) References Cited

FOREIGN PATENT DOCUMENTS

| | | |
|---|---|---|
| WO | 1995034670 | 12/1995 |
| WO | 1996017947 | 6/1996 |
| WO | 1996023810 | 8/1996 |
| WO | 1996030540 | 10/1996 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001075164 A1 | 10/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003087382 | 10/2003 |
| WO | 2003087383 | 10/2003 |
| WO | 2004027030 A2 | 4/2004 |
| WO | 2004044003 | 5/2004 |
| WO | 2004083441 | 9/2004 |
| WO | 2004108922 | 12/2004 |
| WO | 2004111248 | 12/2004 |
| WO | 2005005610 | 1/2005 |
| WO | 2005012537 | 2/2005 |
| WO | 2005111220 | 11/2005 |
| WO | 2006102072 | 9/2006 |
| WO | 2007130519 | 11/2007 |
| WO | 2007148971 | 7/2009 |
| WO | 2009134681 | 11/2009 |
| WO | 2011038187 | 3/2011 |
| WO | 2011054976 | 5/2011 |
| WO | 2011122950 | 10/2011 |
| WO | 2010109053 | 11/2011 |
| WO | 2012057363 | 5/2012 |
| WO | 2012114090 | 8/2012 |
| WO | 2012144446 | 10/2012 |
| WO | 2012149646 A1 | 11/2012 |
| WO | 2013078199 | 5/2013 |
| WO | 2013126605 A1 | 8/2013 |
| WO | 2013164793 | 11/2013 |
| WO | 2013170078 | 11/2013 |
| WO | 2014016817 A2 | 1/2014 |
| WO | 2014016817 A2 | 1/2014 |
| WO | 2014107763 A1 | 7/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015018503 | 2/2015 |
| WO | 2014186746 | 3/2015 |
| WO | 2015031392 | 3/2015 |
| WO | 2015031686 | 4/2015 |
| WO | 2015044292 | 4/2015 |
| WO | 2015060722 | 4/2015 |
| WO | 2015084254 A1 | 6/2015 |
| WO | 2015106273 | 7/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015143078 A1 | 9/2015 |
| WO | 2015127128 | 11/2015 |
| WO | 2015179525 A1 | 11/2015 |
| WO | 2015196179 | 12/2015 |
| WO | 2016019364 | 2/2016 |
| WO | 2016040347 A2 | 3/2016 |
| WO | 2016054554 | 4/2016 |
| WO | 2016054557 | 4/2016 |
| WO | 2016065001 | 4/2016 |
| WO | 2016077687 A1 | 5/2016 |
| WO | 2016077689 A1 | 5/2016 |
| WO | 2016081811 | 5/2016 |
| WO | 2016081927 | 5/2016 |
| WO | 2016102664 | 6/2016 |
| WO | 2016109649 | 7/2016 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130589 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016161374 | 10/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196328 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017024111 A1 | 2/2017 |
| WO | 2017058892 | 4/2017 |
| WO | 2017062983 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017079768 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017106236 | 6/2017 |
| WO | 2017112948 | 6/2017 |
| WO | 2017122789 | 7/2017 |
| WO | 2017136202 | 8/2017 |
| WO | 2017136536 | 8/2017 |
| WO | 2017139381 | 8/2017 |
| WO | 2017143100 | 8/2017 |
| WO | 2017147477 | 8/2017 |
| WO | 2017152149 | 9/2017 |
| WO | 2017155973 | 9/2017 |
| WO | 2017160360 | 9/2017 |
| WO | 2017161273 A1 | 9/2017 |
| WO | 2017165859 | 9/2017 |
| WO | 2017172733 | 10/2017 |
| WO | 2017172772 | 10/2017 |
| WO | 2017173043 | 10/2017 |
| WO | 2017173283 | 10/2017 |

(56) References Cited

FOREIGN PATENT DOCUMENTS

| WO | 2017180854 | | 10/2017 |
|---|---|---|---|
| WO | 2017181162 | | 10/2017 |
| WO | 2017184879 | | 10/2017 |
| WO | 2017189963 | A1 | 11/2017 |
| WO | 2017190031 | | 11/2017 |
| WO | 2017192699 | | 11/2017 |
| WO | 2017192750 | | 11/2017 |
| WO | 2018220211 | A1 | 12/2018 |
| WO | 2019043027 | A1 | 3/2019 |

OTHER PUBLICATIONS

Moffett HF, et al. Hit-and-run programming of therapeutic cytoreagents using mRNA nanocarriers. Nat Commun. Aug. 30, 2017;8(1):389.

Morabito G, Giannelli SG, Ordazzo G, Bido S, Castoldi V, Indrigo M, Cabassi T, Cattaneo S, Luoni M, Cancellieri C, Sessa A, Bacigaluppi M, Taverna S, Leocani L, Lanciego JL, Broccoli V. Mol Ther. Dec. 6, 2017;25(12):2727-2742. Epub Aug. 10, 2017.

Matsuzaki Y, Konno A, Mochizuki R, Shinohara Y, Nitta K, Okada Y, Hirai H. Neurosci Lett. Nov. 23, 2017. [Epub ahead of print].

Naidoo J, et al. Extensive Transduction and Enhanced Spread of a Modified AAV2 Capsid in the Non-human Primate CNS. Mol Ther. Jul. 12, 2018 Epub ahead of print.

Van Lieshout LP, et al. A Novel Triple-Mutant AAV6 Capsid Induces Rapid and Potent Transgene Expression in the Muscle and Respiratory Tract of Mice. Mol Ther Meth Clin Dev Jun. 15, 2018.

Jankovic J, et al. Safety and Tolerability of Multiple Ascending Doses of PRX002/RG7935, an Anti-α-Synuclein Monoclonal Antibody, in Patients With Parkinson Disease: A Randomized Clinical Trial. JAMA Neurol. Jun. 18, 2018 Epub ahead of print.

Adams D, et al. Patisiran, an RNAi Therapeutic, for Hereditary Transthyretin Amyloidosis. N Engl J Med Jul. 5, 2018;379(1):11-21.

Benson MD, et al. Inotersen Treatment for Patients with Hereditary Transthyretin Amyloidosis. N Engl J Med. Jul. 5, 2018;379(1):22-31.

Massaro G, et al. Fetal gene therapy for neurodegenerative disease of infants. Nat Med. Jul. 16, 2018 Epub ahead of print.

Hudry E, et al. Efficient gene transfer to the central nervous system by single stranded Anc80L65. Mol Ther Meth Clin Dev. Jul. 15, 2018.

Di Maio R, et al. LRRK2 activation in idiopathic Parkinson's disease. Sci Transl Med. Jul. 25, 2018; 10(451).

Man JHK, et al. Cell reprogramming approaches in gene- and cell-based therapies for Parkinson's disease. J Control Release Jul. 17, 2018;286:114-124 Epub ahead of print.

Stoker TB, et al. Regenerative therapies for Parkinson's Disease: An Update.

Chandran JS, et al. Gene therapy in the nervous system: failures and successes. Adv Exp Med Biol. 2017;1007:241-257.

Tse LV, et al. Mapping and engineering function domains of the assembly-activating protein of adeno-associated viruses. J. Virol. Jun. 29, 2018;92(14).

Auyeung VC, et al. Beyond secondary structure: primary sequence determinants license pri-miRNA hairpins for processing. Cell. Feb. 2013;152(4):844-858.

Fellman C, et al. An optimized microRNA backbone for effective single-copy RNAi. Cell Rep. Dec. 2013;5(6):1704-1713.

Pourshafie N, et al. Systemic Delivery of MicroRNA Using Recombinant Adeno-associated Virus Serotype 9 to Treat Neuromuscular Diseases in Rodents. J Vis Exp. Aug. 10, 2018;(138).

Chien YH, et al. Efficacy and safety of AAV2 gene therapy in children with aromatic L-amino acid decarboxylase deficiency: an open-label, phase 1/2 trial Lancet Chil Adolesc Health Dec. 2017;1(4):265-273.

Burg M, et al. Atomic structure of rationally engineered gene delivery vector, AAV2.5. Journal of Structural Biology. Sep. 2018 203(3):236-241.

Gowanlock D, et al. A designer AAV variant permits efficient retrograde access to projection neurons. Neuron. Oct. 19, 2016;92(2):372-382.

International Search Report issued in corresponding PCT Application No. PCT/US2015/060564 dated Mar. 2, 2016.

Ha et al., Regulation of microRNA biogenesis. Nat Rev Mol Cell Bio, Aug. 2014, vol. 15, No. 8, pp. 509-524.

Boudreau RL, et al. Artificial microRNAs as siRNA shuttles: improved safety as compared to shRNAs in vitro and in vivo. The American Society of Gene Therapy. 2009; 17(1):169-175.

International Search Report issued in corresponding PCT Application No. PCT/US2017/033268 dated Oct. 5, 2017.

Kawaoka et al. Bombyx small RNAs: genomic defense system against transposons in the silkworm, Bombyx mori. Insect Biochem Mol Biol. Dec. 2008;38(12):1058-65. Epub Mar. 27, 2008.

Muzyczka N, et al. AAV's Golden Jubilee. Mol Ther. May 2015;23(5):807-8.

Maniatis T. et al.,Molecular Cloning. CSH Laboratory, NY, N.Y. (1982).

Merten OW, et al. Viral vectors for gene therapy and gene modification approaches. Biochem Eng J. Apr. 2016,108:98-115.

Philiport, et al. Liposomes as tools in Basic Research and Industry. CRC Press, Ann Arbor, Mich. (1995).

Kailasan S, et al. Parvovirus Family Conundrum: What makes a killer? Annu Rev Virol. Nov. 2015;2(1):425-50.

Rutledge EA, et al. Infectious clones and vectors derived from adeno-associated virus (AAV) serotypes other than AAV type 2. J Virol. Jan. 1998;72(1):309-19.

Pillay S, et al. An essential receptor for adeno-associated virus infection. Nature. Nov. 17, 2016;539(7629):456.

Platt MP, et al. Embryonic disruption of the candidate dyslexia susceptibility gene homolog Kiaa0319-like results in neuronal migration disorders. Neuroscience. Sep. 17, 2013;248:585-93.

Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.

Poon MW, et al. Dyslexia-associated kiaa0319-like protein interacts with axon guidance receptor nogo receptor 1. Cell Mol Neurobiol. Jan. 2011;31(1):27-35.

Myers EW, et al. Optimal alignments in linear space. Comput Appl Biosci. Mar. 1988;4(1):11-7.

Smith DW, et al. Biocomputing: Informatics and Genome Projects. Academic Press, New York, 1993.

Kozak M. Interpreting cDNA sequences: some insights from studies on translation. Mamm Genome. Aug. 1996;7(8):563-74.

Kozak M. Point mutations define a sequence flanking the AUG initiator codon that modulates translation by eukaryotic ribosomes. Cell. Jan. 31, 1986;44(2):283-92.

Kozak M. The scanning model for translation: an update. J Cell Biol. Feb. 1989;108(2):229-41.

Heim R, et al. Engineering green fluorescent protein for improved brightness, longer wavelengths and fluorescence resonance energy transfer. Curr Biol. Feb. 1, 1996;6(2):178-82.

Heim R,et al. Improved green fluorescence Nature 373, 663-664 (Feb. 23, 1995); doi:10.1038/373663b0.

Nygaard S, et al. A universal system to select gene-modified hepatocytes in vivo. Sci Transl Med. Jun. 2016;8(342):342ra79.

Smith RH, et al. Germline viral "fossils" guide in silico reconstruction of a mid-Cenozoic era marsupial adeno-associated virus. Sci Rep. Jul. 2016;6:28965.

Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.

O'reilly DR, et al. Baculovirus expression vectors: a laboratory manual. Oxford University Press, 1994.

Oliva B, et al. An automated classification of the structure of protein loops. J Mol Biol. Mar. 7, 1997;266(4):814-30.

Samaranch L, et al. MR-guided parenchymal delivery of adeno-associated viral vector serotype 5 in non-human primate brain. Gene Ther. Apr. 2017;24(4):253-261.

(56) References Cited

OTHER PUBLICATIONS

Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice Hum Gene Ther. Aug. 10, 2016.
Hordeaux J., et al. Efficient central nervous system AAVrh10-mediated intrathecal gene transfers in adult and neonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates. Mol Ther. Aug. 2015, 23(8):1298-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deficient canine model of the late infantile form of Batten Disease. Sci Transl Med. Nov. 2015;7(313):313ra180.
Kothari P, et al. Iodine-124 Labeled Adeno-Associated Virus: A Promising Tool for Tracking Gene Therapy. Journal of Nuclear Medicine. May 2015, 56 (supplement 3), 494-494.
Landegger LD, et al. A synthetic AAV vector enables safe and efficient gene transfer to the mammalian inner ear. Nat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016:67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li SY, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(10):647-56.
Mendell JR, et al. Follistatin Gene Therapy for Sporadic Inclusion Body Myositis Improves Functional Outcomes. Mol Ther. Apr. 2017;25(4):870-879.

Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Russian Official Action (translated) dated Jun. 4, 2019 received in corresponding Russian application No. 2017116544.
Russian Search Report (translated) dated Jun. 4, 2019 received in corresponding Russian application No. 2017116544.
Australian Examination Report No. 1 dated Jun. 5, 2019 received in corresponding Australian application No. 2015346164.
Extended Search Report dated Dec. 17, 2019 received in corresponding European application No. 17800147.5.
Tobias Grossl et al: "A Novel Artificial MicroRNA Expressing AAV Vector for Phospholamban Silencing in Cardiomyocytes Improves Ca2+ Uptake into the Sarcoplasmic Reticulum", PLOS One, vol. 9, No. 3, Mar. 26, 2014, p. e92188.
Bofill-De Ros Xavier et al: "Guidellines for the optimal design of miRNA-based shRNAs", Methods, Academic Pres, NL, vol. 103, Apr. 12, 2016, pp. 157-166.
Miyagashi M et al: "Optimization of an siRNA-expression systems with an improved hairpin and its significant suppressive effects in mammalian cells", Journal of Gene Medicine, John Wiley & Sons, Inc, US, vol. 6, Mar. 8, 2004, pp. 715-723.
Du Guangwei et al: "Design of expression vectors for RNA interference based on miRNAs and RNA splicing", FEBS Journal, Wiley-Blackwell Publishing Ltd, GB, vol. 273, No. 23, Nov. 3, 2006, pp. 5421-5427.
Raquel Calloni et al: "Scaffolds for Artificial miRNA Expression in Animal Cells", Human Gene Therapy Methods, vol. 26, No. 5, Aug. 17, 2015, pp. 162-174.
Nick C.T. Schopman et al: "Optimization of shRNA inhibitors by variation of the terminal loop sequence", Antiviral Research, vol. 86, No. 2, Feb. 25, 2010, pp. 204-211.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector Nat Med. Oct. 1997;3(10):1145-9.

(56) References Cited

OTHER PUBLICATIONS

Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016;12(1):e1005399.
Kailasan S, et al. Structure of an Enteric Pathogen, Bovine Parvovirus. J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Ferla R, et al. Prevalence of anti-adeno-associated virus serotype 8 neutralizing antibodies and arylsulfatase B cross-reactive immunologic material in mucopolysaccharidosis VI patient candidates for a gene therapy trial. Hum Gene Ther. Mar. 2015;26(3):145-52.
Harrington EA, et al. Neutralizing Antibodies Against Adeno-Associated Viral Capsids in Patients with mut Methylmalonic Acidemia. Hum Gene Ther. May 2016;27(5):345-53.
Kotterman MA, et al. Antibody neutralization poses a barrier to intravitreal adeno-associated viral vector gene delivery to non-human primates. Gene Ther. Feb. 2015;22(2):116-26.
Hu JE, et al. Opposing effects of viral mediated brain expression of apolipoprotein E2 (apoE2) and apoE4 on apoE lipidation and A beta metabolism in apoE4-targeted replacement mice. Mol Neurodegener. Mar. 2015, 10:6.
Zhao L et al. Intracerebral adeno-associated virus gene delivery of apolipoprotein E2 markedly reduces brain amyloid pathology in Alzheimer's disease mouse models Neurobiol Aging. Aug. 2016;44:159-72.
Fol R et al. Viral gene transfer of APPsα rescues synaptic failure in an Alzheimer's disease mouse model. Acta Neuropathol. Feb. 2016;131(2):247-66.
Gant JC, et al. Reversal of Aging-Related Neuronal Ca2+ Dysregulation and Cognitive Impairment by Delivery of a Transgene Encoding FK506-Binding Protein 12.6/1b to the Hippocampus. J Neurosci. Jul. 2015, 29;35(30):10878-87.
Ren J, et al. Noninvasive tracking of gene transcript and neuroprotection after gene therapy. Gene Ther. Jan. 2016;23(1):1-9.
Cirulli ET, et al. Exome sequencing in amyotrophic lateral sclerosis identifies risk genes and pathways. Science. Mar. 27, 2015;347(6229):1436-41.
Häggmark A, et al. Plasma profiling reveals three proteins associated to amyotrophic lateral sclerosis. Ann Clin Transl Neurol. Aug. 2014;1(8):544-53.

Jackson KL, et al. Preservation of forelimb function by UPF1 gene therapy in a rat model of TDP-43-induced motor paralysis. Gene Ther. Jan. 2015, 22(1):20-8.
Herranz-Martin S, et al. Viral delivery of C9ORF72 hexanucleotide repeat expansions in mice lead to repeat length dependent neuropathology and behavioral deficits. Dis Model Mech. May 26, 2017. Epub ahead of print.
Jara JH, et al. Healthy and diseased corticospinal motor neurons are selectively transduced upon direct AAV2-2 injection into the motor cortex. Gene Ther. Mar. 2016;23(3):272-82.
Borel F et al. Therapeutic rAAVrh10 Mediated SOD1 Silencing in Adult SOD1(G93A) Mice and Nonhuman Primates. Hum Gene Ther. Jan. 2016;27(1):19-31.
Frakes AE, et al. Additive amelioration of ALS by co-targeting independent pathogenic mechanisms. Ann Clin Transl Neurol. Jan. 2017;4(2):76-86.
Van Zundert B et al. Silencing Strategies for Therapy of SOD1-Mediated ALS. Neurosci Lett. Aug. 6, 2016.
Stoica et al. Adeno-associated virus-delivered artificial microRNA extends survival and delays paralysis in an amyotrophic lateral sclerosis mouse model. Ann Neurol. Apr. 2016;79(4):687-700.
Picher-Martel V et al. From Animal Models to Human Disease: A Genetic Approach for Personalized Medicine in ALS. Acta Neuropathol Commun. Jul. 11, 2016;4(1):70.
Hocquemiller M et al. Adeno-Associated Virus-Based Gene Therapy for CNS Diseases. Hum Gene Ther. Jul. 2016;27(7):478-96.
Stoica L et al. Adeno Associated Viral Vector Delivered RNAi for Gene Therapy of SOD1 Amyotrophic Lateral Sclerosis Front Mol Neurosci. Aug. 2, 2016;9:56.
Verhelle A, et al. AAV9 delivered bispecific nanobody attenuates amyloid burden in the gelsolin amyloidosis mouse model. Hum Mol Genet. Apr. 2017;26(7):1353-1364.
Vodicka P, et al. Autophagy Activation by Transcription Factor EB (TFEB) in Striatum of HDQ175/Q7 Mice. J Huntingtons Dis. Oct. 2016;5(3):249-260.
Vodicka P, et al. Effects of Exogenous NUB1 Expression in the Striatum of HDQ175/Q7 Mice. J Huntingtons Dis. Jun. 2016;5(2):163-74.
Amaro IA et al. An Intrabody Drug (rAAV6-INT41) Reduces the Binding of N-Terminal Huntingtin Fragment(s) to DNA to Basal Levels in PC12 Cells and Delays Cognitive Loss in the R6/2 Animal Model. J Neurodegener Dis. 2016;2016:7120753.
Monteys AM, et al. CRISPR/Cas9 Editing of the Mutant Huntingtin Allele In Vitro and In Vivo. Mol Ther. Jan. 2017;25(1):12-23.
Hadaczek P et al. Widespread AAV1- and AAV2-mediated Transgene Expression in the Nonhuman Primate Brain: Implications for Huntington's Disease. Mol Ther Methods Clin Dev. Jun. 29, 2016;3:16037.
Miniarikova J et al. Design, Characterization, and Lead Selection of Therapeutic miRNAs Targeting Huntingtin for Development of Gene Therapy for Huntington's Disease. Mol Ther Nucleic Acids. Mar. 22, 2016;5:e297.
Keeler AM et al. Cellular Analysis of Silencing the Huntington's Disease Gene Using AAV9 Mediated Delivery of Artificial Micro RNA into the Striatum of Q140/0140 Mice J Huntingtons Dis. Oct. 1, 2016 ;5(3):239-248.
Green F, et al. Axonal transport of AAV9 in nonhuman primate brain. Gene Ther. Jun. 2016;23(6):520-6.
Bisset DR, et al. Therapeutic impact of systemic AAV-mediated RNA interference in a mouse model of myotonic dystrophy. Hum Mol Genet. Sep. 2015;24(17):4971-83.
Gaura V, et al. Association between motor symptoms and brain metabolism in early huntington disease. JAMA Neurol. Sep. 1, 2017;74(9):1088-1096.
Dietrich P, et al. Elimination of huntingtin in the adult mouse leads to progressive behavioral deficits, bilateral thalamic calcification, and altered brain iron homeostasis. PLoS Genet. Jul. 17, 2017;13(7):e1006846.
Miniarikova J, et al. AAV5-miHTT gene therapy demonstrates suppression of mutant huntingtin aggregation and neuronal dysfunction in a rat model of Huntington's disease. Gene Ther. Aug. 3, 2017. doi: 10.1038/gt.2017.71.

(56) References Cited

OTHER PUBLICATIONS

Yang S, et al. CRISPR/Cas9-mediated gene editing ameliorates neurotoxicity in mouse model of Huntington's disease. J Clin Invest. Jun. 19, 2017. Epub ahead of print.
Pfister EL, et al. Safe and Efficient Silencing with a Pol II, but Not a Pol III, Promoter Expressing an Artificial miRNA Targeting Human Huntingtin. Mol Ther Nucleic Acids. Jun. 16, 2017;7:324-334.
Evers MM, et al. AAV5-miHTT Gene Therapy Demonstrates Broad Distribution and Strong Human Mutant Huntingtin Lowering in a Huntington's Disease Minipig Model. Mol Ther. Jun. 25, 2018 Epub ahead of print.
Mestre TA .Recent advances in the therapeutic development for Huntington disease.Parkinsonism Relat Disord Dec. 12, 2018. [Epub ahead of print].
Martier R, et al. Artificial microRNAs targeting C9ORF2 have the potential to reduce accumulation of the intra-nuclear transcripts in ALS and FTD patients. Molecular Therapy Nucleic Acids. Jan. 22, 2019. DOI: https.//doi.org/10.1016 [Epub ahead of print] Review.
Miniarikova et al., Translation of MicroRNA-Based Huntingtin-Lowering Therapies from Preclinical Studies to the Clinic. Mol Ther. Apr. 4, 2018;26(4):947-962.
Buning and Srivastava. Capsid Modifications for Targeting and Improving the Efficacy of AAV Vectors. vol. 12, p. 248-265, Mar. 15, 2019.
Hudry E, Vandenberghe LH. Therapeutic AAV Gene Transfer to the Nervous System: A Clinical Reality. Neuron. Mar. 6, 2019;101(5):839-862.
Long et al., Validation of a prognostic index for Huntington's disease. Mov Disord. Feb. 2017;32(2):256-263. Epub Nov. 28, 2016.
Ross et al., Huntington's disease: from molecular pathogenesis to clinical treatment. Lancet Neurol. Jan. 2011;10(1):83-98.
Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. Epub Mar. 21, 2014.
Walker, Huntington's disease. Lancet. Jan. 20, 2007;369(9557):218-28.
Miniarikova J et al., Translation of MicroRNA-Based Huntingtin-Lowering Therapies from Preclinical Studies to the Clinic, 2018, 26:947-962.
Spronck et al., AAV5-miHTT Gene Therapy Demonstrates Sustained Huntingtin Lowering and Functional Improvement in Huntington Disease Mouse Models. Mol Ther Methods Clin Dev. Mar. 16, 2019;13:334-343.
Tabrizi SJ et al., Targeting Huntingtin Expression in Patients with Huntington's Disease. N Engl J Med. May 6, 2019. [Epub ahead of print].
Zeitler et al., Allele-selective transcriptional repression of mutant HTT for the treatment of Huntington's disease. Nat Med. Jul. 2019;25(7):1131-1142.
Loring HS, et al. Development of rAAV2-CFTR: History of the First rAAV Vector Product to be Used in Humans. Hum Gene Ther Methods. Apr. 2016;27(2):49-58.
Valdmanis P, et al. Future of rAAV gene therapy: Platform for RNAi, Gene Editing and Beyond Hum Gene Ther. Apr. 2017;28(4):361-372.
Timothy M. Miller et al: "Virus-delivered small RNA silencing sustains strength in amyotrophic lateral sclerosis", Annals of Neurology., vol. 57, No. 5, May 1, 2005 (May 1, 2005), pp. 773-776.
Chris Towne et al: "Systemic AAV6 Delivery Mediating RNA Interference Against SOD1: Neuromuscular Transduction Does Not Alter Disease Progression in fALS Mice", Molecular Therapy: The Journal of the American Society of Gene Therapy, vol. 16, No. 6, Jun. 1, 2008 (Jun. 1, 2008), pp. 1018-1025.
Takayuki Kubodera et al: "In Vivo Application of an RNAi Strategy for the Selective Suppression of a Mutant Allele", Human Gene Therapy, vol. 22, No. 1, Jan. 1, 2011 (Jan. 1, 2011), pp. 27-34.

Yuki Saito et al: "Transgenic Small Interfering RNA Halts Amyotrophic Lateral Sclerosis in a Mouse Model", Journal of Biological Chemistry, vol. 280, No. 52, Oct. 12, 2005 (Oct. 12, 2005), pp. 42826-42830.
Rui Wu et al: "Nerve Injection of Viral Vectors Efficiently Transfers Transgenes into Motor Neurons and Delivers RNAi Therapy Against ALS", Antioxidants and Redox Signaling, vol. 11, No. 7, Jul. 1, 2009 (Jul. 1, 2009), pp. 1523-1534.
H. Zhou: "An RNA polymerase II construct synthesizes short-hairpin RNA with a quantitative indicatorand mediates nighly efficien RNAi", Nucleic Acids Research, vol. 33, No. 6, Mar. 23, 2005 (Mar. 23, 2005), pp. e62-e62.
Monica Nizzardo et al: "Research advances in gene therapy approaches for the treatment of amyotrophic lateral sclerosis", CMLS Cellular and Molecular Life Sciences, Birkhauser-Verlag, BA, vol. 69, No. 10, Nov. 18, 2011 (Nov. 18, 2011), pp. 1641-1650.
Fukuoka M, et al. Supplemental Treatment for Huntington's Disease with miR-132 that Is Deficient in Huntington's Disease Brain. Mol. Ther. Nucleic Acids. Jun. 1, 2018;11:79-90.
Pfister EL, et al. Artificial miRNAs Reduce Human Mutant Huntingtin Throughout the Striatum in a Transgenic Sheep Model of Huntington's Disease. Hum Gene Ther Jun. 2018;29(6):663-673.
McCampbell A, et al. Antisense oligonucleotides extend survival and reverse decrement in muscle response in ALS models. J Clin Invest. Jul. 16, 2018 Epub ahead of print.
Jannitti T, et al. Translating SOD1 Gene Silencing toward the Clinic: A Highly Efficacious, Off-Target-free, and Biomarker-Supported Strategy for fALS. Mol Ther Nucleic Acids. Sep. 7, 2018.
McGurk L, et al. Poly(ADP-Ribose) Prevents Pathological Phase Separation of TDP-43 by Promoting Liquid Demixing and Stress Granule Localization. Molecular Cell. Aug. 9, 2018.
Wang D, et al. Adeno-associated virus vector as a platform for gene therapy delivery. Nat Rev Drug Discov. Feb. 1, 2019. doi: 10.1038/s41573-019-0012-9. [Epub ahead of print] Review.
Chen YH etl a., Viral Vectors for Gene Transfer. Curr Protoc Mouse Biol. Dec. 2018;8(4):e58.
Betancur JG et al., miRNA-like duplexes as RNAi triggers with improved specificity. Front Genet. Jul. 12, 2012;3:127.
Chung et al., Polycystronic RNA polymerase II expression vectors for RNA interference based on BIC/miR-155. Nucleic Acids Res. Apr. 13, 2006;34(7):e53.
Cullen BR. Induction of stable RNA interference in mammalian cells. Gene Ther. Mar. 2006;13(6):503-8.
Dow LE et al., A pipeline for the generation of shRNA transgenic mice. Nat Protoc. Feb. 2, 2012;7(2):374-93.
Fellmann C. et al., Functional identification of optimized RNAi triggers using a massivelyparallel sensor assay. Mol Cell. Mar. 18, 2011;41(6):733-46.
Gu S et al., The loop position of shRNAs and pre-miRNAs is critical for the accuracy of dicer processing in vivo. Cell. Nov. 9, 2012;151(4):900-911.
Han J. et al., Molecular basis for the recognition of primary microRNAs by the Drosha-DGCR8 complex. Cell. Jun. 2, 2006;125(5):887-901.
Ketley A. et al., The miR-20 microRNA family targets smoothened to regulate hedgehog signallling in zebrafish early muscle development. PLoS One. Jun. 5, 2013;8(6):e65170.
Liu YP et al., Inhibition of HIV-1 by multiple siRNAs expressed from a single microRNApolycistron. Nucleic Acids Res. May 2008;36(9):2811-24.
Park JE et al., Dicer recognizes the 5' end of RNA for efficient and accurate processing. Nature. Jul. 13, 2011;475(7355)1201-5.
Schwarz DS et al., Asymmetry in the assembly of the RNAi enzyme complex. Cell. Oct. 17, 2003;115(2)1199-208.
Seitz H et al., A 5' -uridine amplifies miRNA/miRNA* asymmetry in *Drosophila* by promoting RNA-induced silencing complex formation. Silence. Jun. 7, 2011;2:4.
Wang D et al., Adeno-associated virus vector as a platform for gene therapy delivery. Nat Rev Drug Discov. Feb. 1, 2019.
Borel F et al., Recombinant AAV as a platform for translating the therapeutic potential of RNA interference .Mol Ther. Apr. 2014;22(4):692-701.

(56) References Cited

OTHER PUBLICATIONS

Pfeifer A et al., Pharmacological potential of RNAi—focus on miRNA. Pharmacol Ther. Jun. 2010;126(3)1217-27.
Xie J et al., Short DNA Hairpins Compromise Recombinant Adeno-Associated Virus Genome Homogeneity. Mol Ther. Jun. 7, 2017;25(6):1363-1374.
Ly CV et al., Emerging antisense oligonucleotide and viral therapies for amyotrophic lateral sclerosis. Curr Opin Neurol. Oct. 2018;31(5):648-654.
Challis et al., Systemic AAV vectors for widespread and targeted gene delivery in rodents. Nat Protoc. Feb. 2019;14(2)1379-414.
Elbashir et al., Functional anatomy of siRNAs for mediating efficient RNAi in *Drosophila melanogaster* embryo lysate. EMBO J. Dec. 3, 2001; 20(23)16877-88.
Powell et al., Viral Expression Cassette Elements to Enhance Transgene Target Specificity and Expression in Gene Therapy. Discov Med. Jan. 2015; 19(102):49-57.
Mieizsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Pacourei S, et al. AAV-ID: A Rapid and Robust Assay for Batch-to-Batch Consistency Evaluation of AAV Preparations. Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol. Dec. 1992;66(12):6922-30.
Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009; 17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1):R42-52.
Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Miao Y, et al. Single point mutation in adeno-associated viral vectors—DJ capsid leads to improvement for gene delivery in vivo BMC Biotechnol. Jan. 2016;16:1.
Marsic D et al. Altering Tropism of rAAV by Directed Evolution. Methods of Mol Biol. 2016;1382:151-73.
Tu MY, et al. Role of capsid proteins in parvoviruses infection. Virol J. Aug. 2015, 4;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Ling C, et al. Development of Optimized AAV Serotype Vectors for High-Efficiency Transduction at Further Reduced Doses Hum Gene Ther Methods. Aug. 2016;27(4):143-9.
Pillay S, et al. An essential receptor for adeno-associated virus infection. Nature. Feb. 2016;530(7588):108-12.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther. Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors. Mol Ther. Apr. 2016;24(4):726-35.
Davis AS, et al. Rational design and engineering of a modified adeno-associated virus (AAV1)-based vector system for enhanced retrograde gene delivery. Neurosurgery Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Ling C, et al. High-Efficiency Transduction of Primary Human Hematopoietic Stem/Progenitor Cells by AAV6 Vectors: Strategies

(56) References Cited

OTHER PUBLICATIONS for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Xie J, et al. Short DNA Hairpins Compromise Recombinant Adeno-Associated Virus Genome Homogeneity. Mol Ther. Apr. 24, 2017. Epub ahead of print.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016;9(1):52.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction Hum Gene Ther. Apr. 2016;27(4):309-24.
Hudry EM, et al. Exosome-associated AAV vector as a robust and convenient neursocience tool Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-Invasive Tracking of Adeno-Associated Gene Transfer Vectors. Sci Rep. Jan. 2017;7:39594.
Xie Q, et al. The 2.8 Å Electron Microscopy Structure of Adeno-Associated Virus—DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.
Stahl PH, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. Nov. 22, 2014, 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016,90(21):9878-9888.
Wang LL, et al. Comparative study of liver gene transfer with AAV vectors based on endogenous and engineered AAV capsids. Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Ai J, et al. A Scalable and Accurate Method for Quantifying Vector Genomes of Recombinant Adeno-Associated Viruses in Crude Lysate. Hum Gene Ther Methods Apr. 13, 2017 Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.

(56) References Cited

OTHER PUBLICATIONS

Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.

Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.

Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.

Kirnbauer R, et al. Virus-like particles of bovine papillomavirus type 4 in prophylactic and therapeutic immunization. Virology May 1, 1996;219(1):37-44.

Kohlbrenner E, et al. Production and Characterization of Vectors Based on the Cardiotropic AAV Serotype 9. Methods Mol Biol. 2017;1521:91-107.

Kotin RM, et al. Large-scale recombinant adeno-associated virus production. Hum Mol Genet. Apr. 15, 2011;20(R1):R2-6 doi: 10.1093/hmg/ddr141. Epub Apr. 29, 2011.

Kotin RM, et al. Manufacturing clinical grade recombinant adeno-associated virus using invertebrate cell lines. Hum Gene Ther. Mar. 28, 2017. Epub ahead of print.

Kotterman MA, et al. Enhanced cellular secretion of AAV2 by expression of foreign viral envelope proteins. Biochemical Engineering Journal, vol. 93, Jan. 15, 2015, pp. 108-114.

Methods in Molecular Biology, ed. Richard, Humana Press, NJ (1995).

Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.

Darambazar G, et al. Paraventricular NUCB2/nesfatin-1 is directly targeted by leptin and mediates its anorexigenic effect. Biochem Biophys Res Commun Jan. 2015, 456(4):913-8.

He X, et al. Recombinant adeno-associated virus-mediated inhibition of microRNA-21 protects mice against the lethal schistosome infection by repressing both IL-13 and transforming growth factor beta 1 pathways. Hepatology. Jun. 2015, 61(6):2008-17. d.

Huang WD, et al. miR-134 Regulates Ischemia/Reperfusion Injury-Induced Neuronal Cell Death by Regulating CREB Signaling. J Mol Neurosci. Apr. 2015, 55(4):821-9.

Keiser MS et al. RNAi Prevents and Reverses Phenotypes Induced by Mutant Human Ataxin-1. Ann Neurol. Sep. 30, 2016.

Knabel MK, et al. Systemic Delivery of scAAV8-Encoded MiR-29a Ameliorates Hepatic Fibrosis in Carbon Tetrachloride-Treated Mice. PLoS One.Oct. 2014,10(4):e0124411.

Miyamoto Y, et al. Knockdown of Dopamine D-2 Receptors in the Nucleus Accumbens Core Suppresses Methamphetamine-Induced Behaviors and Signal Transduction in Mice. Int J Neuropsychopharmacol. Feb. 2015, 18(4).

Valdmanis PN, et al. RNA interference-induced hepatotoxicity results from loss of the first synthesized isoform of microRNA-122 in mice. Nat Med. May 2016;22(5):557-62.

Weinberg MS, et al. Viral Vector Reprogramming of Adult Resident Striatal Oligodendrocytes into Functional Neurons Mol Ther. Apr. 2017;25(4):928-934.

Xie J et al. Adeno-Associated Virus-Mediated MicroRNA Delivery and Therapeutics. Semin Liver Dis. Feb. 2015, 35(1):81-8.

Xu PW, et al. Estrogen receptor-alpha in medial amygdala neurons regulates body weight. J Clin Invest.Jul. 2015, 125(7):2861-76.

Keiser MS et al. Broad distribution of ataxin 1 silencing in rhesus cerebella for spinocerebellar ataxia type 1 therapy. Brain. Dec. 2015;138(Pt 12):3555-66.

Enomoto M, et al. Efficient Gene Suppression in Dorsal Root Ganglia and Spinal Cord Using Adeno-Associated Virus Vectors Encoding Short-Hairpin RNA. Methods Mol Biol. 2016;1364:77-90.

Tan AM, et al. Virus mediated knockdown of Nav1.3 in dorsal root ganglia of STZ-Induced diabetic rats alleviates tactile allodynia. Mol Med. Jun. 2015;21:544-52.

Chali F, et al. Inhibiting cholesterol degradation induces neuronal sclerosis and epileptic activity in mouse hippocampus. Eur J Neurosci. May 2015, 41(10):1345-55.

Fan D-S, et al. Behavioral Recovery in 6-Hydroxydopamine-Lesioned Rats by Contransduction of Striatum with Tyrosine Hydroxylase and Aromatic L-Amino Acid Decarboxylase Genes Using Two Separate Adeno-Associated Virus Vectors. Human Gene Therapy. Nov. 20, 1998; 9:2527-2535.

Herzog R, et al. Long-term correction of canine hemophilia B by gene transfer of blood coagulation factor IX mediated by adeno-associated viral vector. Nature Medicine. Jan. 1999; vol. 5 No. 1.

Jolesz F. Intraoperative Imaging in Neurosurgery: Where Will the Future Take Us?. Acta Nerochir Suppl. 2011:109:21-25.

Forsayeth J, et al. A Dose-Ranging Study of AAV-hAADC Therapy in Parkinsonian Monkeys. Mol Ther. Oct. 2006,14(4):571-577.

Hadaczek P, et al. Eight Years of Clinical Improvement in MPTP-Lesioned Primates After Gene Therapy With AAV2-hAADC. Molecular Therapy. Aug. 2010;vol. 18No. 8,1458-1461.

MacLullich A, et al. Enlarged perivascular spaces are associated with cognitive function in healthy elderly men. J Neurol Neurosurg Psychiatry. 2004;75:1519-1523.

Potter G, et al. Cerebral Perivascular Spaces Visible on Magnetic Resonance Imaging: Development of a Qualitative Rating Scale and its Observer Reliability. Cerebrovascular Diseases Mar. 19, 2015;39:224-231.

Potter G, et al. Enlarged perivascular spaces (EPVS): a visual rating scale and user guide. Guide prepared by Gillian Potter, Zoe Morris and Prof Joanna Wardlaw (University of Edinburgh).

Racette B, et al. [18F]FDOPA PET as an Endophenotype for Parkinson's Disease Linkage Studies. Am J Med Genet B Neuropsychiatr Genet. Apr. 5, 2006;141B(3):245-249.

Grimm D, et al. In Vitro and In Vivo Gene Therapy Vector Evolution via Multispecies Interbreeding and Retargeting of Adeno-Associated Viruses. Journal of Virology Jun. 2008;5887-5911.

Kern A, et al. Identification of a Heparin-Binding Motif on Adeno-Associated Virus Type 2 Capsids. Journal of Virology. Oct. 2003;11072-11081.

Voyager Therapeutics—Investors & Media—Press Release, Voyager Therapeutics Announces Positive Interim Results from Phase 1b Trial of VY-AADC01 for Advanced Parkinson's Disease, Dec. 7, 2016, pp. 1-6.

Sun J, et al. Gene delivery of activated Factor VII Using Alternative AAV Serotype Improves Hemostasis in Hemophiliac Mice with FVIII Inhibitors and AAV Neutralizing antibodies. Hum Gene Ther. May 6, 2017. Epub ahead of print.

Tse LV, et al. Structure-guided evolution of antigenically distinct adeno-associated virus variants for immune evasion. Proc Natl Acad Sci U S A. May 30, 2017 Epub ahead of print.

Vandamme C, et al. Unraveling the complex story of immune responses to AAV vectors trial after trial. Hum Gene Ther. Aug. 23, 2017.

Fu H, et al. Differential prevalence of antibodies against adeno-associated virus in healthy children and patients with mucopolysaccharidosis III: perspective for AAV-mediated gene therapy. Human Gene Ther Clin Dev Sep. 19, 2017 Epub ahead of print.

Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.

Majowicz A, et al. Successful Repeated Hepatic Gene Delivery in Mice and Non-human Primates Achieved by Sequential Administralion of AAV5ch and AAV1 Mol Ther. Jun. 5, 2017 Epub ahead of print.

Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.

Gil-Farina I, et al. Recombinant AAV Integration Is Not Associated With Hepatic Genotoxicity in Nonhuman Primates and Patients. Mol Ther. Jun. 2016;24(6):1100-5.

(56) References Cited

OTHER PUBLICATIONS

Logan GJ, et al. Identification of liver-specific enhancer-promoter activity in the 3' untranslated region of the wild-type AAV2 genome Nat Genet Jun. 19, 2017. Epub ahead of print.
Pillay S, et al. AAV serotypes have distinctive interactions with domains of the cellular receptor AAVR. J Virol. Jul. 5, 2017. Epub ahead of print.
Wang M, Sun J, Crosby A, Woodard K, Hirsch ML, Samulski RJ, Li C. Direct interaction of human serum proteins with AAV virions to enhance AAV transduction: immediate impact on clinical applications. Gene Ther. Jan. 2017;24(1):49-59. doi: 10.1038/gt.2016.75. Epub Nov. 11, 2016.
Bennett A, et al. Thermal Stability as a Determinant of AAV Serotype Identity. Mol Ther Methods Clin Dev. Jul. 24, 2017;6:171-182. doi: 10.1016/j.omtm.2017.07.003.
Gray-Edwards H, et al. AAV gene therapy in a sheep model of Tay-Sachs disease. Human Gene Therapy. Sep. 19, 2017 Epub ahead of print.
Guggino W, et al. A Preclinical Study in Rhesus Macaques for Cystic Fibrosis To Assess Gene Transfer and Transduction By AAV1 and AAV5 With a Dual-Luciferase Reporter System. Hum Gene Ther Clin Dev. Jul. 20, 2017.
Eichler F, et al. Hematopoietic Stem-Cell Gene Therapy for Cerebral Adrenoleukodystrophy. N Engl J Med Oct. 4, 2017 Epub ahead of print.
Bennett A, et al. Understanding capsid assembly and genome packaging for adeno-associated viruses. Future Virology Jun. 2017; 12(6): 283-297.
Grimm et al. Small but increasingly mightly—latest advances in AAV vector research, design and evolution. Hum Gene Ther. Nov. 2017 (Epub Aug. 23, 2017); 28(11):1075-1086.
Pillay S, et al. Host determinants of adeno-associated viral vector entry. Curr Opin Virol. Jun. 30, 2017;24:124-131. Epub ahead of print.
Smith LJ, et al. Gene transfer properties and structural modeling of human stem cell-derived AAV. Molecular Therapy. Sep. 2014;22(9)1625-1634.
Wooley DP, et al. A directed evolution approach to select for novel Adeno-associated virus capsids on an HIV-1 producer T cell line. J Virol. Methods. Sep. 13, 2017 Epub ahead of print.
Biferi MG, et al. A New AAV10-U7-Mediated Gene Therapy Prolongs Survival and Restores Function in an ALS Mouse Model. Mol Ther. Jun. 26, 2017 Epub ahead of print.
Li D, et al. Slow intrathecal injection of rAAVrh10 enhances its transduction of spinal cord and therapeutic efficacy in a mutant SOD1 model of ALS. Neuroscience Oct. 9, 2017 Epub ahead of print.
Eichler K, et al. The complete connectome of a learning and memory centre in an insect brain. Nature. Aug. 9, 2017;548(7666)175-182.
Le Pichon CE, et al. Loss of dual leucine zipper kinase signaling is protective in animal models of neurodegenerative disease. Sci Transl Med. Aug. 16, 2017;9(403).
Durost P, et al. Gene therapy with an AAV vector expressing human IL-2 alters immune system homeostasis in humanized mice. Hum Gene Ther. Aug. 21, 2017 Epub ahead of print.
Ahmad M, et al. Engineered Expression of Broadly Neutralizing Antibodies Against Human Immunodeficiency Virus. Annu Rev Virol. Jun. 23, 2017. Epub ahead of print.
Brady JM, et al. Antibody gene transfer with adeno-associated viral vectors as a method for HIV prevention. Immunol Rev. Jan. 2017;275(1):324-333 doi: 10.1111/imr.12478.
Magnani DM et al.. Dengue virus evades AAV-mediated neutralizing antibody prophylaxis in rhesus monkeys. Mol Ther Jul. 24, 2017 Epub ahead of print.
Zhu Z, et al. Zika virus has oncolytic activity against glioblastoma stem cells. J Exp Med. Sep. 5, 2017 Epub ahead of print.
Liu Z et al. Single cell transcriptomics reconstructs fate conversion from fibroblast to cardiomyocyte. Nature. Oct. 25, 2017 Epub ahead of print.

Kurosaki F, et al. Optimization of adeno-associated virus vector-mediated gene transfer to the respiratory tract. Gene Ther. May 2017;24(5):290-297.
Tadokoro T, et al. Subpial Adeno-associated Virus 9 (AAV9) Vector Delivery in Adult Mice. J Vis Exp. Jul. 13, 2017;(125). doi: 10.3791/55770.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc. 13861.
Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Gombash SE, et al. Systemic gene delivery transduces the enteric nervous system of guinea pigs and cynomolgus macaques. Gene Ther. Aug. 3, 2017. doi: 10.1038/gt.2017.72.
Hinderer C, et al. Evaluation of intrathecal routes of administration for adeno-associated virus vectors in large animals. Hum Gene Ther. Aug. 15, 2017. doi: 10.1089/hum.2017.026.
Hordeaux J, et al. Long-term neurologic and cardiac correction by intrathecal gene therapy in Pompe disease. Acta Neuropathol Commun Sep. 6, 2017(5):66.
Tardieu M, et al. Intracerebral gene therapy in children with mucopolysaccharidosis type IIIB syndrome: an uncontrolled phase 1/2 clinical trial. Lancet Neurol. Sep. 2017;16(9):712-720.
Yazdan-Shahmorad A, et al. Widespread Optogenetic Expression in Macaque Cortex Obtained with MR-Guided, Convection Enhanced Delivery (CED) of AAV vector to the Thalamus. J Neurosci Methods. Oct. 14, 2017 Epub ahead of print.
Lee NC, et al. A neuron-specific gene therapy relieves motor deficits in pompe disease mice. Mol Neurobiol. Sep. 11, 2017 Epub ahead of print.
Carvalho LS, et al. Evaluating efficiencies of dual AAV approaches for retinal targeting. Front Neursci. Sep. 8, 2017;11:503.
Reichel FF, et al. AAV8 can induce innate and adaptive immune response in the primate eye. Mol Ther. Aug. 31, 2017 Epub ahead of print.
De Silva SR, Charbel Issa P, Singh MS, Lipinski DM, Barnea-Cramer AO, Walker NJ, Barnard AR, Hankins MW, MacLaren RE. Single residue AAV capsid mutation improves transduction of photoreceptors in the Abca4$^{-/-}$ mouse and bipolar cells in the rd1 mouse and human retina ex vivo Gene Ther Nov. 2016;23(11):767-774. doi:10.1038/gt.2016.54. Epub Jul. 14, 2016.
Katz MG, et al. Use of Adeno-Associated Virus Vector for Cardiac Gene Delivery in Large Animal Surgical Models of Heart Failure Hum Gene Ther Clin Dev Jul. 20, 2017.
Watanabe S, et al. Protein Phosphatase Inhibitor-1 Gene Therapy in a Swine Model of Nonischemic Heart Failure. Journal of the American College of Cardiology 2017.
Iwamoto N, et al. Control of phosphorothioate stereochemistry substantially increases the efficacy of antisense oligonucleotides. Nat Biotechnol. Aug. 21, 2017.
Clift D, et al. A Method for the Acute and Rapid Degradation of Endogenous Proteins. Cell Nov. 16, 2017.
Boone DR, et al. Effects of AAV-mediated knockdown of nNOS and GPx-1 gene expression in rat hippocampus after traumatic brain injury. PLoS One. 2017 10;12(10):e0185943.
Jin X, et al. Direct LC/MS Analysis for Complete Characterization of Recombinant Adeno-Associated Virus Capsid Proteins. Hum Gene Ther Methods. Jun. 18, 2017. Epub ahead of print.
Galli A, et al. Strategies to optimize capsid protein expression and single stranded DNA formation of Adeno-associated virus in *Saccharomyces cerevisiae*. J Appl Microbiol. Jun. 13, 2017. Epub ahead of print.
Wang Z, et al. Human Bocavirus 1 Is a Novel Helper for Adeno-Associated Virus Replication. J Virol. Jun. 28, 2017. Epub ahead of print.
Grobe S, et al. Relevance of assembly-activating protein for Adeno-associated virus vector production and capsid protein stability in mammalian and insect cells. J Virol. Aug. 2, 2017. pii: JVI.01198-17. doi: 10.1128/JVI.01198-17.

(56) References Cited

OTHER PUBLICATIONS

Kondratov O, et al. Direct head-to-head evaluation of recombinant Adeno-associated viral (rAAV) vectors manufactured in human vs insect cells. Molecular Therapy Aug. 10, 2017.
Jungmann A, et al. Protocol for efficient generation and characterization of adeno-associated viral (AAV) vectors. Hum Gene Ther Methods Sep. 21, 2017 Epub ahead of print.
Luo Y, et al. AAVS1-Targeted Plasmid Integration in AAV Producer Cell Lines. Hum Gene Ther Methods. Jun. 2017;28(3):124-138.
Savy A, et al. Impact of ITR integrity on rAAV8 production using baculovirus/Sf9 cells system. Hum Gene Ther Methods. Oct. 1, 2017 Epub ahead of print.
GTEx Consortium et al. Genetic effects on gene expression across human tissues. Nature. Oct. 11, 2017;550(7675):204-213.
Li X, et al. The impact of rare variation on gene expression across tissues. Nature. Oct. 11, 2017;550(7675):239-243.
Ojala DS, et al. In Vivo Selection of a Computationally Designed Schema AAV Library Yields a Novel Variant for Infection of Adult Neural Stem Cells in the SVZ. Mol Ther. Sep. 8, 2017 Epub ahead of print.
Chandran JS, et al. Site Specific Modification of Adeno-Associated Virus Enables Both Fluorescent Imaging of Viral Particles and Characterization of the Capsid Interactome. Sci Rep. Nov. 7, 2017;7(1):14766.
Chai Z, et al. Application of polyploid adeno-associated virus vectors for transduction enhancement and neutralizing antibody evasion. J Control Release. Aug. 5, 2017 pii: S0168-3659(17)30772-1. doi: 10.1016/j.jconrel.2017.08.005.
Hickey DG, et al. Tropism of engineered and evolved recombinant AAV serotypes in the rd1 mouse and ex vivo primate retina Gene Ther: Sep. 5, 2017 Epub ahead of print.
Yan Z, et al. Human Bocavirus Type-1 Capsid Facilitates the Transduction of Ferret Airways by Adeno-Associated Virus Genomes Hum Gene Ther. May 10, 2017. Epub ahead of print.
Kanaan NM, et al. Rationally Engineered AAV Capsids Improve Transduction and Volumetric Spread in the CNS. Molecular Therapy-Nucleic Acids 8: 184-197 Sep. 15, 2017.
Powell SK, Khan N, Parker CL, Samulski RJ, Matsushima G, Gray SJ, McCown TJ. Characterization of a novel adeno-associated viral vector with preferential oligodendrocyte tropism. Gene Ther. Nov. 2016;23(11):807-814. doi: 10.1038/gt.2016.62. Epub Sep. 15, 2016.
Kanaan N, et al. Rationally Engineered AAV Capsids Improve Transduction and Volumetric Spread in the CNS. Molecular Therapy—Nucleic Acids, vol. 8 , 184-197.
Chan KY, et al. Engineered AAVs for efficient noninvasive gene delivery to the central and peripheral nervous systems. Nat Neurosci. Jun. 26, 2017. Epub ahead of print.
Paulk NK, et al. Bioengineered AAV Capsids with Combined High Human Liver Transduction In Vivo and Unique Humoral Seroreactivity. Mol Ther. Sep. 25, 2017 Epub ahead of print.
Hagedorn C, et al. S/MAR element facilitates episomal long-term persistence of Adeno-associated viral (AAV) vector genomes in proliferating cells. Hum Gene Ther. Jun. 30, 2017. Epub ahead of print.
Ziegler T, et al. Steerable induction of the Thymosin β4/MRTF-A pathway via AAV-based overexpression induces therapeutic neovascularization. Hum Gene Ther. Jul. 20, 2017.
Potter RA, et al. Systemic Delivery of Dysferlin Overlap Vectors Provides Long-Term Functional Improvement for Dysferlinopathy. Hum Gene Ther. Jul. 14, 2017 Epub ahead of print.
Huang W, et al. Targeting Visceral Fat by Intraperitoneal Delivery of Novel AAV Serotype Vector Restricting Off-Target Transduction in Liver. Mol Ther Methods Clin Dev. Jun. 19, 2017;6:68-78.
Herrera-Carrillo E, et al. Improving miRNA delivery by optimizing miRNA expression cassettes in viral vectors. Hum Gene Ther Methods. Jul. 16, 2017.
Carter BJ. Adeno-associated virus and the development of adeno-associated virus vectors: a historical perspective. Mol Ther. Dec. 2004;10(6):981-9.

G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2): 1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing Nat Commun 2014;5:3075. doi: 10.1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. SIAM J. Appl. Math. 48-5 (1988), pp. 1073-1082.
Devereux J A comprehensive set of sequence analysis programs for the VAX. Nucleic Acids Res. Jan. 11, 1984; 12(1 Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge SM Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.

(56) References Cited

OTHER PUBLICATIONS

Chandler RJ, et al. Systemic AAV9 gene therapy improves the lifespan of mice with Niemann-Pick disease, type C1. Hum Mol Genet. Jan. 2017;26(1):52-64.

Dang CH, et al. In vivo dynamics of AAV-mediated gene delivery to sensory neurons of the trigeminal ganglia. Sci Rep. Apr. 19, 2017;7(1):927.

Dimidschstein J, et al. A viral strategy for targeting and manipulating interneurons across vertebrate species. Nat Neurosci. Dec. 2016;19(12):1743-1749.

Donsante A et al. Intracerebroventricular delivery of self-complementary adeno-associated virus serotype 9 to the adult rat brain. Gene Ther. May 2016;23(5):401-7.

El-Shamayleh Y, et al. Strategies for targeting primate neural circuits with viral vectors. J Neurophysiol. Jul. 2016;116(1):122-34.

Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.

Gessler DJ et al. Gene Therapy for the Treatment of Neurological Disorders: Metabolic Disorders. Methods Mol Biol. 2016;1382:429-65.

Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.

Gombash SE, et al. Systemic Gene Therapy for Targeting the CNS. Methods Mol Biol. 2016;1382:231-7.

Gurda BL, et al. Evaluation of AAV-mediated gene therapy for central nervous system disease in canine mucopolysaccharidosis VII. Mol Ther. Feb. 2016;24(2):206-16.

Ahmed SS, et al. rAAV gene therapy in a Canavan's disease mouse model reveals immune impairments and an extended pathology beyond the central nervous system. Mol Ther. Jun. 2016;24(6):1030-41.

Dashkoff J, et al. Tailored transgene expression to specific cell types in the central nervous system after peripheral injection with AAV9. Mol Ther Methods Clin Dev. Dec. 2016;3:16081.

Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.

Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.

Greig JA, et al. Impact of intravenous infusion time on AAV8 vector pharmacokinetics, safety, and liver transduction in cynomolgus macaques. Mol Ther Methods Clin Dev. Dec. 2016;3:16079.

Gruntman AM, et al. Delivery of Adeno-associated virus gene therapy by intravascular limb infusion methods. Hum Gene Ther Clin Dev Sep. 2015;26(3):159-64.

Hagg A, et al. Using AAV vectors expressing the beta 2-adrenoceptor or associated G alpha proteins to modulate skeletal muscle mass and muscle fiber size. Sci Rep. Mar. 2016;6:23042.

Greig JA, et al. Intramuscular administration of AAV overcomes pre-existing neutralizing antibodies in rhesus macaques. Vaccine. Dec. 2016;34(50):6323-6329.

Ai J, et al. Adeno-associated virus serotype rh.10 displays strong muscle tropism following intraperitoneal delivery. Sci Rep. Jan. 2017;7:40336.

Baum BJ, et al. Advances in salivary gland gene therapy—oral and systemic implications. Expert Opinion on Biologica Therapy. 2015;15(10):1443-54.

Hai B, et al. Long-term transduction of miniature pig parotid glands using serotype 2 adeno-associated viral vectors. J Gene Med. Jun. 2009;11(6):506-14.

\* cited by examiner

MODULATORY POLYNUCLEOTIDES

CROSS REFERENCE TO RELATED APPLICATIONS

This application is a continuation application which claims the benefit of U.S. patent application Ser. No. 16/302,146, filed Nov. 16, 2018 and entitled Modulatory Polynucleotides; which is a national stage filing under 35 U.S.C. § 371 of International Application No. PCT/US2017/033268, filed May 18, 2017 and entitled Modulatory Polynucleotides; which claims priority to US Provisional Patent Application No. 62/338,137, filed on May 18, 2016, entitled Modulatory Polynucleotides, and US Provisional Patent Application No. 62/485,050, filed on Apr. 13, 2017, entitled Modulatory Polynucleotides, the contents each of which are herein incorporated by reference in their entireties.

REFERENCE TO THE SEQUENCE LISTING

The present application is being filed along with a Sequence Listing in electronic format. The Sequence Listing is provided as a file entitled 20571039USCONSL.txt, created on Jan. 22, 2020, which is 4,262,116 bytes in size. The information in the electronic format of the sequence listing is incorporated herein by reference in its entirety.

FIELD OF THE INVENTION

The invention relates to compositions, methods, processes, kits and devices for the design, preparation, manufacture and/or formulation of modulatory polynucleotides. In some embodiments such modulatory polynucleotides may be encoded by or within recombinant adeno-associated viruses (AAV) and may comprise artificial microRNAs, artificial pre-microRNAs and/or artificial pri-microRNAs.

BACKGROUND OF THE INVENTION

MicroRNAs (or miRNAs or miRs) are small, non-coding, single stranded ribonucleic acid molecules (RNAs), which are usually 19-25 nucleotides in length. More than a thousand microRNAs have been identified in mammalian genomes. The mature microRNAs primarily bind to the 3' untranslated region (3'-UTR) of target messenger RNAs (mRNAs) through partially or fully pairing with the complementary sequences of target mRNAs, promoting the degradation of target mRNAs at a post-transcriptional level, and in some cases, inhibiting the initiation of translation. MicroRNAs play a critical role in many key biological processes, such as the regulation of cell cycle and growth, apoptosis, cell proliferation and tissue development.

miRNA genes are generally transcribed as long primary transcripts of miRNAs (i.e. pri-miRNAs). The pri-miRNA is cleaved into a precursor of a miRNA (i.e. pre-miRNA) which is further processed to generate the mature and functional miRNA.

While many target expression strategies employ nucleic acid based modalities, there remains a need for improved nucleic acid modalities which have higher specificity and with fewer off target effects.

The present invention provides such improved modalities in the form of artificial pri-, pre- and mature microRNA constructs and methods of their design. These novel constructs may be synthetic stand-alone molecules or be encoded in a plasmid or expression vector for delivery to cells. Such vectors include, but are not limited to adeno-associated viral vectors such as vector genomes of any of the AAV serotypes or other viral delivery vehicles such as lentivirus, etc.

SUMMARY OF THE INVENTION

Described herein are compositions, methods, processes, kits and devices for the design, preparation, manufacture and/or formulation of modulatory polynucleotides.

In some embodiments such modulatory polynucleotides may be encoded by or contained within plasmids or vectors or recombinant adeno-associated viruses (AAV) and may comprise artificial microRNAs, artificial pre-microRNAs and/or artificial pri-microRNAs.

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 1 discloses SEQ ID NO: 943.

DETAILED DESCRIPTION

I. Compositions of the Invention

Modulatory Polynucleotides

Figure 1:
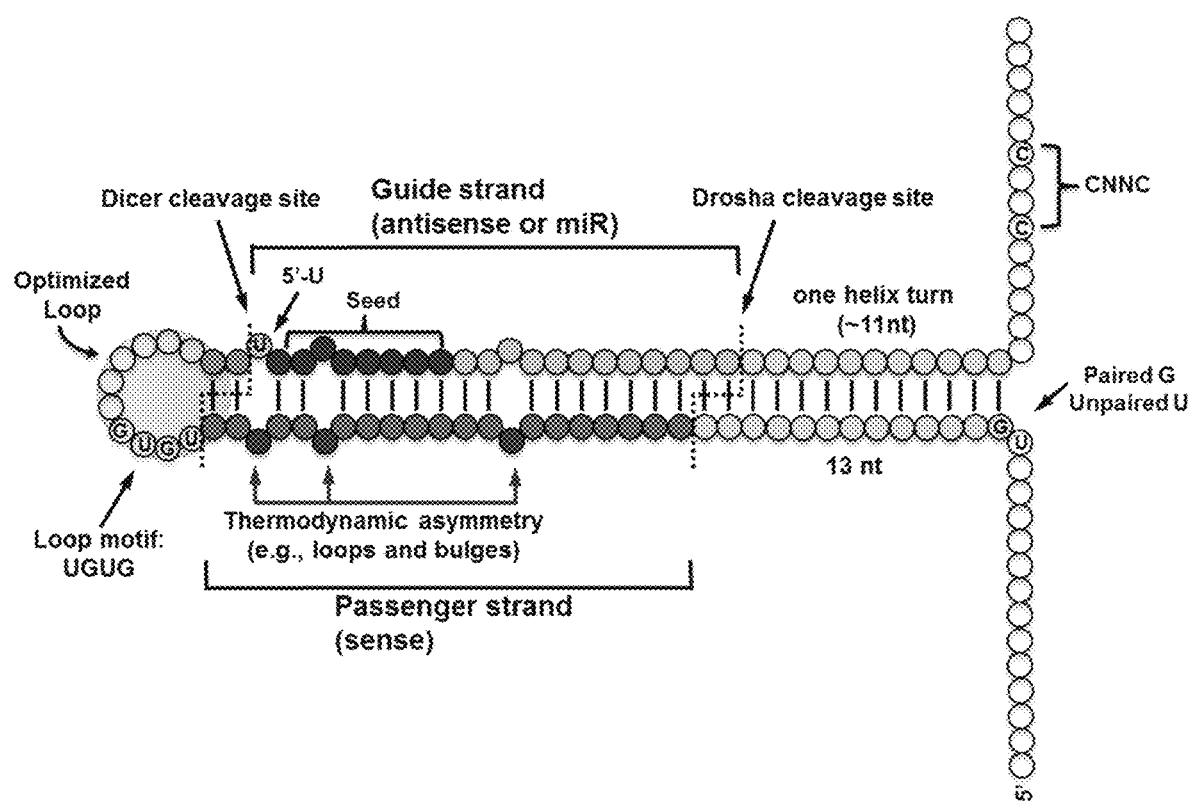
FIG. 1 is a schematic of an artificial pri-microRNA that is part of a viral genome packaged in an AAV vector according to the present invention.

According to the present invention, modulatory polynucleotides are provided which function as artificial microRNAs. As used herein a "modulatory polynucleotide" is any nucleic acid polymer which functions to modulate (either increase or decrease) the level or amount of a target gene. Modulatory polynucleotides include precursor molecules which are processed inside the cell prior to modulation. Modulatory polynucleotides or the processed forms thereof may be encoded in a plasmid, vector, genome or other nucleic acid expression vector for delivery to a cell.

In one embodiment, the modulatory polynucleotides may comprise at least one nucleic acid sequence encoding at least one siRNA molecule. The nucleic acids may, independently if there is more than one, encode 1, 2, 3, 4, 5, 6, 7, 8, 9, or more than 9 siRNA molecules.

In some embodiments modulatory polynucleotides are designed as primary microRNA (pri-miRs) or precursor microRNAs (pre-miRs) which are processed within the cell to produce highly specific artificial microRNAs.

The modulatory polynucleotides, especially the artificial microRNAs of the invention, may be designed based on the sequence or structure scaffold of a canonical or known microRNA, pri-microRNA or pre-microRNA. Such sequences may correspond to any known microRNA or its precursor such as those taught in US Publication US2005/

0261218 and US Publication US2005/0059005, the contents of which are incorporated herein by reference in their entirety.

microRNAs (or miRNA or miRs) are 19-25 nucleotide long noncoding RNAs that bind to the 3'UTR of nucleic acid molecules and down-regulate gene expression either by reducing nucleic acid molecule stability or by inhibiting translation. The modulatory polynucleotides of the invention may comprise one or more microRNA sequences, microRNA seeds or artificial microRNAs, e.g., sequences which function as a microRNA.

A microRNA sequence comprises a "seed" region, i.e., a sequence in the region of positions 2-9 of the mature microRNA, which sequence has perfect Watson-Crick complementarity to the miRNA target sequence. A microRNA seed may comprise positions 2-8 or 2-7 or 2-9 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh KK, Johnston WK, Garrett-Engele P, Lim L P, Bartel D P; Mol Cell. 2007 Jul. 6; 27(1):91-105; each of which is herein incorporated by reference in their entirety. In naturally occurring microRNA, the bases of the microRNA seed have complete complementarity with the target sequence.

As taught herein, design parameters, or rules, have been identified and applied to design modulatory polynucleotides (e.g., artificial microRNAs) which have superior target gene modulatory properties with limited off target effects.

In one embodiment, the molecular scaffold of the modulatory polynucleotide described herein may be designed and optimized to create a modulatory polynucleotide that has the desired target gene modulatory properties. As a non-limiting example, the modulatory polynucleotide can have superior target gene modulatory properties with limited off target effects.

In one embodiment, the modulatory polynucleotides of the invention, such as artificial miRs, are comprised of modular elements or sequence motifs assembled according to a set of rules that result in highly specific target recognition and low guide/passenger ratio. Such modules or sequence motifs include, but are not limited to, double stranded regions, flanking regions, loops, optimized loops, UGUG loops, GU domains, spacers (to control proximal and distal motif or module spacing or to introduce structural elements such as turns, loops or bulges), CNNC motifs, and thermodynamic asymmetry regions which may embrace loops, bulges, mismatches, wobbles, and/or combinations thereof. Non limiting examples of rules which may be applied alone or in combination when constructing artificial miRs include those taught in Seitz et al. *Silence* 2011, 2:4; Gu, et al., *Cell* 151, 900-911, Nov. 9, 2012; Schwartz, et al., *Cell, Vol.* 115, 199-208, Oct. 17, 2003; Park, et al., *Nature, Vol.* 475, 101, 14 Jul. 2011; Ketley et al., 2013, *PLoS ONE* 8(6); Liu, et al., *Nucleic Acids Research,* 2008, Vol. 36, No. 9 2811-2824; Dow, et al., 2013, Nat Protoc.; 7(2): 374-393. doi:10.1038/nprot.2011.446; Auyeung, et al., *Cell* 152, 844-858, Feb. 14, 2013; Gu et al., *Cell* 2012 Nov. 9, 151(4): 900-11; Fellmann et al. Molecular Cell 41, 733-746, 2011; Han et al. Cell 125, 887-907, 2006; Betancur et al. Frontiers in Genetics, Vol. 3, Art. 127, 1-6 Jul. 2012; Schwarz et al. Cell Vol 115, 199-208, 2003; the contents of each of which are herein incorporated by reference in their entirety.

In one embodiment, any of the known RNAi constructs or RNAi agents may serve as the starting construct for the design of the passenger and/or guide strand of a modulatory polynucleotides or artificial microRNAs of the invention. These include canonical siRNAs, small interfering RNAs (siRNA), double stranded RNAs (dsRNAs), inverted repeats, short hairpin RNAs (shRNAs), small temporally regulated RNAs (stRNA), clustered inhibitory RNAs (cRNAs), including radial clustered inhibitory RNA, asymmetric clustered inhibitory RNA, linear clustered inhibitory RNA, and complex or compound clustered inhibitory RNA, dicer substrates, DNA-directed RNAi (ddRNAi), single-stranded RNAi (ssRNAi), microRNA (miRNA) antagonists, microRNA mimics, microRNA agonists, blockmirs (a.k.a. Xmirs), microRNA mimetics, microRNA addbacks, supermiRs, the oligomeric constructs disclosed in PCT Publication WO/2005/013901 the contents of which are incorporated herein in their entirety, tripartite RNAi constructs such as those disclosed in US Publication 20090131360, the contents of which are incorporated herein in their entirety, the solo-rxRNA constructs disclosed in PCT Publication WO/2010/011346, the contents of which are incorporated herein by reference in their entirety; the sd-rxRNA constructs disclosed in PCT Publication WO/2010/033247 the contents of which are incorporated herein by reference in their entirety, dual acting RNAi constructs which reduce RNA levels and also modulate the immune response as disclosed in PCT Publications WO/2010/002851 and WO/2009/141146 the contents of which are incorporated herein by reference in their entirety and antigene RNAs (agRNA) or small activating RNAs (saRNAs) which increase expression of the target to which they are designed disclosed in PCT Publications WO/2006/130201, WO/2007/086990, WO/2009/046397, WO/2009/149182, WO/2009/086428 the contents of which are incorporated herein by reference in their entirety.

Likewise, any pri- or pre-microRNA precursor of the above listed microRNA may also serve as the molecular scaffold of the modulatory polynucleotides of the invention.

In one embodiment, the starting construct may be derived from any relevant species such as, not limited to, mouse, rat, dog, monkey or human.

In one embodiment, the modulatory polynucleotide may be located in an expression vector downstream of a promoter such as, but not limited to, CMV, U6, H1, CBA or a CBA promoter with a SV40 or a human betaGlobin intron. Further, the modulatory polynucleotide may also be located upstream of the polyadenylation sequence in an expression vector. As a non-limiting example, the modulatory polynucleotide may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the modulatory polynucleotide may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the modulatory polynucleotide may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the modulatory polynucleotide may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the modulatory polynucleotide may be located upstream of the polyadenylation sequence in an expression vector. Further, the modulatory polynucleotide may be located downstream of a promoter such as, but not limited to, CMV, U6, H1, CBA or a CBA promoter with a SV40 or a human betaGlobin intron in an expression vector. As a non-limiting example, the modulatory polynucleotide may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the modulatory polynucleotide may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the modulatory polynucleotide may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the modulatory polynucleotide may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the modulatory polynucleotide may be located in a scAAV.

In one embodiment, the modulatory polynucleotide may be located in an ssAAV.

In one embodiment, the modulatory polynucleotide may be located near the 5' end of the flip ITR in an expression vector. In another embodiment, the modulatory polynucleotide may be located near the 3'end of the flip ITR in an expression vector. In yet another embodiment, the modulatory polynucleotide may be located near the 5' end of the flop ITR in an expression vector. In yet another embodiment, the modulatory polynucleotide may be located near the 3' end of the flop ITR in an expression vector. In one embodiment, the modulatory polynucleotide may be located between the 5' end of the flip ITR and the 3' end of the flop ITR in an expression vector. In one embodiment, the modulatory polynucleotide may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the modulatory polynucleotide may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the modulatory polynucleotide may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the modulatory polynucleotide may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the modulatory polynucleotide may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the modulatory polynucleotide may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the modulatory polynucleotide may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25°A downstream from the 5' or 3' end of an ITR (e.g., Flip or Flop ITR) in an expression vector.

In addition to the modules or sequence motifs, modulatory polynucleotides comprise at least one of or both a passenger and guide strand. The passenger and guide strand may be positioned or located on the 5' arm or 3' arm of a stem loop structure of the modulatory polynucleotide.

In one embodiment, the 3' stem arm of the modulatory polynucleotides may have 11 nucleotides downstream of the 3' end of the guide strand which have complementarity to the 11 of the 13 nucleotides upstream of the 5' end of the passenger strand in the 5' stem arm.

In one embodiment, the modulatory polynucleotides may have a cysteine which is 6 nucleotides downstream of the 3' end of the 3' stem arm of the modulatory polynucleotide.

In one embodiment, the modulatory polynucleotides comprise a miRNA seed match for the guide strand. In another embodiment, the modulatory polynucleotides comprise a miRNA seed match for the passenger strand. In yet another embodiment, the modulatory polynucleotides do no comprise a seed match for the guide or passenger strand.

In one embodiment, the modulatory polynucleotides may have almost no significant full-length off targets for the guide strand. In another embodiment, the modulatory polynucleotides may have almost no significant full-length off targets for the passenger strand. In yet another embodiment, the modulatory polynucleotides may have almost no significant full-length off targets for the guide strand or the passenger strand.

In one embodiment, the modulatory polynucleotides may have high activity in vitro. In another embodiment, the modulatory polynucleotides may have low activity in vitro. In yet another embodiment, the modulatory polynucleotides may have high guide strand activity and low passenger strand activity in vitro.

In one embodiment, the modulatory polynucleotides have a high guide strand activity and low passenger strand activity in vitro. The target knock-down (KD) by the guide strand may be at least 60%, 65%, 70%, 75%, 80%, 85%, 90%, 95%, 99%, 99.5% or 100%. The target knock-down by the guide strand may be 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%.

In one embodiment, the IC50 of the passenger strand for the nearest off target is greater than 100 multiplied by the IC50 of the guide strand for the target. As a non-limiting example, if the IC50 of the passenger strand for the nearest off target is greater than 100 multiplied by the IC50 of the guide strand for the target then the modulatory polynucleotide is said to have high guide strand activity and a low passenger strand activity in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo.

In one embodiment, the guide-to-passenger (G:P) strand ratio is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo.

The guide to passenger ratio refers to the ratio of the guide strands to the passenger strands after the excision of the guide strand. For example, a 80:20 guide to passenger ratio would have 8 guide strands to every 2 passenger strands clipped out of the precursor. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In one embodiment, the guide to passenger (G:P) (also referred to as the antisense to sense) strand ratio expressed is greater than 1.

In one embodiment, the guide to passenger (G:P) (also referred to as the antisense to sense) strand ratio expressed is greater than 2.

In one embodiment, the guide to passenger (G:P) (also referred to as the antisense to sense) strand ratio expressed is greater than 5.

In one embodiment, the guide to passenger (G:P) (also referred to as the antisense to sense) strand ratio expressed is greater than 10.

In one embodiment, the guide to passenger (G:P) (also referred to as the antisense to sense) strand ratio expressed is greater than 20.

In one embodiment, the guide to passenger (G:P) (also referred to as the antisense to sense) strand ratio expressed is greater than 50.

In one embodiment, the guide to passenger (G:P) (also referred to as the antisense to sense) strand ratio expressed is at least 3:1.

In one embodiment, the guide to passenger (G:P) (also referred to as the antisense to sense) strand ratio expressed is at least 5:1.

In one embodiment, the guide to passenger (G:P) (also referred to as the antisense to sense) strand ratio expressed is at least 10:1.

In one embodiment, the guide to passenger (G:P) (also referred to as the antisense to sense) strand ratio expressed is at least 20:1.

In one embodiment, the guide to passenger (G:P) (also referred to as the antisense to sense) strand ratio expressed is at least 50:1.

In one embodiment, the passenger to guide (P:G) (also referred to as the sense to antisense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the excision of the guide strand. For example, a 80:20 passenger to guide ratio would have 8 passenger strands to every 2 guide strands clipped out of the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In one embodiment, the passenger to guide (P:G) (also referred to as the sense to antisense) strand ratio expressed is greater than 1.

In one embodiment, the passenger to guide (P:G) (also referred to as the sense to antisense) strand ratio expressed is greater than 2.

In one embodiment, the passenger to guide (P:G) (also referred to as the sense to antisense) strand ratio expressed is greater than 5.

In one embodiment, the passenger to guide (P:G) (also referred to as the sense to antisense) strand ratio expressed is greater than 10.

In one embodiment, the passenger to guide (P:G) (also referred to as the sense to antisense) strand ratio expressed is greater than 20.

In one embodiment, the passenger to guide (P:G) (also referred to as the sense to antisense) strand ratio expressed is greater than 50.

In one embodiment, the passenger to guide (P:G) (also referred to as the sense to antisense) strand ratio expressed is at least 3:1.

In one embodiment, the passenger to guide (P:G) (also referred to as the sense to antisense) strand ratio expressed is at least 5:1.

In one embodiment, the passenger to guide (P:G) (also referred to as the sense to antisense) strand ratio expressed is at least 10:1.

In one embodiment, the passenger to guide (P:G) (also referred to as the sense to antisense) strand ratio expressed is at least 20:1.

In one embodiment, the passenger to guide (P:G) (also referred to as the sense to antisense) strand ratio expressed is at least 50:1.

In one embodiment, a passenger-guide strand duplex is considered effective when the pri- or pre-microRNAs demonstrate, but methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the integrity of the vector genome is at least 60%, 65%, 70%, 75%, 80%, 85%, 90%, 95%, 99% or more than 99% of the full length of the construct.

Target Nucleic Acids

The modulatory polynucleotides of the invention may be targeted to any gene or nucleic acid construct including coding and non-coding genes. Genes (DNA or mRNA) that encode human or primate proteins may be targeted. Further, non-coding genes may also be targeted, e.g., long noncoding RNAs (lncRNA).

Examples of such lncRNA molecules and RNAi constructs designed to target such lncRNA any of which may be targeted by or encoded in the modulatory polynucleotides, respectively are taught in International Publication, WO2012/018881 A2, the contents of which are incorporated herein by reference in their entirety.

In one embodiment, the modulatory polynucleotides of the invention may target any gene known in the art. As a non-limiting example, the gene may be SOD1.

In one embodiment, the modulatory polynucleotides of the invention may target any gene known in the art. As a non-limiting example, the gene may be Htt.

In one embodiment, the modulatory polynucleotide may be designed to target any gene or mRNA in the human genome, e.g., genes associated with CNS disorders such as, but not limited to, Huntington's Disease, ALS and the like.

Molecular Scaffolds

In some embodiments the starting molecular scaffold of the modulatory polynucleotide is a known or wild type pri- or pre-microRNA. In other embodiments the molecular scaffold of the modulatory polynucleotides is designed ab initio. (See Cullen, Gene Therapy (2006) 13, 503-508 work with miR30; Chung, et al., Nucleic Acids Research, 2006, Vol. 34, No. 7 working with miR-155; the contents of which are herein incorporated by reference in their entirety).

As used herein a "molecular scaffold" is a framework or starting molecule that forms the sequence or structural basis against which to design or make a subsequent molecule.

The modulatory polynucleotides of the present invention may be designed as a pri-miR as shown in FIG. 1. In the figure, a pri-miR molecular scaffold is shown. The modulatory polynucleotide which comprises the payload (e.g., siRNA, miRNA or other RNAi agent described herein) comprises a leading 5' flanking sequence which may be of any length and may be derived in whole or in part from wild type microRNA sequence or be completely artificial.

In one embodiment, the molecular scaffold comprises at least one 5' flanking region. As a non-limiting example, the 5' flanking region may comprise a 5' flanking sequence which may be of any length and may be derived in whole or in part from wild type microRNA sequence or be a completely artificial sequence.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

In one embodiment, the molecular scaffold comprises at least one loop motif region. As a non-limiting example, the loop motif region may comprise a sequence which may be of any length.

In one embodiment, the molecular scaffold comprises a 5' flanking region, a loop motif region and/or a 3' flanking region.

In one embodiment, at least one payload (e.g., siRNA, miRNA or other RNAi agent described herein) may be encoded by a modulatory polynucleotide which may also comprise at least one molecular scaffold. The molecular scaffold may comprise a 5' flanking sequence and/or a 3' flanking sequence which may be of any length and may be derived in whole or in part from wild type microRNA sequence or be completely artificial. The 3' flanking sequence may mirror the 5' flanking sequence in size and origin. Either flanking sequence may be absent. The 3' flanking sequence may optionally contain one or more CNNC motifs, where "N" represents any nucleotide.

Forming the stem of the stem loop structure shown is a minimum of the modulatory polynucleotide encoding at least one payload sequence. In some embodiments the payload sequence comprises at least one nucleic acid sequence which is in part complementary or will hybridize to a target sequence. In some embodiments the payload is a wild type microRNA. In some embodiments the payload is an siRNA molecule or fragment of an siRNA molecule. In some embodiments the payload is a substantially double stranded construct which may comprise one or more microRNAs, artificial microRNAs or siRNAs.

In some embodiments, the 5' arm of the stem loop of the modulatory polynucleotide comprises a nucleic acid sequence encoding a passenger strand. This strand is also known as the sense strand in that it reflects an identity to a target. The passenger strand may be between 15-30 nucleotides in length. It may be 15, 16, 17, 18, 19, 20, 21, 22, 23, 24, 25, 26, 27, 28, 29 or 30 nucleotides in length.

In some embodiments, the 3' arm of the stem loop of the modulatory polynucleotide comprises a nucleic acid sequence encoding a guide strand. This strand is also known as the antisense strand in that it reflects homology to a target. The guide strand may be between 15-30 nucleotides in length, 21-25 nucleotides or 22 nucleotides in length. It may be 15, 16, 17, 18, 19, 20, 21, 22, 23, 24, 25, 26, 27, 28, 29 or 30 nucleotides in length. The guide strand, in some instances, comprises a "G" nucleotide at the 5' most end.

In some embodiments, where the guide strand comprises a microRNA, or artificial microRNAs, the guide strand may comprise one or more microRNA seed sequences. The seed sequence may be located at positions 2-7, 2-8 or 2-9 of the guide strand relative to the first 5' nucleotide of the guide strand or relative to a dicer cleavage site.

In other embodiments, the passenger strand may reside on the 3' arm while the guide strand resides on the 5' arm of the stem of the stem loop structure of the modulatory polynucleotide.

The passenger and guide strands may be completely complementary across a substantial portion of their length.

In other embodiments the passenger strand and guide strand may be at least 70, 80, 90, 95 or 99% complementary across independently at least 50, 60, 70, 80, 85, 90, 95, or 99% of the length of the strands.

Neither the identity of the passenger strand nor the homology of the guide strand need be 100% complementary to the target sequence.

In one embodiment, separating the passenger and guide strand of the stem loop structure of the modulatory polynucleotide is a loop sequence (also known as a loop motif, linker or linker motif). The loop sequence may be of any length, between 4-30 nucleotides, between 4-20 nucleotides, between 4-15 nucleotides, between 5-15 nucleotides, between 6-12 nucleotides, 6 nucleotides, 7, nucleotides, 8 nucleotides, 9 nucleotides, 10 nucleotides, 11 nucleotides, 12 nucleotides, 13 nucleotides, 14 nucleotides, and/or 15 nucleotides.

In some embodiments the loop sequence comprises a nucleic acid sequence encoding at least one UGUG motif. In some embodiments, the nucleic acid sequence encoding the UGUG motif is located at the 5' terminus of the loop sequence.

In one embodiment, spacer regions may be present in the modulatory polynucleotide to separate one or more modules (e.g., 5' flanking region, loop motif region, 3' flanking region, sense sequences, antisense sequence) from one another. There may be one or more such spacer regions present.

In one embodiment a spacer region of between 8-20, i.e., 8, 9, 10, 11, 12, 13, 14, 15, 16, 17, 18, 19, or 20 nucleotides may be present between the passenger strand and a flanking region sequence.

In one embodiment, the length of the spacer region is 13 nucleotides and is located between the 5' terminus of the passenger strand and the 3' terminus of the flanking sequence. In one embodiment a spacer is of sufficient length to form approximately one helical turn of the sequence.

In one embodiment a spacer region of between 8-20, i.e., 8, 9, 10, 11, 12, 13, 14, 15, 16, 17, 18, 19, or 20 nucleotides may be present between the guide strand and a flanking sequence.

In one embodiment, the spacer sequence is between 10-13, i.e., 10, 11, 12 or 13 nucleotides and is located between the 3' terminus of the guide strand and the 5' terminus of a flanking sequence. In one embodiment a spacer is of sufficient length to form approximately one helical turn of the sequence.

In one embodiment the modulatory polynucleotide comprises at least one UG motif at the base of the stem whereby the G nucleotide is paired and the U nucleotide is unpaired. In some embodiments the unpaired U nucleotide is located in a flanking sequence.

In one embodiment, the modulatory polynucleotide comprises in the 5' to 3' direction, a 5' flanking sequence, a 5' arm, a loop motif, a 3' arm and a 3' flanking sequence. As a non-limiting example, the 5' arm may comprise a passenger strand and the 3' arm comprises the guide strand. In another non-limiting example, the 5' arm comprises the guide strand and the 3' arm comprises the passenger strand.

In one embodiment, the 5' arm, payload (e.g., passenger and/or guide strand), loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the passenger strand sequence may be altered (e.g., substituting 1 or more nucleotides, adding nucleotides and/or deleting nucleotides). As a non-limiting example, the passenger strand sequence may comprise 1 or 2 substitutions within the last 4 nucleotides of the sequence (e.g., C substituted for a G). As another non-limiting example, the passenger strand sequence may comprise 1 or 2 substitutions within the 7-15 nucleotides from the 5'end of the sequence (e.g., U substituted for an A or C substituted for a G).

In one embodiment, the 3' arm strand sequence may be altered (e.g., substituting 1 or more nucleotides, adding nucleotides and/or deleting nucleotides). As a non-limiting example, the sequence of the 3' arm may comprise 1 or 2 substitutions within the first 4 nucleotides of the sequence (e.g., A substituted for a U).

In one embodiment, the molecular scaffold of the payload construct may comprise a 5' flanking region, a loop motif and a 3' flanking region. Between the 5' flanking region and the loop motif may be a first payload region and between the loop motif and the 3' flanking region may be a second payload region. The first and second payload regions may comprise siRNA, miRNA or other RNAi agents, fragments or variants described herein. The first and second payload regions may also comprise a sequence which is the same, different or complementary to each other. As a non-limiting example, the first payload region sequence may be a passenger strand of a siRNA construct and the second payload region sequence may be a guide strand of an siRNA construct. The passenger and guide sequences may be substantially complementary to each other. As another non-limiting example, the first payload region sequence may be a guide strand of a siRNA construct and the second payload region sequence may be a passenger strand of an siRNA construct. The passenger and guide sequences may be substantially complementary to each other.

In one embodiment, the molecular scaffold of the modulatory polynucleotides described herein may comprise a 5' flanking region, a loop motif region and a 3' flanking region. Non-limiting examples of the sequences for the 5' flanking region, loop motif region and the 3' flanking region which may be encoded by the modulatory polynucleotide described herein are shown in Tables 1-3.

TABLE 1

5' Flanking Regions for Molecular Scaffold

| 5' Flanking Region Name | 5' Flanking Region Sequence | 5' Flanking Region SEQ ID NO |
|---|---|---|
| 5F1 | UUUAUGCCUCAUCCUCUGAGUGCUGAAGGCUUGCUGUAGGCUGUAUGCUG | 1 |
| 5F2 | GUGCUGGGCGGGGGCGGCGGGCCCUCCCGCAGAACACCAUGCGCUCUUCGGAA | 2 |
| 5F3 | GAAGCAAAGAAGGGGCAGAGGGAGCCCGUGAGCUGAGUGGGCCAGGGACUGGGAGAAGGAGUGAGGAGGCAGGGCCGGCAUGCCUCUGCUGCUGGCCAGA | 3 |
| 5F4 | GUGCUGGGCGGGGGCGGCGGGCCCUCCCGCAGAACACCAUGCGCUCUUCGGGA | 4 |

TABLE 1-continued

5' Flanking Regions for Molecular Scaffold

| 5' Flanking Region Name | 5' Flanking Region Sequence | 5' Flanking Region SEQ ID NO |
|---|---|---|
| 5F5 | GUGCUGGGCGGGGGCGGCGGGCCCUC CCGCAGAACACCAUGCGCUCCACGGAA | 5 |
| 5F6 | GGGCCCUCCCGCAGAACACCAUGCGCU CCACGGAA | 6 |
| 5F7 | CUCCCGCAGAACACCAUGCGCUCCACG GAA | 7 |
| 5F8 | GUGCUGGGCGGGGGCGGCGGGCCCUC CCGCAGAACACCAUGCGCUCCACGGAA G | 8 |
| 5F9 | GUGCUGGGCGGGGGCGGCGGGCCCUC CCGCAGAACACCAUGCGCUCCUCGGAA | 9 |

TABLE 2

Loop Motif Regions for Molecular Scaffold

| Loop Motif Region Name | Loop Motif Region Sequence | Loop Motif Region SEQ ID NO |
|---|---|---|
| L1 | UGUGACCUGG | 10 |
| L2 | UGUGAUUUGG | 11 |
| L3 | UAUAAUUUGG | 12 |
| L4 | CCUGACCCAGU | 13 |
| L5 | GUCUGCACCUGUCACUAG | 14 |
| L6 | GUGACCCAAG | 15 |
| L7 | GUGGCCACUGAGAAG | 16 |
| L8 | GUGACCCAAU | 17 |
| L9 | GUGACCCAAC | 18 |
| L10 | GUGGCCACUGAGAAA | 19 |

TABLE 3

3' Flanking Regions for Molecular Scaffold

| 3' Flanking Region Name | 3' Flanking Region Sequence | 3' Flanking Region SEQ ID NO |
|---|---|---|
| 3F1 | AGUGUAUGAUGCCUGUUACUAGCAUUC ACAUGGAACAAAUUGCUGCCGUG | 20 |
| 3F2 | CUGAGGAGCGCCUUGACAGCAGCCAUG GGAGGGCCGCCCCCUACCUCAGUGA | 21 |
| 3F3 | CUGUGGAGCGCCUUGACAGCAGCCAUG GGAGGGCCGCCCCCUACCUCAGUGA | 22 |
| 3F4 | UGGCCGUGUAGUGCUACCCAGCGCUGG CUGCCUCCUCAGCAUUGCAAUUCCUCU CCCAUCUGGGCACCAGUCAGCUACCCU GGUGGGAAUCUGGGUAGCC | 23 |
| 3F5 | GGCCGUGUAGUGCUACCCAGCGCUGGC UGCCUCCUCAGCAUUGCAAUUCCUCUC CCAUCUGGGCACCAGUCAGCUACCCUG GUGGGAAUCUGGGUAGCC | 24 |
| 3F6 | UCCUGAGGAGCGCCUUGACAGCAGCCA UGGGAGGGCCGCCCCCUACCUCAGUGA | 25 |
| 3F7 | CUGAGGAGCGCCUUGACAGCAGCCAUG GGAGGGCC | 26 |
| 3F8 | CUGCGGAGCGCCUUGACAGCAGCCAUG GGAGGGCCGCCCCCUACCUCAGUGA | 27 |

Any of the regions described in Tables 1-3, where U is T, may be used as modules in the molecular scaffolds described herein.

In one embodiment, the molecular scaffold may comprise at least one nucleic acid sequence encoding at least one 5' flanking region listed in Table 1. As a non-limiting example, the 5' flanking region may be 5F1, 5F2, 5F3, 5F4, 5F5, 5F6, 5F7, 5F8 or 5F9.

In one embodiment, the molecular scaffold may comprise at least one nucleic acid sequence encoding at least one 5F1 flanking region.

In one embodiment, the molecular scaffold may comprise at least one nucleic acid sequence encoding at least one 5F2 flanking region.

In one embodiment, the molecular scaffold may comprise at least one nucleic acid sequence encoding at least one 5F3 flanking region.

In one embodiment, the molecular scaffold may comprise at least one nucleic acid sequence encoding at least one 5F4 flanking region.

In one embodiment, the molecular scaffold may comprise at least one nucleic acid sequence encoding at least one 5F5 flanking region.

In one embodiment, the molecular scaffold may comprise at least one nucleic acid sequence encoding at least one 5F6 flanking region.

In one embodiment, the molecular scaffold may comprise at least one nucleic acid sequence encoding at least one 5F7 flanking region.

In one embodiment, the molecular scaffold may comprise at least one nucleic acid sequence encoding at least one 5F8 flanking region.

In one embodiment, the molecular scaffold may comprise at least one nucleic acid sequence encoding at least one 5F9 flanking region.

In one embodiment, the molecular scaffold may comprise at least one nucleic acid sequence encoding at least one one loop motif region listed in Table 2. As a non-limiting example, the loop motif region may be L1, L2, L3, L4, L5, L6, L7, L8, L9, or L10.

In one embodiment, the molecular scaffold may comprise at least one nucleic acid sequence encoding at least one L1 loop motif region.

In one embodiment, the molecular scaffold may comprise at least one nucleic acid sequence encoding at least one L2 loop motif region.

In one embodiment, the molecular scaffold may comprise at least one nucleic acid sequence encoding at least one L3 loop motif region.

In one embodiment, the molecular scaffold may comprise at least one nucleic acid sequence encoding at least one L4 loop motif region.

In one embodiment, the molecular scaffold may comprise at least one nucleic acid sequence encoding at least one L5 loop motif region.

In one embodiment, the molecular scaffold may comprise at least one nucleic acid sequence encoding at least one L6 loop motif region.

In one embodiment, the molecular scaffold may comprise at least one nucleic acid sequence encoding at least one L7 loop motif region.

In one embodiment, the molecular scaffold may comprise at least one nucleic acid sequence encoding at least one L8 loop motif region.

In one embodiment, the molecular scaffold may comprise at least one nucleic acid sequence encoding at least one L9 loop motif region.

In one embodiment, the molecular scaffold may comprise at least one nucleic acid sequence encoding at least one L10 loop motif region.

In one embodiment, the molecular scaffold may comprise at least one nucleic acid sequence encoding at least one 3' flanking region listed in Table 3. As a non-limiting example, the molecular scaffold may comprise the 3' flanking region 3F1, 3F2, 3F3, 3F4, 3F5, 3F6, 3F7 or 3F8.

In one embodiment, the molecular scaffold may comprise at least one nucleic acid sequence encoding at least one 3F1 flanking region.

In one embodiment, the molecular scaffold may comprise at least one nucleic acid sequence encoding at least one 3F2 flanking region.

In one embodiment, the molecular scaffold may comprise at least one nucleic acid sequence encoding at least one 3F3 flanking region.

In one embodiment, the molecular scaffold may comprise at least one nucleic acid sequence encoding at least one 3F4 flanking region.

In one embodiment, the molecular scaffold may comprise at least one nucleic acid sequence encoding at least one 3F5 flanking region.

In one embodiment, the molecular scaffold may comprise at least one nucleic acid sequence encoding at least one 3F6 flanking region.

In one embodiment, the molecular scaffold may comprise at least one nucleic acid sequence encoding at least one 3F7 flanking region.

In one embodiment, the molecular scaffold may comprise at least one nucleic acid sequence encoding at least one 3F8 flanking region.

In one embodiment, the molecular scaffold may comprise at least one nucleic acid sequence encoding at least one 5' flanking region and at least one loop motif region as described in Tables 1 and 2. As a non-limiting example, the 5' flanking region and the loop motif region may be 5F1 and L1, 5F1 and L2, 5F1 and L3, 5F1 and L4, 5F1 and L5, 5F1 and L6, 5F1 and L7, 5F1 and L8, 5F1 and L9, 5F1 and L10, 5F1 and L11, 5F2 and L1, 5F2 and L2, 5F2 and L3, 5F2 and L4, 5F2 and L5, 5F2 and L6, 5F2 and L7, 5F2 and L8, 5F2 and L9, 5F2 and L10, 5F2 and L11, 5F3 and L1, 5F3 and L2, 5F3 and L3, 5F3 and L4, 5F3 and L5, 5F3 and L6, 5F3 and L7, 5F3 and L8, 5F3 and L9, 5F3 and L10, 5F3 and L11, 5F4 and L1, 5F4 and L2, 5F4 and L3, 5F4 and L4, 5F4 and L5, 5F4 and L6, 5F4 and L7, 5F4 and L8, 5F4 and L9, 5F4 and L10, 5F4 and L11, 5F5 and L1, 5F5 and L2, 5F5 and L3, 5F5 and L4, 5F5 and L5, 5F5 and L6, 5F5 and L7, 5F5 and L8, 5F5 and L9, 5F5 and L10, 5F5 and L11, 5F6 and L1, 5F6 and L2, 5F6 and L3, 5F6 and L4, 5F6 and L5, 5F6 and L6, 5F6 and L7, 5F6 and L8, 5F6 and L9, 5F6 and L10, 5F6 and L11, 5F7 and L1, 5F7 and L2, 5F7 and L3, 5F7 and L4, 5F7 and L5, 5F7 and L6, 5F7 and L7, 5F7 and L8, 5F7 and L9, 5F7 and L10, 5F7 and L11, 5F8 and L1, 5F8 and L2, 5F8 and L3, 5F8 and L4, 5F8 and L5, 5F8 and L6, 5F8 and L7, 5F8 and L8, 5F8 and L9, 5F8 and L10, 5F8 and L11, 5F9 and L1, 5F9 and L2, 5F9 and L3, 5F9 and L4, 5F9 and L5, 5F9 and L6, 5F9 and L7, 5F9 and L8, 5F9 and L9, 5F9 and L10, or 5F9 and L11.

In one embodiment, the molecular scaffold may comprise at least one 3' flanking region and at least one loop motif region as described in Tables 2 and 3. As a non-limiting example, the molecular scaffold may comprise 3F1 and L1, 3F1 and L2, 3F1 and L3, 3F1 and L4, 3F1 and L5, 3F1 and L6, 3F1 and L7, 3F1 and L8, 3F1 and L9, 3F1 and L10, 3F1 and L11, 3F2 and L1, 3F2 and L2, 3F2 and L3, 3F2 and L4, 3F2 and L5, 3F2 and L6, 3F2 and L7, 3F2 and L8, 3F2 and L9, 3F2 and L10, 3F2 and L11, 3F3 and L1, 3F3 and L2, 3F3 and L3, 3F3 and L4, 3F3 and L5, 3F3 and L6, 3F3 and L7, 3F3 and L8, 3F3 and L9, 3F3 and L10, 3F3 and L11, 3F4 and L1, 3F4 and L2, 3F4 and L3, 3F4 and L4, 3F4 and L5, 3F4 and L6, 3F4 and L7, 3F4 and L8, 3F4 and L9, 3F4 and L10, 3F4 and L11, 3F5 and L1, 3F5 and L2, 3F5 and L3, 3F5 and L4, 3F5 and L5, 3F5 and L6, 3F5 and L7, 3F5 and L8, 3F5 and L9, 3F5 and L10, 3F5 and L11, 3F6 and L1, 3F6 and L2, 3F6 and L3, 3F6 and L4, 3F6 and L5, 3F6 and L6, 3F6 and L7, 3F6 and L8, 3F6 and L9, 3F6 and L10, 3F6 and L11, 3F7 and L1, 3F7 and L2, 3F7 and L3, 3F7 and L4, 3F7 and L5, 3F7 and L6, 3F7 and L7, 3F7 and L8, 3F7 and L9, 3F7 and L10, 3F7 and L11, 3F8 and L1, 3F8 and L2, 3F8 and L3, 3F8 and L4, 3F8 and L5, 3F8 and L6, 3F8 and L7, 3F8 and L8, 3F8 and L9, 3F8 and L10, or 3F8 and L11.

In one embodiment, the molecular scaffold may comprise at least one nucleic acid sequence encoding at least one 5F1 flanking region and at least one nucleic acid sequence encoding at least one L1 loop motif region.

In one embodiment, the molecular scaffold may comprise at least one nucleic acid sequence encoding at least one 5F1 flanking region and at least one nucleic acid sequence encoding at least one L2 loop motif region.

In one embodiment, the molecular scaffold may comprise at least one nucleic acid sequence encoding at least one 5F1 flanking region and at least one nucleic acid sequence encoding at least one L3 loop motif region.

In one embodiment, the molecular scaffold may comprise at least one nucleic acid sequence encoding at least one 5F1 flanking region and at least one nucleic acid sequence encoding at least one L4 loop motif region.

In one embodiment, the molecular scaffold may comprise at least one nucleic acid sequence encoding at least one 5F1 flanking region and at least one nucleic acid sequence encoding at least one L5 loop motif region.

In one embodiment, the molecular scaffold may comprise at least one nucleic acid sequence encoding at least one 5F1 flanking region and at least one nucleic acid sequence encoding at least one L6 loop motif region.

In one embodiment, the molecular scaffold may comprise at least one nucleic acid sequence encoding at least one 5F1 flanking region and at least one nucleic acid sequence encoding at least one L7 loop motif region.

In one embodiment, the molecular scaffold may comprise at least one nucleic acid sequence encoding at least one 5F1 flanking region and at least one nucleic acid sequence encoding at least one L8 loop motif region.

In one embodiment, the molecular scaffold may comprise at least one nucleic acid sequence encoding at least one 5F1 flanking region and at least one nucleic acid sequence encoding at least one L9 loop motif region.

In one embodiment, the molecular scaffold may comprise at least one nucleic acid sequence encoding at least one 5F1 flanking region and at least one nucleic acid sequence encoding at least one L10 loop motif region.

In one embodiment, the molecular scaffold may comprise at least one nucleic acid sequence encoding at least one 5F1 flanking region and at least one nucleic acid sequence encoding at least one L11 loop motif region.

In one embodiment, the molecular scaffold may comprise at least one nucleic acid sequence encoding at least one 5F2 flanking region and at least one nucleic acid sequence encoding at least one L1 loop motif region.

In one embodiment, the molecular scaffold may comprise at least one nucleic acid sequence encoding at least one 5F2 flanking region and at least one nucleic acid sequence encoding at least one L2 loop motif region.

In one embodiment, the molecular scaffold may comprise at least one nucleic acid sequence encoding at least one 5F2 flanking region and at least one nucleic acid sequence encoding at least one L3 loop motif region.

In one embodiment, the molecular scaffold may comprise at least one nucleic acid sequence encoding at least one 5F2 flanking region and at least one nucleic acid sequence encoding at least one L4 loop motif region.

In one embodiment, the molecular scaffold may comprise at least one nucleic acid sequence encoding at least one 5F2 flanking region and at least one nucleic acid sequence encoding at least one L5 loop motif region.

In one embodiment, the molecular scaffold may comprise at least one nucleic acid sequence encoding at least one 5F2 flanking region and at least one nucleic acid sequence encoding at least one L6 loop motif region.

In one embodiment, the molecular scaffold may comprise at least one nucleic acid sequence encoding at least one 5F2 flanking region and at least one nucleic acid sequence encoding at least one L7 loop motif region.

In one embodiment, the molecular scaffold may comprise at least one nucleic acid sequence encoding at least one 5F2 flanking region and at least one nucleic acid sequence encoding at least one L8 loop motif region.

In one embodiment, the molecular scaffold may comprise at least one nucleic acid sequence encoding at least one 5F2 flanking region and at least one nucleic acid sequence encoding at least one L9 loop motif region.

In one embodiment, the molecular scaffold may comprise at least one nucleic acid sequence encoding at least one 5F2 flanking region and at least one nucleic acid sequence encoding at least one L10 loop motif region.

In one embodiment, the molecular scaffold may comprise at least one nucleic acid sequence encoding at least one 5F2 flanking region and at least one nucleic acid sequence encoding at least one L11 loop motif region.

In one embodiment, the molecular scaffold may comprise at least one nucleic acid sequence encoding at least one 5F3 flanking region and at least one nucleic acid sequence encoding at least one L1 loop motif region.

In one embodiment, the molecular scaffold may comprise at least one nucleic acid sequence encoding at least one 5F3 flanking region and at least one nucleic acid sequence encoding at least one L2 loop motif region.

In one embodiment, the molecular scaffold may comprise at least one nucleic acid sequence encoding at least one 5F3 flanking region and at least one nucleic acid sequence encoding at least one L3 loop motif region.

In one embodiment, the molecular scaffold may comprise at least one nucleic acid sequence encoding at least one 5F3 flanking region and at least one nucleic acid sequence encoding at least one L4 loop motif region.

In one embodiment, the molecular scaffold may comprise at least one nucleic acid sequence encoding at least one 5F3 flanking region and at least one nucleic acid sequence encoding at least one L5 loop motif region.

In one embodiment, the molecular scaffold may comprise at least one nucleic acid sequence encoding at least one 5F3 flanking region and at least one nucleic acid sequence encoding at least one L6 loop motif region.

In one embodiment, the molecular scaffold may comprise at least one nucleic acid sequence encoding at least one 5F3 flanking region and at least one nucleic acid sequence encoding at least one L7 loop motif region.

In one embodiment, the molecular scaffold may comprise at least one nucleic acid sequence encoding at least one 5F3 flanking region and at least one nucleic acid sequence encoding at least one L8 loop motif region.

In one embodiment, the molecular scaffold may comprise at least one nucleic acid sequence encoding at least one 5F3 flanking region and at least one nucleic acid sequence encoding at least one L9 loop motif region.

In one embodiment, the molecular scaffold may comprise at least one nucleic acid sequence encoding at least one 5F3 flanking region and at least one nucleic acid sequence encoding at least one L10 loop motif region.

In one embodiment, the molecular scaffold may comprise at least one nucleic acid sequence encoding at least one 5F3 flanking region and at least one nucleic acid sequence encoding at least one L11 loop motif region.

In one embodiment, the molecular scaffold may comprise at least one nucleic acid sequence encoding at least one 5F4 flanking region and at least one nucleic acid sequence encoding at least one L1 loop motif region.

In one embodiment, the molecular scaffold may comprise at least one nucleic acid sequence encoding at least one 5F4 flanking region and at least one nucleic acid sequence encoding at least one L2 loop motif region.

In one embodiment, the molecular scaffold may comprise at least one nucleic acid sequence encoding at least one 5F4 flanking region and at least one nucleic acid sequence encoding at least one L3 loop motif region.

In one embodiment, the molecular scaffold may comprise at least one nucleic acid sequence encoding at least one 5F4 flanking region and at least one nucleic acid sequence encoding at least one L4 loop motif region.

In one embodiment, the molecular scaffold may comprise at least one nucleic acid sequence encoding at least one 5F4 flanking region and at least one nucleic acid sequence encoding at least one L5 loop motif region.

In one embodiment, the molecular scaffold may comprise at least one nucleic acid sequence encoding at least one 5F4 flanking region and at least one nucleic acid sequence encoding at least one L6 loop motif region.

In one embodiment, the molecular scaffold may comprise at least one nucleic acid sequence encoding at least one 5F4 flanking region and at least one nucleic acid sequence encoding at least one L7 loop motif region.

In one embodiment, the molecular scaffold may comprise at least one nucleic acid sequence encoding at least one 5F4 flanking region and at least one nucleic acid sequence encoding at least one L8 loop motif region.

In one embodiment, the molecular scaffold may comprise at least one nucleic acid sequence encoding at least one 5F4 flanking region and at least one nucleic acid sequence encoding at least one L9 loop motif region.

In one embodiment, the molecular scaffold may comprise at least one nucleic acid sequence encoding at least one 5F4 flanking region and at least one nucleic acid sequence encoding at least one L10 loop motif region.

In one embodiment, the molecular scaffold may comprise at least one nucleic acid sequence encoding at least one 5F4 flanking region and at least one nucleic acid sequence encoding at least one L11 loop motif region.

In one embodiment, the molecular scaffold may comprise at least one nucleic acid sequence encoding at least one 5F5 flanking region and at least one nucleic acid sequence encoding at least one L1 loop motif region.

In one embodiment, the molecular scaffold may comprise at least one nucleic acid sequence encoding at least one 5F5 flanking region and at least one nucleic acid sequence encoding at least one L2 loop motif region.

In one embodiment, the molecular scaffold may comprise at least one nucleic acid sequence encoding at least one 5F5 flanking region and at least one nucleic acid sequence encoding at least one L3 loop motif region.

In one embodiment, the molecular scaffold may comprise at least one nucleic acid sequence encoding at least one 5F5 flanking region and at least one nucleic acid sequence encoding at least one L4 loop motif region.

In one embodiment, the molecular scaffold may comprise at least one nucleic acid sequence encoding at least one 5F5 flanking region and at least one nucleic acid sequence encoding at least one L5 loop motif region.

In one embodiment, the molecular scaffold may comprise at least one nucleic acid sequence encoding at least one 5F5 flanking region and at least one nucleic acid sequence encoding at least one L6 loop motif region.

In one embodiment, the molecular scaffold may comprise at least one nucleic acid sequence encoding at least one 5F5 flanking region and at least one nucleic acid sequence encoding at least one L7 loop motif region.

In one embodiment, the molecular scaffold may comprise at least one nucleic acid sequence encoding at least one 5F5 flanking region and at least one nucleic acid sequence encoding at least one L8 loop motif region.

In one embodiment, the molecular scaffold may comprise at least one nucleic acid sequence encoding at least one 5F5 flanking region and at least one nucleic acid sequence encoding at least one L9 loop motif region.

In one embodiment, the molecular scaffold may comprise at least one nucleic acid sequence encoding at least one 5F5 flanking region and at least one nucleic acid sequence encoding at least one L10 loop motif region.

In one embodiment, the molecular scaffold may comprise at least one nucleic acid sequence encoding at least one 5F5 flanking region and at least one nucleic acid sequence encoding at least one L11 loop motif region.

In one embodiment, the molecular scaffold may comprise at least one nucleic acid sequence encoding at least one 5F6 flanking region and at least one nucleic acid sequence encoding at least one L1 loop motif region.

In one embodiment, the molecular scaffold may comprise at least one nucleic acid sequence encoding at least one 5F6 flanking region and at least one nucleic acid sequence encoding at least one L2 loop motif region.

In one embodiment, the molecular scaffold may comprise at least one nucleic acid sequence encoding at least one 5F6 flanking region and at least one nucleic acid sequence encoding at least one L3 loop motif region.

In one embodiment, the molecular scaffold may comprise at least one nucleic acid sequence encoding at least one 5F6 flanking region and at least one nucleic acid sequence encoding at least one L4 loop motif region.

In one embodiment, the molecular scaffold may comprise at least one nucleic acid sequence encoding at least one 5F6 flanking region and at least one nucleic acid sequence encoding at least one L5 loop motif region.

In one embodiment, the molecular scaffold may comprise at least one nucleic acid sequence encoding at least one 5F6 flanking region and at least one nucleic acid sequence encoding at least one L6 loop motif region.

In one embodiment, the molecular scaffold may comprise at least one nucleic acid sequence encoding at least one 5F6 flanking region and at least one nucleic acid sequence encoding at least one L7 loop motif region.

In one embodiment, the molecular scaffold may comprise at least one nucleic acid sequence encoding at least one 5F6 flanking region and at least one nucleic acid sequence encoding at least one L8 loop motif region.

In one embodiment, the molecular scaffold may comprise at least one nucleic acid sequence encoding at least one 5F6 flanking region and at least one nucleic acid sequence encoding at least one L9 loop motif region.

In one embodiment, the molecular scaffold may comprise at least one nucleic acid sequence encoding at least one 5F6 flanking region and at least one nucleic acid sequence encoding at least one L10 loop motif region.

In one embodiment, the molecular scaffold may comprise at least one nucleic acid sequence encoding at least one 5F6 flanking region and at least one nucleic acid sequence encoding at least one L11 loop motif region.

In one embodiment, the molecular scaffold may comprise at least one nucleic acid sequence encoding at least one 5F7 flanking region and at least one nucleic acid sequence encoding at least one L1 loop motif region.

In one embodiment, the molecular scaffold may comprise at least one nucleic acid sequence encoding at least one 5F7 flanking region and at least one nucleic acid sequence encoding at least one L2 loop motif region.

In one embodiment, the molecular scaffold may comprise at least one nucleic acid sequence encoding at least one 5F7 flanking region and at least one nucleic acid sequence encoding at least one L3 loop motif region.

In one embodiment, the molecular scaffold may comprise at least one nucleic acid sequence encoding at least one 5F7 flanking region and at least one nucleic acid sequence encoding at least one L4 loop motif region.

In one embodiment, the molecular scaffold may comprise at least one nucleic acid sequence encoding at least one 5F7 flanking region and at least one nucleic acid sequence encoding at least one L5 loop motif region.

In one embodiment, the molecular scaffold may comprise at least one nucleic acid sequence encoding at least one 5F7 flanking region and at least one nucleic acid sequence encoding at least one L6 loop motif region.

In one embodiment, the molecular scaffold may comprise at least one nucleic acid sequence encoding at least one 5F7 flanking region and at least one nucleic acid sequence encoding at least one L7 loop motif region.

In one embodiment, the molecular scaffold may comprise at least one nucleic acid sequence encoding at least one 5F7 flanking region and at least one nucleic acid sequence encoding at least one L8 loop motif region.

In one embodiment, the molecular scaffold may comprise at least one nucleic acid sequence encoding at least one 5F7 flanking region and at least one nucleic acid sequence encoding at least one L9 loop motif region.

In one embodiment, the molecular scaffold may comprise at least one nucleic acid sequence encoding at least one 5F7 flanking region and at least one nucleic acid sequence encoding at least one L10 loop motif region.

In one embodiment, the molecular scaffold may comprise at least one nucleic acid sequence encoding at least one 5F7 flanking region and at least one nucleic acid sequence encoding at least one L11 loop motif region.

In one embodiment, the molecular scaffold may comprise at least one nucleic acid sequence encoding at least one 5F8 flanking region and at least one nucleic acid sequence encoding at least one L1 loop motif region.

In one embodiment, the molecular scaffold may comprise at least one nucleic acid sequence encoding at least one 5F8 flanking region and at least one nucleic acid sequence encoding at least one L2 loop motif region.

In one embodiment, the molecular scaffold may comprise at least one nucleic acid sequence encoding at least one 5F8 flanking region and at least one nucleic acid sequence encoding at least one L3 loop motif region.

In one embodiment, the molecular scaffold may comprise at least one nucleic acid sequence encoding at least one 5F8 flanking region and at least one nucleic acid sequence encoding at least one L4 loop motif region.

In one embodiment, the molecular scaffold may comprise at least one nucleic acid sequence encoding at least one 5F8 flanking region and at least one nucleic acid sequence encoding at least one L5 loop motif region.

In one embodiment, the molecular scaffold may comprise at least one nucleic acid sequence encoding at least one 5F8 flanking region and at least one nucleic acid sequence encoding at least one L6 loop motif region.

In one embodiment, the molecular scaffold may comprise at least one nucleic acid sequence encoding at least one 5F8 flanking region and at least one nucleic acid sequence encoding at least one L7 loop motif region.

In one embodiment, the molecular scaffold may comprise at least one nucleic acid sequence encoding at least one 5F8 flanking region and at least one nucleic acid sequence encoding at least one L8 loop motif region.

In one embodiment, the molecular scaffold may comprise at least one nucleic acid sequence encoding at least one 5F8 flanking region and at least one nucleic acid sequence encoding at least one L9 loop motif region.

In one embodiment, the molecular scaffold may comprise at least one nucleic acid sequence encoding at least one 5F8 flanking region and at least one nucleic acid sequence encoding at least one L10 loop motif region.

In one embodiment, the molecular scaffold may comprise at least one nucleic acid sequence encoding at least one 5F8 flanking region and at least one nucleic acid sequence encoding at least one L11 loop motif region.

In one embodiment, the molecular scaffold may comprise at least one nucleic acid sequence encoding at least one 5F9 flanking region and at least one nucleic acid sequence encoding at least one L1 loop motif region.

In one embodiment, the molecular scaffold may comprise at least one nucleic acid sequence encoding at least one 5F9 flanking region and at least one nucleic acid sequence encoding at least one L2 loop motif region.

In one embodiment, the molecular scaffold may comprise at least one nucleic acid sequence encoding at least one 5F9 flanking region and at least one nucleic acid sequence encoding at least one L3 loop motif region.

In one embodiment, the molecular scaffold may comprise at least one nucleic acid sequence encoding at least one 5F9 flanking region and at least one nucleic acid sequence encoding at least one L4 loop motif region.

In one embodiment, the molecular scaffold may comprise at least one nucleic acid sequence encoding at least one 5F9 flanking region and at least one nucleic acid sequence encoding at least one L5 loop motif region.

In one embodiment, the molecular scaffold may comprise at least one nucleic acid sequence encoding at least one 5F9 flanking region and at least one nucleic acid sequence encoding at least one L6 loop motif region.

In one embodiment, the molecular scaffold may comprise at least one nucleic acid sequence encoding at least one 5F9 flanking region and at least one nucleic acid sequence encoding at least one L7 loop motif region.

In one embodiment, the molecular scaffold may comprise at least one nucleic acid sequence encoding at least one 5F9 flanking region and at least one nucleic acid sequence encoding at least one L8 loop motif region.

In one embodiment, the molecular scaffold may comprise at least one nucleic acid sequence encoding at least one 5F9 flanking region and at least one nucleic acid sequence encoding at least one L9 loop motif region.

In one embodiment, the molecular scaffold may comprise at least one nucleic acid sequence encoding at least one 5F9 flanking region and at least one nucleic acid sequence encoding at least one L10 loop motif region.

In one embodiment, the molecular scaffold may comprise at least one nucleic acid sequence encoding at least one 5F9 flanking region and at least one nucleic acid sequence encoding at least one L11 loop motif region.

In one embodiment, the molecular scaffold may comprise at least one nucleic acid sequence encoding at least one 5' flanking region and at least one nucleic acid sequence encoding at least 3' flanking region as described in Tables 1 and 3. As a non-limiting example, the molecular scaffold may comprise 5F1 and 3F1, 5F1 and 3F2, 5F1 and 3F3, 5F1 and 3F4, 5F1 and 3F5, 5F1 and 3F6, 5F1 and 3F7, 5F1 and 3F8, 5F2 and 3F1, 5F2 and 3F2, 5F2 and 3F3, 5F2 and 3F4, 5F2 and 3F5, 5F2 and 3F6, 5F2 and 3F7, 5F2 and 3F8, 5F3 and 3F1, 5F3 and 3F2, 5F3 and 3F3, 5F3 and 3F4, 5F3 and 3F5, 5F3 and 3F6, 5F3 and 3F7, 5F3 and 3F8, 5F4 and 3F1, 5F4 and 3F2, 5F4 and 3F3, 5F4 and 3F4, 5F4 and 3F5, 5F4 and 3F6, 5F4 and 3F7, 5F4 and 3F8, 5F5 and 3F1, 5F5 and 3F2, 5F5 and 3F3, 5F5 and 3F4, 5F5 and 3F5, 5F5 and 3F6, 5F5 and 3F7, 5F5 and 3F8, 5F6 and 3F1, 5F6 and 3F2, 5F6 and 3F3, 5F6 and 3F4, 5F6 and 3F5, 5F6 and 3F6, 5F6 and 3F7, 5F6 and 3F8, 5F7 and 3F1, 5F7 and 3F2, 5F7 and 3F3, 5F7 and 3F4, 5F7 and 3F5, 5F7 and 3F6, 5F7 and 3F7, 5F7 and 3F8, 5F8 and 3F1, 5F8 and 3F2, 5F8 and 3F3, 5F8 and 3F4, 5F8 and 3F5, 5F8 and 3F6, 5F8 and 3F7, 5F8 and 3F8, 5F9 and 3F1, 5F9 and 3F2, 5F9 and 3F3, 5F9 and 3F4, 5F9 and 3F5, 5F9 and 3F6, 5F9 and 3F7, or 5F9 and 3F8.

In one embodiment, the molecular scaffold may comprise at least one nucleic acid sequence encoding at least one 5F1 5' flanking region and at least one nucleic acid sequence encoding at least one 3F1 3' flanking region.

In one embodiment, the molecular scaffold may comprise at least one nucleic acid sequence encoding at least one 5F1

5' flanking region and at least one nucleic acid sequence encoding at least one 3F2 3' flanking region.

In one embodiment, the molecular scaffold may comprise at least one nucleic acid sequence encoding at least one 5F1 5' flanking region and at least one nucleic acid sequence encoding at least one 3F3 3' flanking region.

In one embodiment, the molecular scaffold may comprise at least one nucleic acid sequence encoding at least one 5F1 5' flanking region and at least one nucleic acid sequence encoding at least one 3F4 3' flanking region.

In one embodiment, the molecular scaffold may comprise at least one nucleic acid sequence encoding at least one 5F1 5' flanking region and at least one nucleic acid sequence encoding at least one 3F5 3' flanking region.

In one embodiment, the molecular scaffold may comprise at least one nucleic acid sequence encoding at least one 5F1 5' flanking region and at least one nucleic acid sequence encoding at least one 3F6 3' flanking region.

In one embodiment, the molecular scaffold may comprise at least one nucleic acid sequence encoding at least one 5F1 5' flanking region and at least one nucleic acid sequence encoding at least one 3F7 3' flanking region.

In one embodiment, the molecular scaffold may comprise at least one nucleic acid sequence encoding at least one 5F1 5' flanking region and at least one nucleic acid sequence encoding at least one 3F8 3' flanking region.

In one embodiment, the molecular scaffold may comprise at least one nucleic acid sequence encoding at least one 5F2 5' flanking region and at least one nucleic acid sequence encoding at least one 3F1 3' flanking region.

In one embodiment, the molecular scaffold may comprise at least one nucleic acid sequence encoding at least one 5F2 5' flanking region and at least one nucleic acid sequence encoding at least one 3F2 3' flanking region.

In one embodiment, the molecular scaffold may comprise at least one nucleic acid sequence encoding at least one 5F2 5' flanking region and at least one nucleic acid sequence encoding at least one 3F3 3' flanking region.

In one embodiment, the molecular scaffold may comprise at least one nucleic acid sequence encoding at least one 5F2 5' flanking region and at least one nucleic acid sequence encoding at least one 3F4 3' flanking region.

In one embodiment, the molecular scaffold may comprise at least one nucleic acid sequence encoding at least one 5F2 5' flanking region and at least one nucleic acid sequence encoding at least one 3F5 3' flanking region.

In one embodiment, the molecular scaffold may comprise at least one nucleic acid sequence encoding at least one 5F2 5' flanking region and at least one nucleic acid sequence encoding at least one 3F6 3' flanking region.

In one embodiment, the molecular scaffold may comprise at least one nucleic acid sequence encoding at least one 5F2 5' flanking region and at least one nucleic acid sequence encoding at least one 3F7 3' flanking region.

In one embodiment, the molecular scaffold may comprise at least one nucleic acid sequence encoding at least one 5F2 5' flanking region and at least one nucleic acid sequence encoding at least one 3F8 3' flanking region.

In one embodiment, the molecular scaffold may comprise at least one nucleic acid sequence encoding at least one 5F3 5' flanking region and at least one nucleic acid sequence encoding at least one 3F1 3' flanking region.

In one embodiment, the molecular scaffold may comprise at least one nucleic acid sequence encoding at least one 5F3 5' flanking region and at least one nucleic acid sequence encoding at least one 3F2 3' flanking region.

In one embodiment, the molecular scaffold may comprise at least one nucleic acid sequence encoding at least one 5F3 5' flanking region and at least one nucleic acid sequence encoding at least one 3F3 3' flanking region.

In one embodiment, the molecular scaffold may comprise at least one nucleic acid sequence encoding at least one 5F3 5' flanking region and at least one nucleic acid sequence encoding at least one 3F4 3' flanking region.

In one embodiment, the molecular scaffold may comprise at least one nucleic acid sequence encoding at least one 5F3 5' flanking region and at least one nucleic acid sequence encoding at least one 3F5 3' flanking region.

In one embodiment, the molecular scaffold may comprise at least one nucleic acid sequence encoding at least one 5F3 5' flanking region and at least one nucleic acid sequence encoding at least one 3F6 3' flanking region.

In one embodiment, the molecular scaffold may comprise at least one nucleic acid sequence encoding at least one 5F3 5' flanking region and at least one nucleic acid sequence encoding at least one 3F7 3' flanking region.

In one embodiment, the molecular scaffold may comprise at least one nucleic acid sequence encoding at least one 5F3 5' flanking region and at least one nucleic acid sequence encoding at least one 3F8 3' flanking region.

In one embodiment, the molecular scaffold may comprise at least one nucleic acid sequence encoding at least one 5F4 5' flanking region and at least one nucleic acid sequence encoding at least one 3F1 3' flanking region.

In one embodiment, the molecular scaffold may comprise at least one nucleic acid sequence encoding at least one 5F4 5' flanking region and at least one nucleic acid sequence encoding at least one 3F2 3' flanking region.

In one embodiment, the molecular scaffold may comprise at least one nucleic acid sequence encoding at least one 5F4 5' flanking region and at least one nucleic acid sequence encoding at least one 3F3 3' flanking region.

In one embodiment, the molecular scaffold may comprise at least one nucleic acid sequence encoding at least one 5F4 5' flanking region and at least one nucleic acid sequence encoding at least one 3F4 3' flanking region.

In one embodiment, the molecular scaffold may comprise at least one nucleic acid sequence encoding at least one 5F4 5' flanking region and at least one nucleic acid sequence encoding at least one 3F5 3' flanking region.

In one embodiment, the molecular scaffold may comprise at least one nucleic acid sequence encoding at least one 5F4 5' flanking region and at least one nucleic acid sequence encoding at least one 3F6 3' flanking region.

In one embodiment, the molecular scaffold may comprise at least one nucleic acid sequence encoding at least one 5F4 5' flanking region and at least one nucleic acid sequence encoding at least one 3F7 3' flanking region.

In one embodiment, the molecular scaffold may comprise at least one nucleic acid sequence encoding at least one 5F4 5' flanking region and at least one nucleic acid sequence encoding at least one 3F8 3' flanking region.

In one embodiment, the molecular scaffold may comprise at least one nucleic acid sequence encoding at least one 5F5 5' flanking region and at least one nucleic acid sequence encoding at least one 3F1 3' flanking region.

In one embodiment, the molecular scaffold may comprise at least one nucleic acid sequence encoding at least one 5F5 5' flanking region and at least one nucleic acid sequence encoding at least one 3F2 3' flanking region.

In one embodiment, the molecular scaffold may comprise at least one nucleic acid sequence encoding at least one 5F5

5' flanking region and at least one nucleic acid sequence encoding at least one 3F3 3' flanking region.

In one embodiment, the molecular scaffold may comprise at least one nucleic acid sequence encoding at least one 5F5 5' flanking region and at least one nucleic acid sequence encoding at least one 3F4 3' flanking region.

In one embodiment, the molecular scaffold may comprise at least one nucleic acid sequence encoding at least one 5F5 5' flanking region and at least one nucleic acid sequence encoding at least one 3F5 3' flanking region.

In one embodiment, the molecular scaffold may comprise at least one nucleic acid sequence encoding at least one 5F5 5' flanking region and at least one nucleic acid sequence encoding at least one 3F6 3' flanking region.

In one embodiment, the molecular scaffold may comprise at least one nucleic acid sequence encoding at least one 5FS 5' flanking region and at least one nucleic acid sequence encoding at least one 3F7 3' flanking region.

In one embodiment, the molecular scaffold may comprise at least one nucleic acid sequence encoding at least one 5FS 5' flanking region and at least one nucleic acid sequence encoding at least one 3F8 3' flanking region.

In one embodiment, the molecular scaffold may comprise at least one nucleic acid sequence encoding at least one 5F6 5' flanking region and at least one nucleic acid sequence encoding at least one 3F1 3' flanking region.

In one embodiment, the molecular scaffold may comprise at least one nucleic acid sequence encoding at least one 5F6 5' flanking region and at least one nucleic acid sequence encoding at least one 3F2 3' flanking region.

In one embodiment, the molecular scaffold may comprise at least one nucleic acid sequence encoding at least one 5F6 5' flanking region and at least one nucleic acid sequence encoding at least one 3F3 3' flanking region.

In one embodiment, the molecular scaffold may comprise at least one nucleic acid sequence encoding at least one 5F6 5' flanking region and at least one nucleic acid sequence encoding at least one 3F4 3' flanking region.

In one embodiment, the molecular scaffold may comprise at least one nucleic acid sequence encoding at least one 5F6 5' flanking region and at least one nucleic acid sequence encoding at least one 3F5 3' flanking region.

In one embodiment, the molecular scaffold may comprise at least one nucleic acid sequence encoding at least one 5F6 5' flanking region and at least one nucleic acid sequence encoding at least one 3F6 3' flanking region.

In one embodiment, the molecular scaffold may comprise at least one nucleic acid sequence encoding at least one 5F6 5' flanking region and at least one nucleic acid sequence encoding at least one 3F7 3' flanking region.

In one embodiment, the molecular scaffold may comprise at least one nucleic acid sequence encoding at least one 5F6 5' flanking region and at least one nucleic acid sequence encoding at least one 3F8 3' flanking region.

In one embodiment, the molecular scaffold may comprise at least one nucleic acid sequence encoding at least one 5F7 5' flanking region and at least one nucleic acid sequence encoding at least one 3F1 3' flanking region.

In one embodiment, the molecular scaffold may comprise at least one nucleic acid sequence encoding at least one 5F7 5' flanking region and at least one nucleic acid sequence encoding at least one 3F2 3' flanking region.

In one embodiment, the molecular scaffold may comprise at least one nucleic acid sequence encoding at least one 5F7 5' flanking region and at least one nucleic acid sequence encoding at least one 3F3 3' flanking region.

In one embodiment, the molecular scaffold may comprise at least one nucleic acid sequence encoding at least one 5F7 5' flanking region and at least one nucleic acid sequence encoding at least one 3F4 3' flanking region.

In one embodiment, the molecular scaffold may comprise at least one nucleic acid sequence encoding at least one 5F7 5' flanking region and at least one nucleic acid sequence encoding at least one 3F5 3' flanking region.

In one embodiment, the molecular scaffold may comprise at least one nucleic acid sequence encoding at least one 5F7 5' flanking region and at least one nucleic acid sequence encoding at least one 3F6 3' flanking region.

In one embodiment, the molecular scaffold may comprise at least one nucleic acid sequence encoding at least one 5F7 5' flanking region and at least one nucleic acid sequence encoding at least one 3F7 3' flanking region.

In one embodiment, the molecular scaffold may comprise at least one nucleic acid sequence encoding at least one 5F7 5' flanking region and at least one nucleic acid sequence encoding at least one 3F8 3' flanking region.

In one embodiment, the molecular scaffold may comprise at least one nucleic acid sequence encoding at least one 5F8 5' flanking region and at least one nucleic acid sequence encoding at least one 3F1 3' flanking region.

In one embodiment, the molecular scaffold may comprise at least one nucleic acid sequence encoding at least one 5F8 5' flanking region and at least one nucleic acid sequence encoding at least one 3F2 3' flanking region.

In one embodiment, the molecular scaffold may comprise at least one nucleic acid sequence encoding at least one 5F8 5' flanking region and at least one nucleic acid sequence encoding at least one 3F3 3' flanking region.

In one embodiment, the molecular scaffold may comprise at least one nucleic acid sequence encoding at least one 5F8 5' flanking region and at least one nucleic acid sequence encoding at least one 3F4 3' flanking region.

In one embodiment, the molecular scaffold may comprise at least one nucleic acid sequence encoding at least one 5F8 5' flanking region and at least one nucleic acid sequence encoding at least one 3F5 3' flanking region.

In one embodiment, the molecular scaffold may comprise at least one nucleic acid sequence encoding at least one 5F8 5' flanking region and at least one nucleic acid sequence encoding at least one 3F6 3' flanking region.

In one embodiment, the molecular scaffold may comprise at least one nucleic acid sequence encoding at least one 5F8 5' flanking region and at least one nucleic acid sequence encoding at least one 3F7 3' flanking region.

In one embodiment, the molecular scaffold may comprise at least one nucleic acid sequence encoding at least one 5F8 5' flanking region and at least one nucleic acid sequence encoding at least one 3F8 3' flanking region.

In one embodiment, the molecular scaffold may comprise at least one nucleic acid sequence encoding at least one 5F9 5' flanking region and at least one nucleic acid sequence encoding at least one 3F1 3' flanking region.

In one embodiment, the molecular scaffold may comprise at least one nucleic acid sequence encoding at least one 5F9 5' flanking region and at least one nucleic acid sequence encoding at least one 3F2 3' flanking region.

In one embodiment, the molecular scaffold may comprise at least one nucleic acid sequence encoding at least one 5F9 5' flanking region and at least one nucleic acid sequence encoding at least one 3F3 3' flanking region.

In one embodiment, the molecular scaffold may comprise at least one nucleic acid sequence encoding at least one 5F9

5' flanking region and at least one nucleic acid sequence encoding at least one 3F4 3' flanking region.

In one embodiment, the molecular scaffold may comprise at least one nucleic acid sequence encoding at least one 5F9 5' flanking region and at least one nucleic acid sequence encoding at least one 3F5 3' flanking region.

In one embodiment, the molecular scaffold may comprise at least one nucleic acid sequence encoding at least one 5F9 5' flanking region and at least one nucleic acid sequence encoding at least one 3F6 3' flanking region.

In one embodiment, the molecular scaffold may comprise at least one nucleic acid sequence encoding at least one 5F9 5' flanking region and at least one nucleic acid sequence encoding at least one 3F7 3' flanking region.

In one embodiment, the molecular scaffold may comprise at least one nucleic acid sequence encoding at least one 5F9 5' flanking region and at least one nucleic acid sequence encoding at least one 3F8 3' flanking region.

In one embodiment, the molecular scaffold may comprise at least one 5' flanking region, at least one loop motif region and at least one 3' flanking region. As a non-limiting example, the molecular scaffold may comprise 5F1, L1 and 3F1; 5F1, L1 and 3F2; 5F1, L1 and 3F3; 5F1, L1 and 3F4; 5F1, L1 and 3F5; 5F1, L1 and 3F6; 5F1, L1 and 3F7; 5F1, L1 and 3F8; 5F2, L1 and 3F1; 5F2, L1 and 3F2; 5F2, L1 and 3F3; 5F2, L1 and 3F4; 5F2, L1 and 3F5; 5F2, L1 and 3F6; 5F2, L1 and 3F7; 5F2, L1 and 3F8; 5F3, L1 and 3F1; 5F3, L1 and 3F2; 5F3, L1 and 3F3; 5F3, L1 and 3F4; 5F3, L1 and 3F5; 5F3, L1 and 3F6; 5F3, L1 and 3F7; 5F3, L1 and 3F8; 5F4, L1 and 3F1; 5F4, L1 and 3F2; 5F4, L1 and 3F3; 5F4, L1 and 3F4; 5F4, L1 and 3F5; 5F4, L1 and 3F6; 5F4, L1 and 3F7; 5F4, L1 and 3F8; 5F5, L1 and 3F1; 5F5, L1 and 3F2; 5F5, L1 and 3F3; 5F5, L1 and 3F4; 5F5, L1 and 3F5; 5F5, L1 and 3F6; 5F5, L1 and 3F7; 5F5, L1 and 3F8; 5F6, L1 and 3F1; 5F6, L1 and 3F2; 5F6, L1 and 3F3; 5F6, L1 and 3F4; 5F6, L1 and 3F5; 5F6, L1 and 3F6; 5F6, L1 and 3F7; 5F6, L1 and 3F8; 5F7, L1 and 3F1; 5F7, L1 and 3F2; 5F7, L1 and 3F3; 5F7, L1 and 3F4; 5F7, L1 and 3F5; 5F7, L1 and 3F6; 5F7, L1 and 3F7; 5F7, L1 and 3F8; 5F8, L1 and 3F1; 5F8, L1 and 3F2; 5F8, L1 and 3F3; 5F8, L1 and 3F4; 5F8, L1 and 3F5; 5F8, L1 and 3F6; 5F8, L1 and 3F7; 5F8, L1 and 3F8; 5F9, L1 and 3F1; 5F9, L1 and 3F2; 5F9, L1 and 3F3; 5F9, L1 and 3F4; 5F9, L1 and 3F5; 5F9, L1 and 3F6; 5F9, L1 and 3F7; 5F9, L1 and 3F8; 5F1, L2 and 3F1; 5F1, L2 and 3F2; 5F1, L2 and 3F3; 5F1, L2 and 3F4; 5F1, L2 and 3F5; 5F1, L2 and 3F6; 5F1, L2 and 3F7; 5F1, L2 and 3F8; 5F2, L2 and 3F1; 5F2, L2 and 3F2; 5F2, L2 and 3F3; 5F2, L2 and 3F4; 5F2, L2 and 3F5; 5F2, L2 and 3F6; 5F2, L2 and 3F7; 5F2, L2 and 3F8; 5F3, L2 and 3F1; 5F3, L2 and 3F2; 5F3, L2 and 3F3; 5F3, L2 and 3F4; 5F3, L2 and 3F5; 5F3, L2 and 3F6; 5F3, L2 and 3F7; 5F3, L2 and 3F8; 5F4, L2 and 3F1; 5F4, L2 and 3F2; 5F4, L2 and 3F3; 5F4, L2 and 3F4; 5F4, L2 and 3F5; 5F4, L2 and 3F6; 5F4, L2 and 3F7; 5F4, L2 and 3F8; 5F5, L2 and 3F1; 5F5, L2 and 3F2; 5F5, L2 and 3F3; 5F5, L2 and 3F4; 5F5, L2 and 3F5; 5F5, L2 and 3F6; 5F5, L2 and 3F7; 5F5, L2 and 3F8; 5F6, L2 and 3F1; 5F6, L2 and 3F2; 5F6, L2 and 3F3; 5F6, L2 and 3F4; 5F6, L2 and 3F5; 5F6, L2 and 3F6; 5F6, L2 and 3F7; 5F6, L2 and 3F8; 5F7, L2 and 3F1; 5F7, L2 and 3F2; 5F7, L2 and 3F3; 5F7, L2 and 3F4; 5F7, L2 and 3F5; 5F7, L2 and 3F6; 5F7, L2 and 3F7; 5F7, L2 and 3F8; 5F8, L2 and 3F1; 5F8, L2 and 3F2; 5F8, L2 and 3F3; 5F8, L2 and 3F4; 5F8, L2 and 3F5; 5F8, L2 and 3F6; 5F8, L2 and 3F7; 5F8, L2 and 3F8; 5F9, L2 and 3F1; 5F9, L2 and 3F2; 5F9, L2 and 3F3; 5F9, L2 and 3F4; 5F9, L2 and 3F5; 5F9, L2 and 3F6; 5F9, L2 and 3F7; 5F9, L2 and 3F8; 5F1, L3 and 3F1; 5F1, L3 and 3F2; 5F1, L3 and 3F3; 5F1, L3 and 3F4; 5F1, L3 and 3F5; 5F1, L3 and 3F6; 5F1, L3 and 3F7; 5F1, L3 and 3F8; 5F2, L3 and 3F1; 5F2, L3 and 3F2; 5F2, L3 and 3F3; 5F2, L3 and 3F4; 5F2, L3 and 3F5; 5F2, L3 and 3F6; 5F2, L3 and 3F7; 5F2, L3 and 3F8; 5F3, L3 and 3F1; 5F3, L3 and 3F2; 5F3, L3 and 3F3; 5F3, L3 and 3F4; 5F3, L3 and 3F5; 5F3, L3 and 3F6; 5F3, L3 and 3F7; 5F3, L3 and 3F8; 5F4, L3 and 3F1; 5F4, L3 and 3F2; 5F4, L3 and 3F3; 5F4, L3 and 3F4; 5F4, L3 and 3F5; 5F4, L3 and 3F6; 5F4, L3 and 3F7; 5F4, L3 and 3F8; 5F5, L3 and 3F1; 5F5, L3 and 3F2; 5F5, L3 and 3F3; 5F5, L3 and 3F4; 5F5, L3 and 3F5; 5F5, L3 and 3F6; 5F5, L3 and 3F7; 5F5, L3 and 3F8; 5F6, L3 and 3F1; 5F6, L3 and 3F2; 5F6, L3 and 3F3; 5F6, L3 and 3F4; 5F6, L3 and 3F5; 5F6, L3 and 3F6; 5F6, L3 and 3F7; 5F6, L3 and 3F8; 5F7, L3 and 3F1; 5F7, L3 and 3F2; 5F7, L3 and 3F3; 5F7, L3 and 3F4; 5F7, L3 and 3F5; 5F7, L3 and 3F6; 5F7, L3 and 3F7; 5F7, L3 and 3F8; 5F8, L3 and 3F1; 5F8, L3 and 3F2; 5F8, L3 and 3F3; 5F8, L3 and 3F4; 5F8, L3 and 3F5; 5F8, L3 and 3F6; 5F8, L3 and 3F7; 5F8, L3 and 3F8; 5F9, L3 and 3F1; 5F9, L3 and 3F2; 5F9, L3 and 3F3; 5F9, L3 and 3F4; 5F9, L3 and 3F5; 5F9, L3 and 3F6; 5F9, L3 and 3F7; 5F9, L3 and 3F8; 5F1, L4 and 3F1; 5F1, L4 and 3F2; 5F1, L4 and 3F3; 5F1, L4 and 3F4; 5F1, L4 and 3F5; 5F1, L4 and 3F6; 5F1, L4 and 3F7; 5F1, L4 and 3F8; 5F2, L4 and 3F1; 5F2, L4 and 3F2; 5F2, L4 and 3F3; 5F2, L4 and 3F4; 5F2, L4 and 3F5; 5F2, L4 and 3F6; 5F2, L4 and 3F7; 5F2, L4 and 3F8; 5F3, L4 and 3F1; 5F3, L4 and 3F2; 5F3, L4 and 3F3; 5F3, L4 and 3F4; 5F3, L4 and 3F5; 5F3, L4 and 3F6; 5F3, L4 and 3F7; 5F3, L4 and 3F8; 5F4, L4 and 3F1; 5F4, L4 and 3F2; 5F4, L4 and 3F3; 5F4, L4 and 3F4; 5F4, L4 and 3F5; 5F4, L4 and 3F6; 5F4, L4 and 3F7; 5F4, L4 and 3F8; 5F5, L4 and 3F1; 5F5, L4 and 3F2; 5F5, L4 and 3F3; 5F5, L4 and 3F4; 5F5, L4 and 3F5; 5F5, L4 and 3F6; 5F5, L4 and 3F7; 5F5, L4 and 3F8; 5F6, L4 and 3F1; 5F6, L4 and 3F2; 5F6, L4 and 3F3; 5F6, L4 and 3F4; 5F6, L4 and 3F5; 5F6, L4 and 3F6; 5F6, L4 and 3F7; 5F6, L4 and 3F8; 5F7, L4 and 3F1; 5F7, L4 and 3F2; 5F7, L4 and 3F3; 5F7, L4 and 3F4; 5F7, L4 and 3F5; 5F7, L4 and 3F6; 5F7, L4 and 3F7; 5F7, L4 and 3F8; 5F8, L4 and 3F1; 5F8, L4 and 3F2; 5F8, L4 and 3F3; 5F8, L4 and 3F4; 5F8, L4 and 3F5; 5F8, L4 and 3F6; 5F8, L4 and 3F7; 5F8, L4 and 3F8; 5F9, L4 and 3F1; 5F9, L4 and 3F2; 5F9, L4 and 3F3; 5F9, L4 and 3F4; 5F9, L4 and 3F5; 5F9, L4 and 3F6; 5F9, L4 and 3F7; 5F9, L4 and 3F8; 5F1, L5 and 3F1; 5F1, L5 and 3F2; 5F1, L5 and 3F3; 5F1, L5 and 3F4; 5F1, L5 and 3F5; 5F1, L5 and 3F6; 5F1, L5 and 3F7; 5F1, L5 and 3F8; 5F2, L5 and 3F1; 5F2, L5 and 3F2; 5F2, L5 and 3F3; 5F2, L5 and 3F4; 5F2, L5 and 3F5; 5F2, L5 and 3F6; 5F2, L5 and 3F7; 5F2, L5 and 3F8; 5F3, L5 and 3F1; 5F3, L5 and 3F2; 5F3, L5 and 3F3; 5F3, L5 and 3F4; 5F3, L5 and 3F5; 5F3, L5 and 3F6; 5F3, L5 and 3F7; 5F3, L5 and 3F8; 5F4, L5 and 3F1; 5F4, L5 and 3F2; 5F4, L5 and 3F3; 5F4, L5 and 3F4; 5F4, L5 and 3F5; 5F4, L5 and 3F6; 5F4, L5 and 3F7; 5F4, L5 and 3F8; 5F5, L5 and 3F1; 5F5, L5 and 3F2; 5F5, L5 and 3F3; 5F5, L5 and 3F4; 5F5, L5 and 3F5; 5F5, L5 and 3F6; 5F5, L5 and 3F7; 5F5, L5 and 3F8; 5F6, L5 and 3F1; 5F6, L5 and 3F2; 5F6, L5 and 3F3; 5F6, L5 and 3F4; 5F6, L5 and 3F5; 5F6, L5 and 3F6; 5F6, L5 and 3F7; 5F6, L5 and 3F8; 5F7, L5 and 3F1; 5F7, L5 and 3F2; 5F7, L5 and 3F3; 5F7, L5 and 3F4; 5F7, L5 and 3F5; 5F7, L5 and 3F6; 5F7, L5 and 3F7; 5F7, L5 and 3F8; 5F8, L5 and 3F1; 5F8, L5 and 3F2; 5F8, L5 and 3F3; 5F8, L5 and 3F4; 5F8, L5 and 3F5; 5F8, L5 and 3F6; 5F8, L5 and 3F7; 5F8, L5 and 3F8; 5F9, L5 and 3F1; 5F9, L5 and 3F2; 5F9, L5 and 3F3; 5F9, L5 and 3F4; 5F9, L5 and 3F5; 5F9, L5 and 3F6; 5F9, L5 and 3F7; or 5F9, L5 and 3F8.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F3 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F4

5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F4 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one SFS 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F5 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F6 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F7 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F8 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F4 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F5 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F6 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F7 3' flanking region.

In one embodiment, the molecular scaffold may comprise at least one nucleic acid sequence encoding at least one 5F9 5' flanking region, at least one nucleic acid sequence encoding at least one L1 loop motif region, and at least one nucleic acid sequence encoding at least one 3F8 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F3 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F4 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one SFS 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F5

5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F5 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F6 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F7 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F8 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F3 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F4 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F5 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F6 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F7 3' flanking region.

In one embodiment, the molecular scaffold may comprise at least one nucleic acid sequence encoding at least one 5F9 5' flanking region, at least one nucleic acid sequence encoding at least one L2 loop motif region, and at least one nucleic acid sequence encoding at least one 3F8 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F1 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F3 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F4 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F5 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F6

5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F6 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F7 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F8 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F1 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F2 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F3 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F4 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F5 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F6 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F7 3' flanking region.

In one embodiment, the molecular scaffold may comprise at least one nucleic acid sequence encoding at least one 5F9 5' flanking region, at least one nucleic acid sequence encoding at least one L3 loop motif region, and at least one nucleic acid sequence encoding at least one 3F8 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F2 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one SFS 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F7

5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F8 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F2 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F3 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F6 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F7 3' flanking region.

In one embodiment, the molecular scaffold may comprise at least one nucleic acid sequence encoding at least one 5F9 5' flanking region, at least one nucleic acid sequence encoding at least one L4 loop motif region, and at least one nucleic acid sequence encoding at least one 3F8 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F1 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F2 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F4 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F5 5' flanking region, at least one nucleic acid sequence encoding at least one LS loop motif region, and at least one nucleic acid sequence encoding at least one 3F1 3' flanking region.

In one embodiment, the molecular scaffold may comprise at least one nucleic acid sequence encoding at least one 5F5 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F5 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F5 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F5 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one SFS 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one SFS 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F5 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F6 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F7 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F8

5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F8 5' flanking region, at least one nucleic acid sequence encoding at least one L5 loop motif region, and at least one nucleic acid sequence encoding at least one 3F8 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F2 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F3 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F5 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F6 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F7 3' flanking region.

In one embodiment, the molecular scaffold may comprise at least one nucleic acid sequence encoding at least one 5F9 5' flanking region, at least one nucleic acid sequence encoding at least one L5 loop motif region, and at least one nucleic acid sequence encoding at least one 3F8 3' flanking region.

In one embodiment, the molecular scaffold may comprise one or more linkers known in the art. The linkers may separate regions or one molecular scaffold from another. As a non-limiting example, the molecular scaffold may be polycistronic.

In one embodiment, the modulatory polynucleotide is designed using at least one of the following properties: loop variant, seed mismatch/bulge/wobble variant, stem mismatch, loop variant and vassal stem mismatch variant, seed mismatch and basal stem mismatch variant, stem mismatch and basal stem mismatch variant, seed wobble and basal stem wobble variant, or a stem sequence variant.

Figure 2:
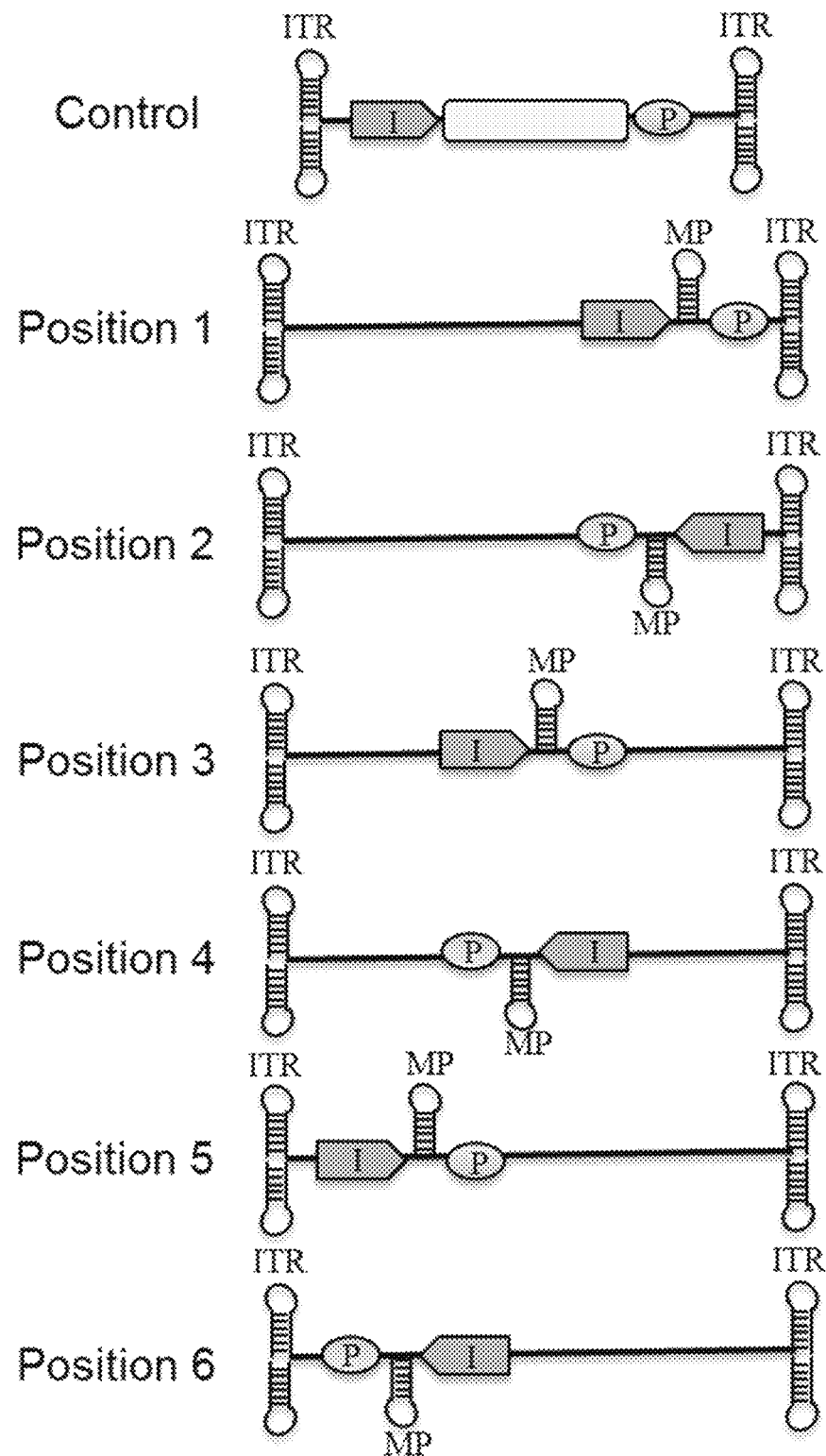
FIG. 2 is a diagram showing the location of the modulatory polynucleotide (MP) in relation to the ITRs, the intron (I) and the polyA (P).

In one embodiment, the molecular scaffold may be located between the two ITRs of an expression vector. As a non-limiting example, the molecular scaffold may be inserted into an expression vector at at least one of six different locations as shown in FIG. 2. In FIG. 2, "ITR" is the inverted terminal repeat, "I" represents intron, "P" is the polyA and "MP" is the modulatory polynucleotide.

In one embodiment, the molecular scaffold may be located downstream of a promoter such as, but not limited to, CMV, U6, H1, CBA or a CBA promoter with a SV40 or a human betaGlobin intron. Further, the molecular scaffold may also be located upstream of the polyadenylation sequence. As a non-limiting example, the molecular scaffold may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence. As another non-limiting example, the molecular scaffold may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence. As a non-limiting example, the molecular scaffold may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence. As another non-limiting example, the molecular scaffold may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence.

In one embodiment, the molecular scaffold may be located upstream of the polyadenylation sequence. Further, the molecular scaffold may be located downstream of a promoter such as, but not limited to, CMV, U6, H1, CBA or a CBA promoter with a SV40 or a human betaGlobin intron. As a non-limiting example, the molecular scaffold may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence. As another non-limiting example, the molecular scaffold may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence. As a non-limiting example, the molecular scaffold may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence. As another non-limiting example, the molecular scaffold may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence.

In one embodiment, the molecular scaffold may be located in a scAAV.

In one embodiment, the molecular scaffold may be located in an ssAAV.

In one embodiment, the molecular scaffold may be located near the 5' end of the flip ITR. In another embodiment, the molecular scaffold may be located near the 3' end of the flip ITR. In yet another embodiment, the molecular scaffold may be located near the 5' end of the flop ITR. In yet another embodiment, the molecular scaffold may be located near the 3' end of the flop ITR. In one embodiment, the molecular scaffold may be located between the 5' end of the flip ITR and the 3' end of the flop ITR. In one embodiment, the molecular scaffold may be located between (e.g., half-way between the 5' end of the flip ITR and 3' end of the flop ITR or the 3' end of the flop ITR and the 5' end of the flip ITR), the 3' end of the flip ITR and the 5' end of the flip ITR. As a non-limiting example, the molecular scaffold may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR). As a non-limiting example, the molecular scaffold may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR). As another non-limiting example, the molecular scaffold may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR). As another non-limiting example, the molecular scaffold may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR). As a non-limiting example, the molecular scaffold may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR). As another non-limiting example, the molecular scaffold may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR).

Vectors

In some embodiments, the siRNA molecules described herein can be encoded by vectors such as plasmids or viral vectors. In one embodiment, the siRNA molecules are encoded by viral vectors. Viral vectors may be, but are not limited to, Herpesvirus (HSV) vectors, retroviral vectors, adenoviral vectors, adeno-associated viral vectors, lentiviral vectors, and the like. In some specific embodiments, the viral vectors are AAV vectors.

Retroviral Vectors

In some embodiments, the siRNA duplex targeting SOD1 or HTT may be encoded by a retroviral vector (See, e.g., U.S. Pat. Nos. 5,399,346; 5,124,263; 4,650,764 and 4,980,289; the content of each of which are incorporated herein by reference in their entirety).

Adenoviral Vectors

Adenoviruses are eukaryotic DNA viruses that can be modified to efficiently deliver a nucleic acid to a variety of cell types in vivo, and have been used extensively in gene therapy protocols, including for targeting genes to neural cells. Various replication defective adenovirus and minimum adenovirus vectors have been described for nucleic acid therapeutics (See, e.g., PCT Patent Publication Nos. WO199426914, WO 199502697, WO199428152, WO199412649, WO199502697 and WO199622378; the content of each of which is incorporated by reference in their entirety). Such adenoviral vectors may also be used to deliver siRNA molecules of the present invention to cells.

Adeno-Associated Viral (AAV) Vectors

An adeno-associated virus (AAV) is a dependent parvovirus (like other parvoviruses) which is a single stranded non-enveloped DNA virus having a genome of about 5000 nucleotides in length and which contains two open reading frames encoding the proteins responsible for replication (Rep) and the structural protein of the capsid (Cap). The open reading frames are flanked by two Inverted Terminal Repeat (ITR) sequences, which serve as the origin of replication of the viral genome. Furthermore, the AAV genome contains a packaging sequence, allowing packaging of the viral genome into an AAV capsid. The AAV vector requires a co-helper (e.g., adenovirus) to undergo productive infection in infected cells. In the absence of such helper functions, the AAV virions essentially enter host cells but do not integrate into the cells' genome.

AAV vectors have been investigated for siRNA delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector and (v) the non-integrative nature in a host chromosome thereby reducing potential for long-term genetic alterations. Moreover, infection with AAV vectors has minimal influence on changing the pattern of cellular gene expression (Stilwell and Samulski et al., Biotechniques, 2003, 34, 148).

Typically, AAV vectors for siRNA delivery may be recombinant viral vectors which are replication defective as they lack sequences encoding functional Rep and Cap proteins within the viral genome. In some cases, the defective AAV vectors may lack most or all coding sequences and essentially only contains one or two AAV ITR sequences and a packaging sequence.

In one embodiment, the AAV vectors comprising a nucleic acid sequence encoding the siRNA molecules of the present invention may be introduced into mammalian cells.

AAV vectors may be modified to enhance the efficiency of delivery. Such modified AAV vectors comprising the nucleic acid sequence encoding the siRNA molecules of the present invention can be packaged efficiently and can be used to successfully infect the target cells at high frequency and with minimal toxicity.

In some embodiments, the AAV vector comprising a nucleic acid sequence encoding the siRNA molecules of the present invention may be a human serotype AAV vector. Such human AAV vector may be derived from any known serotype, e.g., from any one of serotypes AAV1-AAV11. As non-limiting examples, AAV vectors may be vectors comprising an AAV1-derived genome in an AAV1-derived capsid; vectors comprising an AAV2-derived genome in an AAV2-derived capsid; vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV vector comprising a nucleic acid sequence for encoding siRNA molecules of the present invention may be a pseudotyped hybrid or chimeric AAV vector which contains sequences and/or components originating from at least two different AAV serotypes. Pseudotyped AAV vectors may be vectors comprising an AAV genome derived from one AAV serotype and a capsid protein derived at least in part from a different AAV serotype. As non-limiting examples, such pseudotyped AAV vectors may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid. In like fashion, the present invention contemplates any hybrid or chimeric AAV vector.

In other embodiments, AAV vectors comprising a nucleic acid sequence encoding the siRNA molecules of the present invention may be used to deliver siRNA molecules to the central nervous system (e.g., U.S. Pat. No. 6,180,613; the contents of which is herein incorporated by reference in its entirety).

In some aspects, the AAV vectors comprising a nucleic acid sequence encoding the siRNA molecules of the present invention may further comprise a modified capsid including peptides from non-viral origin. In other aspects, the AAV vector may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In one embodiment, the AAV vector comprising a nucleic acid sequence encoding the siRNA molecules of the present invention may encode siRNA molecules which are polycistronic molecules. The siRNA molecules may additionally comprise one or more linkers between regions of the siRNA molecules.

Self-Complemtary and Single Strand Vectors

In one embodiment, the AAV vector used in the present invention is a single strand vector (ssAAV).

In another embodiment, the AAV vectors may be self-complementary AAV vectors (scAAVs). scAAV vectors contain both DNA strands which anneal together to form double stranded DNA. By skipping second strand synthesis, scAAVs allow for rapid expression in the cell.

In one embodiment, the AAV vector used in the present invention is a scAAV.

Methods for producing and/or modifying AAV vectors are disclosed in the art such as pseudotyped AAV vectors (International Patent Publication Nos. WO200028004; WO200123001; WO2004112727; WO 2005005610 and WO 2005072364, the content of each of which are incorporated herein by reference in their entirety).

AAV Serotypes

AAV particles of the present invention may comprise or be derived from any natural or recombinant AAV serotype. According to the present invention, the AAV particles may utilize or be based on a serotype selected from any of the following AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAVS-3/rh.57, AAVS-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33 .12/hu. 17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVCS, AAV-DJ, AAV-DJ8, AAVF3, AAVFS, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAVS, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVFS/HSC5, AAVF6/HSC6, AAVF7/HSC7, AAVF8/HSC8, AAVF9/HSC9, AAV-PHP.B (PHP.B), AAV-PHP.A (PHP.A), G2B-26, G2B-13, TH1.1-32 and/or TH1.1-35, and variants thereof. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9 (hu14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8. As a non-limiting example, the capsid of the recombinant AAV virus is AAV-PHP.B. As a non-limiting example, the capsid of the recombinant AAV virus is AAV-PHP.A.

In some embodiments, the AAV serotype may be, or have, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVCS (US20030138772 SEQ ID NO: 21), AAVF1 (US20030138772 SEQ ID NO: 22), AAVF3 (US20030138772 SEQ ID NO: 23), AAVFS (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-lb (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6):1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in United States Publication No. US20140359799, the contents of which are herein incorporated by reference in their entirety, such as but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAVS (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAVS-22/rh.58 (SEQ ID No: 27 of WO2005033321), AAVS-3/rh.57 (SEQ ID NO: 105 of WO2005033321), AAVS-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101-109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have, a sequence as described in United States Patent Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LKO2 (SEQ ID NO:3 of US20150376607), AAV-LKO3 (SEQ ID NO:4 of US20150376607), AAV-LKO4 (SEQ ID NO:5 of US20150376607), AAV-LKO5 (SEQ ID NO:6 of US20150376607), AAV-LKO6 (SEQ ID NO:7 of US20150376607), AAV-LKO7 (SEQ ID NO:8 of US20150376607), AAV-LKO8 (SEQ ID NO:9 of US20150376607), AAV-LKO9 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In one embodiment, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A;G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of US8734809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: 37 and 111 of U.S. Pat. No. 8,734,809), AAV CLv-R9 (SEQ ID NO: 38 and 112 of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734, 809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734, 809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734, 809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734, 809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8734809), AAV.hu.48R3 (SEQ ID NO: 183 of U.S. Pat. No. 8,734,809), or variants or derivatives thereof.

In some embodiments, the AAV serotype may be, or have, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAVS (SEQ ID NO: 50 and 100 of WO2016065001), or variants or derivatives thereof.

In one embodiment, the AAV may be a serotype comprising at least one AAV capsid CD8+ T-cell epitope. As a non-limiting example, the serotype may be AAV1, AAV2 or AAV8.

In one embodiment, the AAV may be a serotype selected from any of those found in Table 4.

In one embodiment, the AAV may comprise a sequence, fragment or variant thereof, of the sequences in Table 4.

In one embodiment, the AAV may be encoded by a sequence, fragment or variant as described in Table 4.

TABLE 4

AAV Serotypes

| Serotype | SEQ ID NO | Reference Information |
| --- | --- | --- |
| AAV1 | 28 | US20150159173 SEQ ID NO: 11, US20150315612 SEQ ID NO: 202 |
| AAV1 | 29 | US20160017295 SEQ ID NO: 1US20030138772 SEQ ID NO: 64, US20150159173 SEQ ID NO: 27, US20150315612 SEQ ID NO: 219, U.S. Pat. No. 7,198,951 SEQ ID NO: 5 |
| AAV1 | 30 | US20030138772 SEQ ID NO: 6 |
| AAV1.3 | 31 | US20030138772 SEQ ID NO: 14 |
| AAV10 | 32 | US20030138772 SEQ ID NO: 117 |
| AAV10 | 33 | WO2015121501 SEQ ID NO: 9 |
| AAV10 | 34 | WO2015121501 SEQ ID NO: 8 |
| AAV11 | 35 | US20030138772 SEQ ID NO: 118 |
| AAV12 | 36 | US20030138772 SEQ ID NO: 119 |
| AAV2 | 37 | US20150159173 SEQ ID NO: 7, US20150315612 SEQ ID NO: 211 |
| AAV2 | 38 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 39 | U.S. Pat. No. 6,156,303 SEQ ID NO: 8 |
| AAV2 | 40 | US20030138772 SEQ ID NO: 7 |
| AAV2 | 41 | U.S. Pat. No. 6,156,303 SEQ ID NO: 3 |
| AAV2.5T | 42 | U.S. Pat. No. 9,233,131 SEQ ID NO: 42 |

TABLE 4-continued

AAV Serotypes

| Serotype | SEQ ID NO | Reference Information |
|---|---|---|
| AAV223.10 | 43 | US20030138772 SEQ ID NO: 75 |
| AAV223.2 | 44 | US20030138772 SEQ ID NO: 49 |
| AAV223.2 | 45 | US20030138772 SEQ ID NO: 76 |
| AAV223.4 | 46 | US20030138772 SEQ ID NO: 50 |
| AAV223.4 | 47 | US20030138772 SEQ ID NO: 73 |
| AAV223.5 | 48 | US20030138772 SEQ ID NO: 51 |
| AAV223.5 | 49 | US20030138772 SEQ ID NO: 74 |
| AAV223.6 | 50 | US20030138772 SEQ ID NO: 52 |
| AAV223.6 | 51 | US20030138772 SEQ ID NO: 78 |
| AAV223.7 | 52 | US20030138772 SEQ ID NO: 53 |
| AAV223.7 | 53 | US20030138772 SEQ ID NO: 77 |
| AAV29.3 | 54 | US20030138772 SEQ ID NO: 82 |
| AAV29.4 | 55 | US20030138772 SEQ ID NO: 12 |
| AAV29.5 | 56 | US20030138772 SEQ ID NO: 83 |
| AAV29.5 (AAVbb.2) | 57 | US20030138772 SEQ ID NO: 13 |
| AAV3 | 58 | US20150159173 SEQ ID NO: 12 |
| AAV3 | 59 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 60 | US20030138772 SEQ ID NO: 8 |
| AAV3.3b | 61 | US20030138772 SEQ ID NO: 72 |
| AAV3-3 | 62 | US20150315612 SEQ ID NO: 200 |
| AAV3-3 | 63 | US20150315612 SEQ ID NO: 217 |
| AAV3a | 64 | U.S. Pat. No. 6,156,303 SEQ ID NO: 5 |
| AAV3a | 65 | U.S. Pat. No. 6,156,303 SEQ ID NO: 9 |
| AAV3b | 66 | U.S. Pat. No. 6,156,303 SEQ ID NO: 6 |
| AAV3b | 67 | U.S. Pat. No. 6,156,303 SEQ ID NO: 10 |
| AAV3b | 68 | U.S. Pat. No. 6,156,303 SEQ ID NO: 1 |
| AAV4 | 69 | US20140348794 SEQ ID NO: 17 |
| AAV4 | 70 | US20140348794 SEQ ID NO: 5 |
| AAV4 | 71 | US20140348794 SEQ ID NO: 3 |
| AAV4 | 72 | US20140348794 SEQ ID NO: 14 |
| AAV4 | 73 | US20140348794 SEQ ID NO: 15 |
| AAV4 | 74 | US20140348794 SEQ ID NO: 19 |
| AAV4 | 75 | US20140348794 SEQ ID NO: 12 |
| AAV4 | 76 | US20140348794 SEQ ID NO: 13 |
| AAV4 | 77 | US20140348794 SEQ ID NO: 7 |
| AAV4 | 78 | US20140348794 SEQ ID NO: 8 |
| AAV4 | 79 | US20140348794 SEQ ID NO: 9 |
| AAV4 | 80 | US20140348794 SEQ ID NO: 2 |
| AAV4 | 81 | US20140348794 SEQ ID NO: 10 |
| AAV4 | 82 | US20140348794 SEQ ID NO: 11 |
| AAV4 | 83 | US20140348794 SEQ ID NO: 18 |
| AAV4 | 84 | US20030138772 SEQ ID NO: 63, US20160017295 SEQ ID NO: 4, US20140348794 SEQ ID NO: 4 |
| AAV4 | 85 | US20140348794 SEQ ID NO: 16 |
| AAV4 | 86 | US20140348794 SEQ ID NO: 20 |
| AAV4 | 87 | US20140348794 SEQ ID NO: 6 |
| AAV4 | 88 | US20140348794 SEQ ID NO: 1 |
| AAV42.2 | 89 | US20030138772 SEQ ID NO: 9 |
| AAV42.2 | 90 | US20030138772 SEQ ID NO: 102 |
| AAV42.3b | 91 | US20030138772 SEQ ID NO: 36 |
| AAV42.3B | 92 | US20030138772 SEQ ID NO: 107 |
| AAV42.4 | 93 | US20030138772 SEQ ID NO: 33 |
| AAV42.4 | 94 | US20030138772 SEQ ID NO: 88 |
| AAV42.8 | 95 | US20030138772 SEQ ID NO: 27 |
| AAV42.8 | 96 | US20030138772 SEQ ID NO: 85 |
| AAV43.1 | 97 | US20030138772 SEQ ID NO: 39 |
| AAV43.1 | 98 | US20030138772 SEQ ID NO: 92 |
| AAV43.12 | 99 | US20030138772 SEQ ID NO: 41 |
| AAV43.12 | 100 | US20030138772 SEQ ID NO: 93 |
| AAV43.20 | 101 | US20030138772 SEQ ID NO: 42 |
| AAV43.20 | 102 | US20030138772 SEQ ID NO: 99 |
| AAV43.21 | 103 | US20030138772 SEQ ID NO: 43 |
| AAV43.21 | 104 | US20030138772 SEQ ID NO: 96 |
| AAV43.23 | 105 | US20030138772 SEQ ID NO: 44 |
| AAV43.23 | 106 | US20030138772 SEQ ID NO: 98 |
| AAV43.25 | 107 | US20030138772 SEQ ID NO: 45 |
| AAV43.25 | 108 | US20030138772 SEQ ID NO: 97 |
| AAV43.5 | 109 | US20030138772 SEQ ID NO: 40 |
| AAV43.5 | 110 | US20030138772 SEQ ID NO: 94 |
| AAV4-4 | 111 | US20150315612 SEQ ID NO: 201 |
| AAV4-4 | 112 | US20150315612 SEQ ID NO: 218 |
| AAV44.1 | 113 | US20030138772 SEQ ID NO: 46 |
| AAV44.1 | 114 | US20030138772 SEQ ID NO: 79 |
| AAV44.5 | 115 | US20030138772 SEQ ID NO: 47 |
| AAV44.5 | 116 | US20030138772 SEQ ID NO: 80 |
| AAV4407 | 117 | US20150315612 SEQ ID NO: 90 |
| AAV5 | 118 | U.S. Pat. No. 7,427,396 SEQ ID NO: 1 |
| AAV5 | 119 | US20030138772 SEQ ID NO: 114 |
| AAV5 | 120 | US20160017295 SEQ ID NO: 5, U.S. Pat. No. 7,427,396 SEQ ID NO: 2, US20150315612 SEQ ID NO: 216 |
| AAV5 | 121 | US20150315612 SEQ ID NO: 199 |
| AAV6 | 122 | US20150159173 SEQ ID NO: 13 |
| AAV6 | 123 | US20030138772 SEQ ID NO: 65, US20150159173 SEQ ID NO: 29, US20160017295 SEQ ID NO: 6, U.S. Pat. No. 6,156,303 SEQ ID NO: 7 |
| AAV6 | 124 | U.S. Pat. No. 6,156,303 SEQ ID NO: 11 |
| AAV6 | 125 | U.S. Pat. No. 6,156,303 SEQ ID NO: 2 |
| AAV6 | 126 | US20150315612 SEQ ID NO: 203 |
| AAV6 | 127 | US20150315612 SEQ ID NO: 220 |
| AAV6.1 | 128 | US20150159173 |
| AAV6.12 | 129 | US20150159173 |
| AAV6.2 | 130 | US20150159173 |
| AAV7 | 131 | US20150159173 SEQ ID NO: 14 |
| AAV7 | 132 | US20150315612 SEQ ID NO: 183 |
| AAV7 | 133 | US20030138772 SEQ ID NO: 2, US20150159173 SEQ ID NO: 30, US20150315612 SEQ ID NO: 181, US20160017295 SEQ ID NO: 7 |
| AAV7 | 134 | US20030138772 SEQ ID NO: 3 |
| AAV7 | 135 | US20030138772 SEQ ID NO: 1, US20150315612 SEQ ID NO: 180 |
| AAV7 | 136 | US20150315612 SEQ ID NO: 213 |
| AAV7 | 137 | US20150315612 SEQ ID NO: 222 |
| AAV8 | 138 | US20150159173 SEQ ID NO: 15 |
| AAV8 | 139 | US20150376240 SEQ ID NO: 7 |
| AAV8 | 140 | US20030138772 SEQ ID NO: 4, US20150315612 SEQ ID NO: 182 |
| AAV8 | 141 | US20030138772 SEQ ID NO: 95, US20140359799 SEQ ID NO: 1, US20150159173 SEQ ID NO: 31, US20160017295 SEQ ID NO: 8, U.S. Pat. No. 7,198,951 SEQ ID NO: 7, US20150315612 SEQ ID NO: 223 |
| AAV8 | 142 | US20150376240 SEQ ID NO: 8 |
| AAV8 | 143 | US20150315612 SEQ ID NO: 214 |
| AAV-8b | 144 | US20150376240 SEQ ID NO: 5 |
| AAV-8b | 145 | US20150376240 SEQ ID NO: 3 |
| AAV-8h | 146 | US20150376240 SEQ ID NO: 6 |
| AAV-8h | 147 | US20150376240 SEQ ID NO: 4 |
| AAV9 | 148 | US20030138772 SEQ ID NO: 5 |
| AAV9 | 149 | U.S. Pat. No. 7,198,951 SEQ ID NO: 1 |
| AAV9 | 150 | US20160017295 SEQ ID NO: 9 |
| AAV9 | 151 | US20030138772 SEQ ID NO: 100, U.S. Pat. No. 7,198,951 SEQ ID NO: 2 |
| AAV9 | 152 | U.S. Pat. No. 7,198,951 SEQ ID NO: 3 |
| AAV9 (AAVhu.14) | 153 | U.S. Pat. No. 7,906,111 SEQ ID NO: 3; WO2015038958 SEQ ID NO: 11 |
| AAV9 (AAVhu.14) | 154 | U.S. Pat. No. 7,906,111 SEQ ID NO: 123; WO2015038958 SEQ ID NO: 2 |
| AAVA3.1 | 155 | US20030138772 SEQ ID NO: 120 |
| AAVA3.3 | 156 | US20030138772 SEQ ID NO: 57 |
| AAVA3.3 | 157 | US20030138772 SEQ ID NO: 66 |
| AAVA3.4 | 158 | US20030138772 SEQ ID NO: 54 |
| AAVA3.4 | 159 | US20030138772 SEQ ID NO: 68 |
| AAVA3.5 | 160 | US20030138772 SEQ ID NO: 55 |
| AAVA3.5 | 161 | US20030138772 SEQ ID NO: 69 |
| AAVA3.7 | 162 | US20030138772 SEQ ID NO: 56 |
| AAVA3.7 | 163 | US20030138772 SEQ ID NO: 67 |
| AAV29.3 (AAVbb.1) | 164 | US20030138772 SEQ ID NO: 11 |
| AAVC2 | 165 | US20030138772 SEQ ID NO: 61 |
| AAVCh.5 | 166 | US20150159173 SEQ ID NO: 46, |

TABLE 4-continued

AAV Serotypes

| Serotype | SEQ ID NO | Reference Information |
|---|---|---|
| AAVcy.2 (AAV13.3) | 167 | US20150315612 SEQ ID NO: 234 US20030138772 SEQ ID NO: 15 |
| AAV24.1 | 168 | US20030138772 SEQ ID NO: 101 |
| AAVcy.3 (AAV24.1) | 169 | US20030138772 SEQ ID NO: 16 |
| AAV27.3 | 170 | US20030138772 SEQ ID NO: 104 |
| AAVcy.4 (AAV27.3) | 171 | US20030138772 SEQ ID NO: 17 |
| AAVcy.5 | 172 | US20150315612 SEQ ID NO: 227 |
| AAV7.2 | 173 | US20030138772 SEQ ID NO: 103 |
| AAVcy.5 (AAV7.2) | 174 | US20030138772 SEQ ID NO: 18 |
| AAV16.3 | 175 | US20030138772 SEQ ID NO: 105 |
| AAVcy.6 (AAV16.3) | 176 | US20030138772 SEQ ID NO: 10 |
| AAVCy.5 | 177 | US20150159173 SEQ ID NO: 8 |
| AAVcy.5 | 178 | US20150159173 SEQ ID NO: 24 |
| AAVCy.5R1 | 179 | US20150159173 |
| AAVCy.5R2 | 180 | US20150159173 |
| AAVCy.5R3 | 181 | US20150159173 |
| AAVCy.5R4 | 182 | US20150159173 |
| AAVDJ | 183 | US20140359799 SEQ ID NO: 3, U.S. Pat. No. 7,588,772 SEQ ID NO: 2 |
| AAVDJ | 184 | US20140359799 SEQ ID NO: 2, U.S. Pat. No. 7,588,772 SEQ ID NO: 1 |
| AAVDJ-8 | 185 | U.S. Pat. No. 7,588,772; Grimm et al 2008 |
| AAVDJ-8 | 186 | U.S. Pat. No. 7,588,772; Grimm et al 2008 |
| AAVF5 | 187 | US20030138772 SEQ ID NO: 110 |
| AAVH2 | 188 | US20030138772 SEQ ID NO: 26 |
| AAVH6 | 189 | US20030138772 SEQ ID NO: 25 |
| AAVhE1.1 | 190 | U.S. Pat. No. 9,233,131 SEQ ID NO: 44 |
| AAVhEr1.14 | 191 | U.S. Pat. No. 9,233,131 SEQ ID NO: 46 |
| AAVhEr1.16 | 192 | U.S. Pat. No. 9,233,131 SEQ ID NO: 48 |
| AAVhEr1.18 | 193 | U.S. Pat. No. 9,233,131 SEQ ID NO: 49 |
| AAVhEr1.23 (AAVhEr2.29) | 194 | U.S. Pat. No. 9,233,131 SEQ ID NO: 53 |
| AAVhEr1.35 | 195 | U.S. Pat. No. 9,233,131 SEQ ID NO: 50 |
| AAVhEr1.36 | 196 | U.S. Pat. No. 9,233,131 SEQ ID NO: 52 |
| AAVhEr1.5 | 197 | U.S. Pat. No. 9,233,131 SEQ ID NO: 45 |
| AAVhEr1.7 | 198 | U.S. Pat. No. 9,233,131 SEQ ID NO: 51 |
| AAVhEr1.8 | 199 | U.S. Pat. No. 9,233,131 SEQ ID NO: 47 |
| AAVhEr2.16 | 200 | U.S. Pat. No. 9,233,131 SEQ ID NO: 55 |
| AAVhEr2.30 | 201 | U.S. Pat. No. 9,233,131 SEQ ID NO: 56 |
| AAVhEr2.31 | 202 | U.S. Pat. No. 9,233,131 SEQ ID NO: 58 |
| AAVhEr2.36 | 203 | U.S. Pat. No. 9,233,131 SEQ ID NO: 57 |
| AAVhEr2.4 | 204 | U.S. Pat. No. 9,233,131 SEQ ID NO: 54 |
| AAVhEr3.1 | 205 | U.S. Pat. No. 9,233,131 SEQ ID NO: 59 |
| AAVhu.1 | 206 | US20150315612 SEQ ID NO: 46 |
| AAVhu.1 | 207 | US20150315612 SEQ ID NO: 144 |
| AAVhu.10 (AAV16.8) | 208 | US20150315612 SEQ ID NO: 56 |
| AAVhu.10 (AAV16.8) | 209 | US20150315612 SEQ ID NO: 156 |
| AAVhu.11 (AAV16.12) | 210 | US20150315612 SEQ ID NO: 57 |
| AAVhu.11 (AAV16.12) | 211 | US20150315612 SEQ ID NO: 153 |
| AAVhu.12 | 212 | US20150315612 SEQ ID NO: 59 |
| AAVhu.12 | 213 | US20150315612 SEQ ID NO: 154 |
| AAVhu.13 | 214 | US20150159173 SEQ ID NO: 16, US20150315612 SEQ ID NO: 71 |
| AAVhu.13 | 215 | US20150159173 SEQ ID NO: 32, US20150315612 SEQ ID NO: 129 |
| AAVhu.136.1 | 216 | US20150315612 SEQ ID NO: 165 |
| AAVhu.140.1 | 217 | US20150315612 SEQ ID NO: 166 |
| AAVhu.140.2 | 218 | US20150315612 SEQ ID NO: 167 |
| AAVhu.145.6 | 219 | US20150315612 SEQ ID No: 178 |
| AAVhu.15 | 220 | US20150315612 SEQ ID NO: 147 |
| AAVhu.15 (AAV33.4) | 221 | US20150315612 SEQ ID NO: 50 |
| AAVhu.156.1 | 222 | US20150315612 SEQ ID No: 179 |
| AAVhu.16 | 223 | US20150315612 SEQ ID NO: 148 |
| AAVhu.16 (AAV33.8) | 224 | US20150315612 SEQ ID NO: 51 |
| AAVhu.17 | 225 | US20150315612 SEQ ID NO: 83 |
| AAVhu.17 (AAV33.12) | 226 | US20150315612 SEQ ID NO: 4 |
| AAVhu.172.1 | 227 | US20150315612 SEQ ID NO: 171 |
| AAVhu.172.2 | 228 | US20150315612 SEQ ID NO: 172 |
| AAVhu.173.4 | 229 | US20150315612 SEQ ID NO: 173 |
| AAVhu.173.8 | 230 | US20150315612 SEQ ID NO: 175 |
| AAVhu.18 | 231 | US20150315612 SEQ ID NO: 52 |
| AAVhu.18 | 232 | US20150315612 SEQ ID NO: 149 |
| AAVhu.19 | 233 | US20150315612 SEQ ID NO: 62 |
| AAVhu.19 | 234 | US20150315612 SEQ ID NO: 133 |
| AAVhu.2 | 235 | US20150315612 SEQ ID NO: 48 |
| AAVhu.2 | 236 | US20150315612 SEQ ID NO: 143 |
| AAVhu.20 | 237 | US20150315612 SEQ ID NO: 63 |
| AAVhu.20 | 238 | US20150315612 SEQ ID NO: 134 |
| AAVhu.21 | 239 | US20150315612 SEQ ID NO: 65 |
| AAVhu.21 | 240 | US20150315612 SEQ ID NO: 135 |
| AAVhu.22 | 241 | US20150315612 SEQ ID NO: 67 |
| AAVhu.22 | 242 | US20150315612 SEQ ID NO: 138 |
| AAVhu.23 | 243 | US20150315612 SEQ ID NO: 60 |
| AAVhu.23.2 | 244 | US20150315612 SEQ ID NO: 137 |
| AAVhu.24 | 245 | US20150315612 SEQ ID NO: 66 |
| AAVhu.24 | 246 | US20150315612 SEQ ID NO: 136 |
| AAVhu.25 | 247 | US20150315612 SEQ ID NO: 49 |
| AAVhu.25 | 248 | US20150315612 SEQ ID NO: 146 |
| AAVhu.26 | 249 | US20150159173 SEQ ID NO: 17, US20150315612 SEQ ID NO: 61 |
| AAVhu.26 | 250 | US20150159173 SEQ ID NO: 33, US20150315612 SEQ ID NO: 139 |
| AAVhu.27 | 251 | US20150315612 SEQ ID NO: 64 |
| AAVhu.27 | 252 | US20150315612 SEQ ID NO: 140 |
| AAVhu.28 | 253 | US20150315612 SEQ ID NO: 68 |
| AAVhu.28 | 254 | US20150315612 SEQ ID NO: 130 |
| AAVhu.29 | 255 | US20150315612 SEQ ID NO: 69 |
| AAVhu.29 | 256 | US20150159173 SEQ ID NO: 42, US20150315612 SEQ ID NO: 132 |
| AAVhu.29 | 257 | US20150315612 SEQ ID NO: 225 |
| AAVhu.29R | 258 | US20150159173 |
| AAVhu.3 | 259 | US20150315612 SEQ ID NO: 44 |
| AAVhu.3 | 260 | US20150315612 SEQ ID NO: 145 |
| AAVhu.30 | 261 | US20150315612 SEQ ID NO: 70 |
| AAVhu.30 | 262 | US20150315612 SEQ ID NO: 131 |
| AAVhu.31 | 263 | US20150315612 SEQ ID NO: 1 |
| AAVhu.31 | 264 | US20150315612 SEQ ID NO: 121 |
| AAVhu.32 | 265 | US20150315612 SEQ ID NO: 2 |
| AAVhu.32 | 266 | US20150315612 SEQ ID NO: 122 |
| AAVhu.33 | 267 | US20150315612 SEQ ID NO: 75 |
| AAVhu.33 | 268 | US20150315612 SEQ ID NO: 124 |
| AAVhu.34 | 269 | US20150315612 SEQ ID NO: 72 |
| AAVhu.34 | 270 | US20150315612 SEQ ID NO: 125 |
| AAVhu.35 | 271 | US20150315612 SEQ ID NO: 73 |
| AAVhu.35 | 272 | US20150315612 SEQ ID NO: 164 |
| AAVhu.36 | 273 | US20150315612 SEQ ID NO: 74 |
| AAVhu.36 | 274 | US20150315612 SEQ ID NO: 126 |
| AAVhu.37 | 275 | US20150159173 SEQ ID NO: 34, US20150315612 SEQ ID NO: 88 |
| AAVhu.37 (AAV106.1) | 276 | US20150315612 SEQ ID NO: 10, US20150159173 SEQ ID NO: 18 |
| AAVhu.38 | 277 | US20150315612 SEQ ID NO: 161 |
| AAVhu.39 | 278 | US20150315612 SEQ ID NO: 102 |
| AAVhu.39 (AAVLG-9) | 279 | US20150315612 SEQ ID NO: 24 |
| AAVhu.4 | 280 | US20150315612 SEQ ID NO: 47 |
| AAVhu.4 | 281 | US20150315612 SEQ ID NO: 141 |
| AAVhu.40 | 282 | US20150315612 SEQ ID NO: 87 |
| AAVhu.40 (AAV114.3) | 283 | US20150315612 SEQ ID No: 11 |
| AAVhu.41 | 284 | US20150315612 SEQ ID NO: 91 |
| AAVhu.41 (AAV127.2) | 285 | US20150315612 SEQ ID NO: 6 |
| AAVhu.42 | 286 | US20150315612 SEQ ID NO: 85 |
| AAVhu.42 (AAV127.5) | 287 | US20150315612 SEQ ID NO: 8 |

TABLE 4-continued

AAV Serotypes

| Serotype | SEQ ID NO | Reference Information |
|---|---|---|
| AAVhu.43 | 288 | US20150315612 SEQ ID NO: 160 |
| AAVhu.43 | 289 | US20150315612 SEQ ID NO: 236 |
| AAVhu.43 (AAV128.1) | 290 | US20150315612 SEQ ID NO: 80 |
| AAVhu.44 | 291 | US20150159173 SEQ ID NO: 45, US20150315612 SEQ ID NO: 158 |
| AAVhu.44 (AAV128.3) | 292 | US20150315612 SEQ ID NO: 81 |
| AAVhu.44R1 | 293 | US20150159173 |
| AAVhu.44R2 | 294 | US20150159173 |
| AAVhu.44R3 | 295 | US20150159173 |
| AAVhu.45 | 296 | US20150315612 SEQ ID NO: 76 |
| AAVhu.45 | 297 | US20150315612 SEQ ID NO: 127 |
| AAVhu.46 | 298 | US20150315612 SEQ ID NO: 82 |
| AAVhu.46 | 299 | US20150315612 SEQ ID NO: 159 |
| AAVhu.46 | 300 | US20150315612 SEQ ID NO: 224 |
| AAVhu.47 | 301 | US20150315612 SEQ ID NO: 77 |
| AAVhu.47 | 302 | US20150315612 SEQ ID NO: 128 |
| AAVhu.48 | 303 | US20150159173 SEQ ID NO: 38 |
| AAVhu.48 | 304 | US20150315612 SEQ ID NO: 157 |
| AAVhu.48 (AAV130.4) | 305 | US20150315612 SEQ ID NO: 78 |
| AAVhu.48R1 | 306 | US20150159173 |
| AAVhu.48R2 | 307 | US20150159173 |
| AAVhu.48R3 | 308 | US20150159173 |
| AAVhu.49 | 309 | US20150315612 SEQ ID NO: 209 |
| AAVhu.49 | 310 | US20150315612 SEQ ID NO: 189 |
| AAVhu.5 | 311 | US20150315612 SEQ ID NO: 45 |
| AAVhu.5 | 312 | US20150315612 SEQ ID NO: 142 |
| AAVhu.51 | 313 | US20150315612 SEQ ID NO: 208 |
| AAVhu.51 | 314 | US20150315612 SEQ ID NO: 190 |
| AAVhu.52 | 315 | US20150315612 SEQ ID NO: 210 |
| AAVhu.52 | 316 | US20150315612 SEQ ID NO: 191 |
| AAVhu.53 | 317 | US20150159173 SEQ ID NO: 19 |
| AAVhu.53 | 318 | US20150159173 SEQ ID NO: 35 |
| AAVhu.53 (AAV145.1) | 319 | US20150315612 SEQ ID NO: 176 |
| AAVhu.54 | 320 | US20150315612 SEQ ID NO: 188 |
| AAVhu.54 (AAV145.5) | 321 | US20150315612 SEQ ID No: 177 |
| AAVhu.55 | 322 | US20150315612 SEQ ID NO: 187 |
| AAVhu.56 | 323 | US20150315612 SEQ ID NO: 205 |
| AAVhu.56 (AAV145.6) | 324 | US20150315612 SEQ ID NO: 168 |
| AAVhu.56 (AAV145.6) | 325 | US20150315612 SEQ ID NO: 192 |
| AAVhu.57 | 326 | US20150315612 SEQ ID NO: 206 |
| AAVhu.57 | 327 | US20150315612 SEQ ID NO: 169 |
| AAVhu.57 | 328 | US20150315612 SEQ ID NO: 193 |
| AAVhu.58 | 329 | US20150315612 SEQ ID NO: 207 |
| AAVhu.58 | 330 | US20150315612 SEQ ID NO: 194 |
| AAVhu.6 (AAV3.1) | 331 | US20150315612 SEQ ID NO: 5 |
| AAVhu.6 (AAV3.1) | 332 | US20150315612 SEQ ID NO: 84 |
| AAVhu.60 | 333 | US20150315612 SEQ ID NO: 184 |
| AAVhu.60 (AAV161.10) | 334 | US20150315612 SEQ ID NO: 170 |
| AAVhu.61 | 335 | US20150315612 SEQ ID NO: 185 |
| AAVhu.61 (AAV161.6) | 336 | US20150315612 SEQ ID NO: 174 |
| AAVhu.63 | 337 | US20150315612 SEQ ID NO: 204 |
| AAVhu.63 | 338 | US20150315612 SEQ ID NO: 195 |
| AAVhu.64 | 339 | US20150315612 SEQ ID NO: 212 |
| AAVhu.64 | 340 | US20150315612 SEQ ID NO: 196 |
| AAVhu.66 | 341 | US20150315612 SEQ ID NO: 197 |
| AAVhu.67 | 342 | US20150315612 SEQ ID NO: 215 |
| AAVhu.67 | 343 | US20150315612 SEQ ID NO: 198 |
| AAVhu.7 | 344 | US20150315612 SEQ ID NO: 226 |
| AAVhu.7 | 345 | US20150315612 SEQ ID NO: 150 |
| AAVhu.7 (AAV7.3) | 346 | US20150315612 SEQ ID NO: 55 |
| AAVhu.71 | 347 | US20150315612 SEQ ID NO: 79 |
| AAVhu.8 | 348 | US20150315612 SEQ ID NO: 53 |
| AAVhu.8 | 349 | US20150315612 SEQ ID NO: 12 |
| AAVhu.8 | 350 | US20150315612 SEQ ID NO: 151 |
| AAVhu.9 (AAV3.1) | 351 | US20150315612 SEQ ID NO: 58 |
| AAVhu.9 (AAV3.1) | 352 | US20150315612 SEQ ID NO: 155 |
| AAV-LK01 | 353 | US20150376607 SEQ ID NO: 2 |
| AAV-LK01 | 354 | US20150376607 SEQ ID NO: 29 |
| AAV-LK02 | 355 | US20150376607 SEQ ID NO: 3 |
| AAV-LK02 | 356 | US20150376607 SEQ ID NO: 30 |
| AAV-LK03 | 357 | US20150376607 SEQ ID NO: 4 |
| AAV-LK03 | 358 | WO2015121501 SEQ ID NO: 12, US20150376607 SEQ ID NO: 31 |
| AAV-LK04 | 359 | US20150376607 SEQ ID NO: 5 |
| AAV-LK04 | 360 | US20150376607 SEQ ID NO: 32 |
| AAV-LK05 | 361 | US20150376607 SEQ ID NO: 6 |
| AAV-LK05 | 362 | US20150376607 SEQ ID NO: 33 |
| AAV-LK06 | 363 | US20150376607 SEQ ID NO: 7 |
| AAV-LK06 | 364 | US20150376607 SEQ ID NO: 34 |
| AAV-LK07 | 365 | US20150376607 SEQ ID NO: 8 |
| AAV-LK07 | 366 | US20150376607 SEQ ID NO: 35 |
| AAV-LK08 | 367 | US20150376607 SEQ ID NO: 9 |
| AAV-LK08 | 368 | US20150376607 SEQ ID NO: 36 |
| AAV-LK09 | 369 | US20150376607 SEQ ID NO: 10 |
| AAV-LK09 | 370 | US20150376607 SEQ ID NO: 37 |
| AAV-LK10 | 371 | US20150376607 SEQ ID NO: 11 |
| AAV-LK10 | 372 | US20150376607 SEQ ID NO: 38 |
| AAV-LK11 | 373 | US20150376607 SEQ ID NO: 12 |
| AAV-LK11 | 374 | US20150376607 SEQ ID NO: 39 |
| AAV-LK12 | 375 | US20150376607 SEQ ID NO: 13 |
| AAV-LK12 | 376 | US20150376607 SEQ ID NO: 40 |
| AAV-LK13 | 377 | US20150376607 SEQ ID NO: 14 |
| AAV-LK13 | 378 | US20150376607 SEQ ID NO: 41 |
| AAV-LK14 | 379 | US20150376607 SEQ ID NO: 15 |
| AAV-LK14 | 380 | US20150376607 SEQ ID NO: 42 |
| AAV-LK15 | 381 | US20150376607 SEQ ID NO: 16 |
| AAV-LK15 | 382 | US20150376607 SEQ ID NO: 43 |
| AAV-LK16 | 383 | US20150376607 SEQ ID NO: 17 |
| AAV-LK16 | 384 | US20150376607 SEQ ID NO: 44 |
| AAV-LK17 | 385 | US20150376607 SEQ ID NO: 18 |
| AAV-LK17 | 386 | US20150376607 SEQ ID NO: 45 |
| AAV-LK18 | 387 | US20150376607 SEQ ID NO: 19 |
| AAV-LK18 | 388 | US20150376607 SEQ ID NO: 46 |
| AAV-LK19 | 389 | US20150376607 SEQ ID NO: 20 |
| AAV-LK19 | 390 | US20150376607 SEQ ID NO: 47 |
| AAV-PAEC | 391 | US20150376607 SEQ ID NO: 1 |
| AAV-PAEC | 392 | US20150376607 SEQ ID NO: 48 |
| AAV-PAEC11 | 393 | US20150376607 SEQ ID NO: 26 |
| AAV-PAEC11 | 394 | US20150376607 SEQ ID NO: 54 |
| AAV-PAEC12 | 395 | US20150376607 SEQ ID NO: 27 |
| AAV-PAEC12 | 396 | US20150376607 SEQ ID NO: 51 |
| AAV-PAEC13 | 397 | US20150376607 SEQ ID NO: 28 |
| AAV-PAEC13 | 398 | US20150376607 SEQ ID NO: 49 |
| AAV-PAEC2 | 399 | US20150376607 SEQ ID NO: 21 |
| AAV-PAEC2 | 400 | US20150376607 SEQ ID NO: 56 |
| AAV-PAEC4 | 401 | US20150376607 SEQ ID NO: 22 |
| AAV-PAEC4 | 402 | US20150376607 SEQ ID NO: 55 |
| AAV-PAEC6 | 403 | US20150376607 SEQ ID NO: 23 |
| AAV-PAEC6 | 404 | US20150376607 SEQ ID NO: 52 |
| AAV-PAEC7 | 405 | US20150376607 SEQ ID NO: 24 |
| AAV-PAEC7 | 406 | US20150376607 SEQ ID NO: 53 |
| AAV-PAEC8 | 407 | US20150376607 SEQ ID NO: 25 |
| AAV-PAEC8 | 408 | US20150376607 SEQ ID NO: 50 |
| AAVpi.1 | 409 | US20150315612 SEQ ID NO: 28 |
| AAVpi.1 | 410 | US20150315612 SEQ ID NO: 93 |
| AAVpi.2 | 411 | US20150315612 SEQ ID NO: 30 |
| AAVpi.2 | 412 | US20150315612 SEQ ID NO: 95 |
| AAVpi.3 | 413 | US20150315612 SEQ ID NO: 29 |
| AAVpi.3 | 414 | US20150315612 SEQ ID NO: 94 |
| AAVrh.10 | 415 | US20150159173 SEQ ID NO: 9 |
| AAVrh.10 | 416 | US20150159173 SEQ ID NO: 25 |
| AAV44.2 | 417 | US20030138772 SEQ ID NO: 59 |
| AAVrh.10 (AAV44.2) | 418 | US20030138772 SEQ ID NO: 81 |

TABLE 4-continued

AAV Serotypes

| Serotype | SEQ ID NO | Reference Information |
|---|---|---|
| AAV42.1B | 419 | US20030138772 SEQ ID NO: 90 |
| AAVrh.12 (AAV42.1b) | 420 | US20030138772 SEQ ID NO: 30 |
| AAVrh.13 | 421 | US20150159173 SEQ ID NO: 10 |
| AAVrh.13 | 422 | US20150159173 SEQ ID NO: 26 |
| AAVrh.13 | 423 | US20150315612 SEQ ID NO: 228 |
| AAVrh.13R | 424 | US20150159173 |
| AAV42.3A | 425 | US20030138772 SEQ ID NO: 87 |
| AAVrh.14 (AAV42.3a) | 426 | US20030138772 SEQ ID NO: 32 |
| AAV42.5A | 427 | US20030138772 SEQ ID NO: 89 |
| AAVrh.17 (AAV42.5a) | 428 | US20030138772 SEQ ID NO: 34 |
| AAV42.5B | 429 | US20030138772 SEQ ID NO: 91 |
| AAVrh.18 (AAV42.5b) | 430 | US20030138772 SEQ ID NO: 29 |
| AAV42.6B | 431 | US20030138772 SEQ ID NO: 112 |
| AAVrh.19 (AAV42.6b) | 432 | US20030138772 SEQ ID NO: 38 |
| AAVrh.2 | 433 | US20150159173 SEQ ID NO: 39 |
| AAVrh.2 | 434 | US20150315612 SEQ ID NO: 231 |
| AAVrh.20 | 435 | US20150159173 SEQ ID NO: 1 |
| AAV42.10 | 436 | US20030138772 SEQ ID NO: 106 |
| AAVrh.21 (AAV42.10) | 437 | US20030138772 SEQ ID NO: 35 |
| AAV42.11 | 438 | US20030138772 SEQ ID NO: 108 |
| AAVrh.22 (AAV42.11) | 439 | US20030138772 SEQ ID NO: 37 |
| AAV42.12 | 440 | US20030138772 SEQ ID NO: 113 |
| AAVrh.23 (AAV42.12) | 441 | US20030138772 SEQ ID NO: 58 |
| AAV42.13 | 442 | US20030138772 SEQ ID NO: 86 |
| AAVrh.24 (AAV42.13) | 443 | US20030138772 SEQ ID NO: 31 |
| AAV42.15 | 444 | US20030138772 SEQ ID NO: 84 |
| AAVrh.25 (AAV42.15) | 445 | US20030138772 SEQ ID NO: 28 |
| AAVrh.2R | 446 | US20150159173 |
| AAVrh.31 (AAV223.1) | 447 | US20030138772 SEQ ID NO: 48 |
| AAVC1 | 448 | US20030138772 SEQ ID NO: 60 |
| AAVrh.32 (AAVC1) | 449 | US20030138772 SEQ ID NO: 19 |
| AAVrh.32/33 | 450 | US20150159173 SEQ ID NO: 2 |
| AAVrh.33 (AAVC3) | 451 | US20030138772 SEQ ID NO: 20 |
| AAVC5 | 452 | US20030138772 SEQ ID NO: 62 |
| AAVrh.34 (AAVC5) | 453 | US20030138772 SEQ ID NO: 21 |
| AAVF1 | 454 | US20030138772 SEQ ID NO: 109 |
| AAVrh.35 (AAVF1) | 455 | US20030138772 SEQ ID NO: 22 |
| AAVF3 | 456 | US20030138772 SEQ ID NO: 111 |
| AAVrh.36 (AAVF3) | 457 | US20030138772 SEQ ID NO: 23 |
| AAVrh.37 | 458 | US20030138772 SEQ ID NO: 24 |
| AAVrh.37 | 459 | US20150159173 SEQ ID NO: 40 |
| AAVrh.37 | 460 | US20150315612 SEQ ID NO: 229 |
| AAVrh.37R2 | 461 | US20150159173 |
| AAVrh.38 (AAVLG-4) | 462 | US20150315612 SEQ ID NO: 7 |
| AAVrh.38 (AAVLG-4) | 463 | US20150315612 SEQ ID NO: 86 |
| AAVrh.39 | 464 | US20150159173 SEQ ID NO: 20, US20150315612 SEQ ID NO: 13 |
| AAVrh.39 | 465 | US20150159173 SEQ ID NO: 3, US20150159173 SEQ ID NO: 36, US20150315612 SEQ ID NO: 89 |
| AAVrh.40 | 466 | US20150315612 SEQ ID NO: 92 |
| AAVrh.40 (AAVLG-10) | 467 | US20150315612 SEQ ID No: 14 |
| AAVrh.43 (AAVN721-8) | 468 | US20150315612 SEQ ID NO: 43, US20150159173 SEQ ID NO: 21 |
| AAVrh.43 (AAVN721-8) | 469 | US20150315612 SEQ ID NO: 163, US20150159173 SEQ ID NO: 37 |
| AAVrh.44 | 470 | US20150315612 SEQ ID NO: 34 |
| AAVrh.44 | 471 | US20150315612 SEQ ID NO: 111 |
| AAVrh.45 | 472 | US20150315612 SEQ ID NO: 41 |
| AAVrh.45 | 473 | US20150315612 SEQ ID NO: 109 |
| AAVrh.46 | 474 | US20150159173 SEQ ID NO: 22, US20150315612 SEQ ID NO: 19 |
| AAVrh.46 | 475 | US20150159173 SEQ ID NO: 4, US20150315612 SEQ ID NO: 101 |
| AAVrh.47 | 476 | US20150315612 SEQ ID NO: 38 |
| AAVrh.47 | 477 | US20150315612 SEQ ID NO: 118 |
| AAVrh.48 | 478 | US20150159173 SEQ ID NO: 44, US20150315612 SEQ ID NO: 115 |
| AAVrh.48.1 | 479 | US20150159173 |
| AAVrh.48.1.2 | 480 | US20150159173 |
| AAVrh.48.2 | 481 | US20150159173 |
| AAVrh.48 (AAV1-7) | 482 | US20150315612 SEQ ID NO: 32 |
| AAVrh.49 (AAV1-8) | 483 | US20150315612 SEQ ID NO: 25 |
| AAVrh.49 (AAV1-8) | 484 | US20150315612 SEQ ID NO: 103 |
| AAVrh.50 (AAV2-4) | 485 | US20150315612 SEQ ID NO: 23 |
| AAVrh.50 (AAV2-4) | 486 | US20150315612 SEQ ID NO: 108 |
| AAVrh.51 (AAV2-5) | 487 | US20150315612 SEQ ID No: 22 |
| AAVrh.51 (AAV2-5) | 488 | US20150315612 SEQ ID NO: 104 |
| AAVrh.52 (AAV3-9) | 489 | US20150315612 SEQ ID NO: 18 |
| AAVrh.52 (AAV3-9) | 490 | US20150315612 SEQ ID NO: 96 |
| AAVrh.53 | 491 | US20150315612 SEQ ID NO: 97 |
| AAVrh.53 (AAV3-11) | 492 | US20150315612 SEQ ID NO: 17 |
| AAVrh.53 (AAV3-11) | 493 | US20150315612 SEQ ID NO: 186 |
| AAVrh.54 | 494 | US20150315612 SEQ ID NO: 40 |
| AAVrh.54 | 495 | US20150159173 SEQ ID NO: 49, US20150315612 SEQ ID NO: 116 |
| AAVrh.55 | 496 | US20150315612 SEQ ID NO: 37 |
| AAVrh.55 (AAV4-19) | 497 | US20150315612 SEQ ID NO: 117 |
| AAVrh.56 | 498 | US20150315612 SEQ ID NO: 54 |
| AAVrh.56 | 499 | US20150315612 SEQ ID NO: 152 |
| AAVrh.57 | 500 | US20150315612 SEQ ID NO: 26 |
| AAVrh.57 | 501 | US20150315612 SEQ ID NO: 105 |
| AAVrh.58 | 502 | US20150315612 SEQ ID NO: 27 |
| AAVrh.58 | 503 | US20150159173 SEQ ID NO: 48, US20150315612 SEQ ID NO: 106 |
| AAVrh.58 | 504 | US20150315612 SEQ ID NO: 232 |
| AAVrh.59 | 505 | US20150315612 SEQ ID NO: 42 |
| AAVrh.59 | 506 | US20150315612 SEQ ID NO: 110 |
| AAVrh.60 | 507 | US20150315612 SEQ ID NO: 31 |
| AAVrh.60 | 508 | US20150315612 SEQ ID NO: 120 |
| AAVrh.61 | 509 | US20150315612 SEQ ID NO: 107 |
| AAVrh.61 (AAV2-3) | 510 | US20150315612 SEQ ID NO: 21 |
| AAVrh.62 (AAV2-15) | 511 | US20150315612 SEQ ID No: 33 |
| AAVrh.62 (AAV2-15) | 512 | US20150315612 SEQ ID NO: 114 |
| AAVrh.64 | 513 | US20150315612 SEQ ID No: 15 |
| AAVrh.64 | 514 | US20150159173 SEQ ID NO: 43, US20150315612 SEQ ID NO: 99 |
| AAVrh.64 | 515 | US20150315612 SEQ ID NO: 233 |
| AAVRh.64R1 | 516 | US20150159173 |
| AAVRh.64R2 | 517 | US20150159173 |
| AAVrh.65 | 518 | US20150315612 SEQ ID NO: 35 |
| AAVrh.65 | 519 | US20150315612 SEQ ID NO: 112 |
| AAVrh.67 | 520 | US20150315612 SEQ ID NO: 36 |
| AAVrh.67 | 521 | US20150315612 SEQ ID NO: 230 |
| AAVrh.67 | 522 | US20150159173 SEQ ID NO: 47, US20150315612 SEQ ID NO: 113 |

TABLE 4-continued

AAV Serotypes

| Serotype | SEQ ID NO | Reference Information |
|---|---|---|
| AAVrh.68 | 523 | US20150315612 SEQ ID NO: 16 |
| AAVrh.68 | 524 | US20150315612 SEQ ID NO: 100 |
| AAVrh.69 | 525 | US20150315612 SEQ ID NO: 39 |
| AAVrh.69 | 526 | US20150315612 SEQ ID NO: 119 |
| AAVrh.70 | 527 | US20150315612 SEQ ID NO: 20 |
| AAVrh.70 | 528 | US20150315612 SEQ ID NO: 98 |
| AAVrh.71 | 529 | US20150315612 SEQ ID NO: 162 |
| AAVrh.72 | 530 | US20150315612 SEQ ID NO: 9 |
| AAVrh.73 | 531 | US20150159173 SEQ ID NO: 5 |
| AAVrh.74 | 532 | US20150159173 SEQ ID NO: 6 |
| AAVrh.8 | 533 | US20150159173 SEQ ID NO: 41 |
| AAVrh.8 | 534 | US20150315612 SEQ ID NO: 235 |
| AAVrh.8R | 535 | US20150159173, WO2015168666 SEQ ID NO: 9 |
| AAVrh.8R A586R mutant | 536 | WO2015168666 SEQ ID NO: 10 |
| AAVrh.8R R533A mutant | 537 | WO2015168666 SEQ ID NO: 11 |
| BAAV (bovine AAV) | 538 | U.S. Pat. No. 9,193,769 SEQ ID NO: 8 |
| BAAV (bovine AAV) | 539 | U.S. Pat. No. 9,193,769 SEQ ID NO: 10 |
| BAAV (bovine AAV) | 540 | U.S. Pat. No. 9,193,769 SEQ ID NO: 4 |
| BAAV (bovine AAV) | 541 | U.S. Pat. No. 9,193,769 SEQ ID NO: 2 |
| BAAV (bovine AAV) | 542 | U.S. Pat. No. 9,193,769 SEQ ID NO: 6 |
| BAAV (bovine AAV) | 543 | U.S. Pat. No. 9,193,769 SEQ ID NO: 1 |
| BAAV (bovine AAV) | 544 | U.S. Pat. No. 9,193,769 SEQ ID NO: 5 |
| BAAV (bovine AAV) | 545 | U.S. Pat. No. 9,193,769 SEQ ID NO: 3 |
| BAAV (bovine AAV) | 546 | U.S. Pat. No. 9,193,769 SEQ ID NO: 11 |
| BAAV (bovine AAV) | 547 | U.S. Pat. No. 7,427,396 SEQ ID NO: 5 |
| BAAV (bovine AAV) | 548 | U.S. Pat. No. 7,427,396 SEQ ID NO: 6 |
| BAAV (bovine AAV) | 549 | U.S. Pat. No. 9,193,769 SEQ ID NO: 7 |
| BAAV (bovine AAV) | 550 | U.S. Pat. No. 9,193,769 SEQ ID NO: 9 |
| BNP61 AAV | 551 | US20150238550 SEQ ID NO: 1 |
| BNP61 AAV | 552 | US20150238550 SEQ ID NO: 2 |
| BNP62 AAV | 553 | US20150238550 SEQ ID NO: 3 |
| BNP63 AAV | 554 | US20150238550 SEQ ID NO: 4 |
| caprine AAV | 555 | U.S. Pat. No. 7,427,396 SEQ ID NO: 3 |
| caprine AAV | 556 | U.S. Pat. No. 7,427,396 SEQ ID NO: 4 |
| true type AAV (ttAAV) | 557 | WO2015121501 SEQ ID NO: 2 |
| AAAV (Avian AAV) | 558 | U.S. Pat. No. 9,238,800 SEQ ID NO: 12 |
| AAAV (Avian AAV) | 559 | U.S. Pat. No. 9,238,800 SEQ ID NO: 2 |
| AAAV (Avian AAV) | 560 | U.S. Pat. No. 9,238,800 SEQ ID NO: 6 |
| AAAV (Avian AAV) | 561 | U.S. Pat. No. 9,238,800 SEQ ID NO: 4 |
| AAAV (Avian AAV) | 562 | U.S. Pat. No. 9,238,800 SEQ ID NO: 8 |
| AAAV (Avian AAV) | 563 | U.S. Pat. No. 9,238,800 SEQ ID NO: 14 |
| AAAV (Avian AAV) | 564 | U.S. Pat. No. 9,238,800 SEQ ID NO: 10 |
| AAAV (Avian AAV) | 565 | U.S. Pat. No. 9,238,800 SEQ ID NO: 15 |
| AAAV (Avian AAV) | 566 | U.S. Pat. No. 9,238,800 SEQ ID NO: 5 |
| AAAV (Avian AAV) | 567 | U.S. Pat. No. 9,238,800 SEQ ID NO: 9 |
| AAAV (Avian AAV) | 568 | U.S. Pat. No. 9,238,800 SEQ ID NO: 3 |
| AAAV (Avian AAV) | 569 | U.S. Pat. No. 9,238,800 SEQ ID NO: 7 |
| AAAV (Avian AAV) | 570 | U.S. Pat. No. 9,238,800 SEQ ID NO: 11 |
| AAAV (Avian AAV) | 571 | U.S. Pat. No. 9,238,800 SEQ ID NO: 13 |
| AAAV (Avian AAV) | 572 | U.S. Pat. No. 9,238,800 SEQ ID NO: 1 |
| AAV Shuffle 100-1 | 573 | US20160017295 SEQ ID NO: 23 |
| AAV Shuffle 100-1 | 574 | US20160017295 SEQ ID NO: 11 |
| AAV Shuffle 100-2 | 575 | US20160017295 SEQ ID NO: 37 |
| AAV Shuffle 100-2 | 576 | US20160017295 SEQ ID NO: 29 |
| AAV Shuffle 100-3 | 577 | US20160017295 SEQ ID NO: 24 |
| AAV Shuffle 100-3 | 578 | US20160017295 SEQ ID NO: 12 |
| AAV Shuffle 100-7 | 579 | US20160017295 SEQ ID NO: 25 |
| AAV Shuffle 100-7 | 580 | US20160017295 SEQ ID NO: 13 |
| AAV Shuffle 10-2 | 581 | US20160017295 SEQ ID NO: 34 |
| AAV Shuffle 10-2 | 582 | US20160017295 SEQ ID NO: 26 |
| AAV Shuffle 10-6 | 583 | US20160017295 SEQ ID NO: 35 |
| AAV Shuffle 10-6 | 584 | US20160017295 SEQ ID NO: 27 |
| AAV Shuffle 10-8 | 585 | US20160017295 SEQ ID NO: 36 |
| AAV Shuffle 10-8 | 586 | US20160017295 SEQ ID NO: 28 |
| AAV SM 100-10 | 587 | US20160017295 SEQ ID NO: 41 |
| AAV SM 100-10 | 588 | US20160017295 SEQ ID NO: 33 |
| AAV SM 100-3 | 589 | US20160017295 SEQ ID NO: 40 |
| AAV SM 100-3 | 590 | US20160017295 SEQ ID NO: 32 |
| AAV SM 10-1 | 591 | US20160017295 SEQ ID NO: 38 |
| AAV SM 10-1 | 592 | US20160017295 SEQ ID NO: 30 |
| AAV SM 10-2 | 593 | US20160017295 SEQ ID NO: 10 |
| AAV SM 10-2 | 594 | US20160017295 SEQ ID NO: 22 |
| AAV SM 10-8 | 595 | US20160017295 SEQ ID NO: 39 |
| AAV SM 10-8 | 596 | US20160017295 SEQ ID NO: 31 |
| AAV SM 100-10 | 587 | US20160017295 SEQ ID NO: 41 |
| AAV SM 100-10 | 588 | US20160017295 SEQ ID NO: 33 |
| AAV SM 100-3 | 589 | US20160017295 SEQ ID NO: 40 |
| AAV SM 100-3 | 590 | US20160017295 SEQ ID NO: 32 |
| AAV SM 10-1 | 591 | US20160017295 SEQ ID NO: 38 |
| AAV SM 10-1 | 592 | US20160017295 SEQ ID NO: 30 |
| AAV SM 10-2 | 593 | US20160017295 SEQ ID NO: 10 |
| AAV SM 10-2 | 594 | US20160017295 SEQ ID NO: 22 |
| AAV SM 10-8 | 595 | US20160017295 SEQ ID NO: 39 |
| AAV SM 10-8 | 596 | US20160017295 SEQ ID NO: 31 |
| AAVF1/HSC1 | 597 | WO2016049230 SEQ ID NO: 20 |
| AAVF2/HSC2 | 598 | WO2016049230 SEQ ID NO: 21 |
| AAVF3/HSC3 | 599 | WO2016049230 SEQ ID NO: 22 |
| AAVF4/HSC4 | 600 | WO2016049230 SEQ ID NO: 23 |
| AAVF5/HSC5 | 601 | WO2016049230 SEQ ID NO: 25 |
| AAVF6/HSC6 | 602 | WO2016049230 SEQ ID NO: 24 |
| AAVF7/HSC7 | 603 | WO2016049230 SEQ ID NO: 27 |
| AAVF8/HSC8 | 604 | WO2016049230 SEQ ID NO: 28 |
| AAVF9/HSC9 | 605 | WO2016049230 SEQ ID NO: 29 |
| AAVF11/HSC11 | 606 | WO2016049230 SEQ ID NO: 26 |
| AAVF12/HSC12 | 607 | WO2016049230 SEQ ID NO: 30 |
| AAVF13/HSC13 | 608 | WO2016049230 SEQ ID NO: 31 |
| AAVF14/HSC14 | 609 | WO2016049230 SEQ ID NO: 32 |
| AAVF15/HSC15 | 610 | WO2016049230 SEQ ID NO: 33 |
| AAVF16/HSC16 | 611 | WO2016049230 SEQ ID NO: 34 |
| AAVF17/HSC17 | 612 | WO2016049230 SEQ ID NO: 35 |
| AAVF1/HSC1 | 613 | WO2016049230 SEQ ID NO: 2 |
| AAVF2/HSC2 | 614 | WO2016049230 SEQ ID NO: 3 |
| AAVF3/HSC3 | 615 | WO2016049230 SEQ ID NO: 5 |
| AAVF4/HSC4 | 616 | WO2016049230 SEQ ID NO: 6 |
| AAVF5/HSC5 | 617 | WO2016049230 SEQ ID NO: 11 |
| AAVF6/HSC6 | 618 | WO2016049230 SEQ ID NO: 7 |
| AAVF7/HSC7 | 619 | WO2016049230 SEQ ID NO: 8 |
| AAVF8/HSC8 | 620 | WO2016049230 SEQ ID NO: 9 |
| AAVF9/HSC9 | 621 | WO2016049230 SEQ ID NO: 10 |

TABLE 4-continued

AAV Serotypes

| Serotype | SEQ ID NO | Reference Information |
|---|---|---|
| AAVF11/HSC11 | 622 | WO2016049230 SEQ ID NO: 4 |
| AAVF12/HSC12 | 623 | WO2016049230 SEQ ID NO: 12 |
| AAVF13/HSC13 | 624 | WO2016049230 SEQ ID NO: 14 |
| AAVF14/HSC14 | 625 | WO2016049230 SEQ ID NO: 15 |
| AAVF15/HSC15 | 626 | WO2016049230 SEQ ID NO: 16 |
| AAVF16/HSC16 | 627 | WO2016049230 SEQ ID NO: 17 |
| AAVF17/HSC17 | 628 | WO2016049230 SEQ ID NO: 13 |
| AAV CBr-E1 | 629 | U.S. Pat. No. 8,734,809 SEQ ID NO: 13 |
| AAV CBr-E2 | 630 | U.S. Pat. No. 8,734,809 SEQ ID NO: 14 |
| AAV CBr-E3 | 631 | U.S. Pat. No. 8,734,809 SEQ ID NO: 15 |
| AAV CBr-E4 | 632 | U.S. Pat. No. 8,734,809 SEQ ID NO: 16 |
| AAV CBr-E5 | 633 | U.S. Pat. No. 8,734,809 SEQ ID NO: 17 |
| AAV CBr-e5 | 634 | U.S. Pat. No. 8,734,809 SEQ ID NO: 18 |
| AAV CBr-E6 | 635 | U.S. Pat. No. 8,734,809 SEQ ID NO: 19 |
| AAV CBr-E7 | 636 | U.S. Pat. No. 8,734,809 SEQ ID NO: 20 |
| AAV CBr-E8 | 637 | U.S. Pat. No. 8,734,809 SEQ ID NO: 21 |
| AAV CLv-D1 | 638 | U.S. Pat. No. 8,734,809 SEQ ID NO: 22 |
| AAV CLv-D2 | 639 | U.S. Pat. No. 8,734,809 SEQ ID NO: 23 |
| AAV CLv-D3 | 640 | U.S. Pat. No. 8,734,809 SEQ ID NO: 24 |
| AAV CLv-D4 | 641 | U.S. Pat. No. 8,734,809 SEQ ID NO: 25 |
| AAV CLv-D5 | 642 | U.S. Pat. No. 8,734,809 SEQ ID NO: 26 |
| AAV CLv-D6 | 643 | U.S. Pat. No. 8,734,809 SEQ ID NO: 27 |
| AAV CLv-D7 | 644 | U.S. Pat. No. 8,734,809 SEQ ID NO: 28 |
| AAV CLv-D8 | 645 | U.S. Pat. No. 8,734,809 SEQ ID NO: 29 |
| AAV CLv-E1 | 646 | U.S. Pat. No. 8,734,809 SEQ ID NO: 13 |
| AAV CLv-R1 | 647 | U.S. Pat. No. 8,734,809 SEQ ID NO: 30 |
| AAV CLv-R2 | 648 | U.S. Pat. No. 8,734,809 SEQ ID NO: 31 |
| AAV CLv-R3 | 649 | U.S. Pat. No. 8,734,809 SEQ ID NO: 32 |
| AAV CLv-R4 | 650 | U.S. Pat. No. 8,734,809 SEQ ID NO: 33 |
| AAV CLv-R5 | 651 | U.S. Pat. No. 8,734,809 SEQ ID NO: 34 |
| AAV CLv-R6 | 652 | U.S. Pat. No. 8,734,809 SEQ ID NO: 35 |
| AAV CLv-R7 | 653 | U.S. Pat. No. 8,734,809 SEQ ID NO: 36 |
| AAV CLv-R8 | 654 | U.S. Pat. No. 8,734,809 SEQ ID NO: 37 |
| AAV CLv-R9 | 655 | U.S. Pat. No. 8,734,809 SEQ ID NO: 38 |
| AAV CLg-F1 | 656 | U.S. Pat. No. 8,734,809 SEQ ID NO: 39 |
| AAV CLg-F2 | 657 | U.S. Pat. No. 8,734,809 SEQ ID NO: 40 |
| AAV CLg-F3 | 658 | U.S. Pat. No. 8,734,809 SEQ ID NO: 41 |
| AAV CLg-F4 | 659 | U.S. Pat. No. 8,734,809 SEQ ID NO: 42 |
| AAV CLg-F5 | 660 | U.S. Pat. No. 8,734,809 SEQ ID NO: 43 |
| AAV CLg-F6 | 661 | U.S. Pat. No. 8,734,809 SEQ ID NO: 43 |
| AAV CLg-F7 | 662 | U.S. Pat. No. 8,734,809 SEQ ID NO: 44 |
| AAV CLg-F8 | 663 | U.S. Pat. No. 8,734,809 SEQ ID NO: 43 |
| AAV CSp-1 | 664 | U.S. Pat. No. 8,734,809 SEQ ID NO: 45 |
| AAV CSp-10 | 665 | U.S. Pat. No. 8,734,809 SEQ ID NO: 46 |
| AAV CSp-11 | 666 | U.S. Pat. No. 8,734,809 SEQ ID NO: 47 |
| AAV CSp-2 | 667 | U.S. Pat. No. 8,734,809 SEQ ID NO: 48 |
| AAV CSp-3 | 668 | U.S. Pat. No. 8,734,809 SEQ ID NO: 49 |
| AAV CSp-4 | 669 | U.S. Pat. No. 8,734,809 SEQ ID NO: 50 |
| AAV CSp-6 | 670 | U.S. Pat. No. 8,734,809 SEQ ID NO: 51 |
| AAV CSp-7 | 671 | U.S. Pat. No. 8,734,809 SEQ ID NO: 52 |
| AAV CSp-8 | 672 | U.S. Pat. No. 8,734,809 SEQ ID NO: 53 |
| AAV CSp-9 | 673 | U.S. Pat. No. 8,734,809 SEQ ID NO: 54 |
| AAV CHt-2 | 674 | U.S. Pat. No. 8,734,809 SEQ ID NO: 55 |
| AAV CHt-3 | 675 | U.S. Pat. No. 8,734,809 SEQ ID NO: 56 |
| AAV CKd-1 | 676 | U.S. Pat. No. 8,734,809 SEQ ID NO: 57 |
| AAV CKd-10 | 677 | U.S. Pat. No. 8,734,809 SEQ ID NO: 58 |
| AAV CKd-2 | 678 | U.S. Pat. No. 8,734,809 SEQ ID NO: 59 |
| AAV CKd-3 | 679 | U.S. Pat. No. 8,734,809 SEQ ID NO: 60 |
| AAV CKd-4 | 680 | U.S. Pat. No. 8,734,809 SEQ ID NO: 61 |
| AAV CKd-6 | 681 | U.S. Pat. No. 8,734,809 SEQ ID NO: 62 |
| AAV CKd-7 | 682 | U.S. Pat. No. 8,734,809 SEQ ID NO: 63 |
| AAV CKd-8 | 683 | U.S. Pat. No. 8,734,809 SEQ ID NO: 64 |
| AAV CLv-1 | 684 | U.S. Pat. No. 8,734,809 SEQ ID NO: 65 |
| AAV CLv-12 | 685 | U.S. Pat. No. 8,734,809 SEQ ID NO: 66 |
| AAV CLv-13 | 686 | U.S. Pat. No. 8,734,809 SEQ ID NO: 67 |
| AAV CLv-2 | 687 | U.S. Pat. No. 8,734,809 SEQ ID NO: 68 |
| AAV CLv-3 | 688 | U.S. Pat. No. 8,734,809 SEQ ID NO: 69 |
| AAV CLv-4 | 689 | U.S. Pat. No. 8,734,809 SEQ ID NO: 70 |
| AAV CLv-6 | 690 | U.S. Pat. No. 8,734,809 SEQ ID NO: 71 |
| AAV CLv-8 | 691 | U.S. Pat. No. 8,734,809 SEQ ID NO: 72 |
| AAV CKd-B1 | 692 | U.S. Pat. No. 8,734,809 SEQ ID NO: 73 |
| AAV CKd-B2 | 693 | U.S. Pat. No. 8,734,809 SEQ ID NO: 74 |
| AAV CKd-B3 | 694 | U.S. Pat. No. 8,734,809 SEQ ID NO: 75 |
| AAV CKd-B4 | 695 | U.S. Pat. No. 8,734,809 SEQ ID NO: 76 |
| AAV CKd-B5 | 696 | U.S. Pat. No. 8,734,809 SEQ ID NO: 77 |
| AAV CKd-B6 | 697 | U.S. Pat. No. 8,734,809 SEQ ID NO: 78 |
| AAV CKd-B7 | 698 | U.S. Pat. No. 8,734,809 SEQ ID NO: 79 |
| AAV CKd-B8 | 699 | U.S. Pat. No. 8,734,809 SEQ ID NO: 80 |
| AAV CKd-H1 | 700 | U.S. Pat. No. 8,734,809 SEQ ID NO: 81 |
| AAV CKd-H2 | 701 | U.S. Pat. No. 8,734,809 SEQ ID NO: 82 |
| AAV CKd-H3 | 702 | U.S. Pat. No. 8,734,809 SEQ ID NO: 83 |
| AAV CKd-H4 | 703 | U.S. Pat. No. 8,734,809 SEQ ID NO: 84 |
| AAV CKd-H5 | 704 | U.S. Pat. No. 8,734,809 SEQ ID NO: 85 |
| AAV CKd-H6 | 705 | U.S. Pat. No. 8,734,809 SEQ ID NO: 77 |
| AAV CHt-1 | 706 | U.S. Pat. No. 8,734,809 SEQ ID NO: 86 |
| AAV CLv1-1 | 707 | U.S. Pat. No. 8,734,809 SEQ ID NO: 171 |
| AAV CLv1-2 | 708 | U.S. Pat. No. 8,734,809 SEQ ID NO: 172 |
| AAV CLv1-3 | 709 | U.S. Pat. No. 8,734,809 SEQ ID NO: 173 |
| AAV CLv1-4 | 710 | U.S. Pat. No. 8,734,809 SEQ ID NO: 174 |
| AAV Clv1-7 | 711 | U.S. Pat. No. 8,734,809 SEQ ID NO: 175 |
| AAV Clv1-8 | 712 | U.S. Pat. No. 8,734,809 SEQ ID NO: 176 |
| AAV Clv1-9 | 713 | U.S. Pat. No. 8,734,809 SEQ ID NO: 177 |
| AAV Clv1-10 | 714 | U.S. Pat. No. 8,734,809 SEQ ID NO: 178 |
| AAV. VR-355 | 715 | U.S. Pat. No. 8,734,809 SEQ ID NO: 181 |
| AAV.hu.48R3 | 716 | U.S. Pat. No. 8,734,809 SEQ ID NO: 183 |
| AAV CBr-E1 | 717 | U.S. Pat. No. 8,734,809 SEQ ID NO: 87 |
| AAV CBr-E2 | 718 | U.S. Pat. No. 8,734,809 SEQ ID NO: 88 |
| AAV CBr-E3 | 719 | U.S. Pat. No. 8,734,809 SEQ ID NO: 89 |
| AAV CBr-E4 | 720 | U.S. Pat. No. 8,734,809 SEQ ID NO: 90 |
| AAV CBr-E5 | 721 | U.S. Pat. No. 8,734,809 SEQ ID NO: 91 |
| AAV CBr-e5 | 722 | U.S. Pat. No. 8,734,809 SEQ ID NO: 92 |
| AAV CBr-E6 | 723 | U.S. Pat. No. 8,734,809 SEQ ID NO: 93 |
| AAV CBr-E7 | 724 | U.S. Pat. No. 8,734,809 SEQ ID NO: 94 |
| AAV CBr-E8 | 725 | U.S. Pat. No. 8,734,809 SEQ ID NO: 95 |
| AAV CLv-D1 | 726 | U.S. Pat. No. 8,734,809 SEQ ID NO: 96 |
| AAV CLv-D2 | 727 | U.S. Pat. No. 8,734,809 SEQ ID NO: 97 |
| AAV CLv-D3 | 728 | U.S. Pat. No. 8,734,809 SEQ ID NO: 98 |
| AAV CLv-D4 | 729 | U.S. Pat. No. 8,734,809 SEQ ID NO: 99 |
| AAV CLv-D5 | 730 | U.S. Pat. No. 8,734,809 SEQ ID NO: 100 |
| AAV CLv-D6 | 731 | U.S. Pat. No. 8,734,809 SEQ ID NO: 101 |
| AAV CLv-D7 | 732 | U.S. Pat. No. 8,734,809 SEQ ID NO: 102 |
| AAV CLv-D8 | 733 | U.S. Pat. No. 8,734,809 SEQ ID NO: 103 |
| AAV CLv-E1 | 734 | U.S. Pat. No. 8,734,809 SEQ ID NO: 87 |
| AAV CLv-R1 | 735 | U.S. Pat. No. 8,734,809 SEQ ID NO: 104 |
| AAV CLv-R2 | 736 | U.S. Pat. No. 8,734,809 SEQ ID NO: 105 |
| AAV CLv-R3 | 737 | U.S. Pat. No. 8,734,809 SEQ ID NO: 106 |
| AAV CLv-R4 | 738 | U.S. Pat. No. 8,734,809 SEQ ID NO: 107 |
| AAV CLv-R5 | 739 | U.S. Pat. No. 8,734,809 SEQ ID NO: 108 |
| AAV CLv-R6 | 740 | U.S. Pat. No. 8,734,809 SEQ ID NO: 109 |
| AAV CLv-R7 | 741 | U.S. Pat. No. 8,734,809 SEQ ID NO: 110 |
| AAV CLv-R8 | 742 | U.S. Pat. No. 8,734,809 SEQ ID NO: 111 |
| AAV CLv-R9 | 743 | U.S. Pat. No. 8,734,809 SEQ ID NO: 112 |
| AAV CLg-F1 | 744 | U.S. Pat. No. 8,734,809 SEQ ID NO: 113 |
| AAV CLg-F2 | 745 | U.S. Pat. No. 8,734,809 SEQ ID NO: 114 |
| AAV CLg-F3 | 746 | U.S. Pat. No. 8,734,809 SEQ ID NO: 115 |
| AAV CLg-F4 | 747 | U.S. Pat. No. 8,734,809 SEQ ID NO: 116 |
| AAV CLg-F5 | 748 | U.S. Pat. No. 8,734,809 SEQ ID NO: 117 |
| AAV CLg-F6 | 749 | U.S. Pat. No. 8,734,809 SEQ ID NO: 117 |
| AAV CLg-F7 | 750 | U.S. Pat. No. 8,734,809 SEQ ID NO: 118 |
| AAV CLg-F8 | 751 | U.S. Pat. No. 8,734,809 SEQ ID NO: 117 |
| AAV CSp-1 | 752 | U.S. Pat. No. 8,734,809 SEQ ID NO: 119 |
| AAV CSp-10 | 753 | U.S. Pat. No. 8,734,809 SEQ ID NO: 120 |
| AAV CSp-11 | 754 | U.S. Pat. No. 8,734,809 SEQ ID NO: 121 |
| AAV CSp-2 | 755 | U.S. Pat. No. 8,734,809 SEQ ID NO: 122 |
| AAV CSp-3 | 756 | U.S. Pat. No. 8,734,809 SEQ ID NO: 123 |
| AAV CSp-4 | 757 | U.S. Pat. No. 8,734,809 SEQ ID NO: 124 |
| AAV CSp-6 | 758 | U.S. Pat. No. 8,734,809 SEQ ID NO: 125 |
| AAV CSp-7 | 759 | U.S. Pat. No. 8,734,809 SEQ ID NO: 126 |
| AAV CSp-8 | 760 | U.S. Pat. No. 8,734,809 SEQ ID NO: 127 |
| AAV CSp-9 | 761 | U.S. Pat. No. 8,734,809 SEQ ID NO: 128 |
| AAV CHt-2 | 762 | U.S. Pat. No. 8,734,809 SEQ ID NO: 129 |
| AAV CHt-3 | 763 | U.S. Pat. No. 8,734,809 SEQ ID NO: 130 |
| AAV CKd-1 | 764 | U.S. Pat. No. 8,734,809 SEQ ID NO: 131 |
| AAV CKd-10 | 765 | U.S. Pat. No. 8,734,809 SEQ ID NO: 132 |
| AAV CKd-2 | 766 | U.S. Pat. No. 8,734,809 SEQ ID NO: 133 |
| AAV CKd-3 | 767 | U.S. Pat. No. 8,734,809 SEQ ID NO: 134 |
| AAV CKd-4 | 768 | U.S. Pat. No. 8,734,809 SEQ ID NO: 135 |
| AAV CKd-6 | 769 | U.S. Pat. No. 8,734,809 SEQ ID NO: 136 |
| AAV CKd-7 | 770 | U.S. Pat. No. 8,734,809 SEQ ID NO: 137 |
| AAV CKd-8 | 771 | U.S. Pat. No. 8,734,809 SEQ ID NO: 138 |

TABLE 4-continued

AAV Serotypes

| Serotype | SEQ ID NO | Reference Information |
|---|---|---|
| AAV CLv-1 | 772 | U.S. Pat. No. 8,734,809 SEQ ID NO: 139 |
| AAV CLv-12 | 773 | U.S. Pat. No. 8,734,809 SEQ ID NO: 140 |
| AAV CLv-13 | 774 | U.S. Pat. No. 8,734,809 SEQ ID NO: 141 |
| AAV CLv-2 | 775 | U.S. Pat. No. 8,734,809 SEQ ID NO: 142 |
| AAV CLv-3 | 776 | U.S. Pat. No. 8,734,809 SEQ ID NO: 143 |
| AAV CLv-4 | 777 | U.S. Pat. No. 8,734,809 SEQ ID NO: 144 |
| AAV CLv-6 | 778 | U.S. Pat. No. 8,734,809 SEQ ID NO: 145 |
| AAV CLv-8 | 779 | U.S. Pat. No. 8,734,809 SEQ ID NO: 146 |
| AAV CKd-B1 | 780 | U.S. Pat. No. 8,734,809 SEQ ID NO: 147 |
| AAV CKd-B2 | 781 | U.S. Pat. No. 8,734,809 SEQ ID NO: 148 |
| AAV CKd-B3 | 782 | U.S. Pat. No. 8,734,809 SEQ ID NO: 149 |
| AAV CKd-B4 | 783 | U.S. Pat. No. 8,734,809 SEQ ID NO: 150 |
| AAV CKd-B5 | 784 | U.S. Pat. No. 8,734,809 SEQ ID NO: 151 |
| AAV CKd-B6 | 785 | U.S. Pat. No. 8,734,809 SEQ ID NO: 152 |
| AAV CKd-B7 | 786 | U.S. Pat. No. 8,734,809 SEQ ID NO: 153 |
| AAV CKd-B8 | 787 | U.S. Pat. No. 8,734,809 SEQ ID NO: 154 |
| AAV CKd-H1 | 788 | U.S. Pat. No. 8,734,809 SEQ ID NO: 155 |
| AAV CKd-H2 | 789 | U.S. Pat. No. 8,734,809 SEQ ID NO: 156 |
| AAV CKd-H3 | 790 | U.S. Pat. No. 8,734,809 SEQ ID NO: 157 |
| AAV CKd-H4 | 791 | U.S. Pat. No. 8,734,809 SEQ ID NO: 158 |
| AAV CKd-H5 | 792 | U.S. Pat. No. 8,734,809 SEQ ID NO: 159 |
| AAV CKd-H6 | 793 | U.S. Pat. No. 8,734,809 SEQ ID NO: 151 |
| AAV CHt-1 | 794 | U.S. Pat. No. 8,734,809 SEQ ID NO: 160 |
| AAV CHt-P2 | 795 | WO2016065001 SEQ ID NO: 1 |
| AAV CHt-P5 | 796 | WO2016065001 SEQ ID NO: 2 |
| AAV CHt-P9 | 797 | WO2016065001 SEQ ID NO: 3 |
| AAV CBr-7.1 | 798 | WO2016065001 SEQ ID NO: 4 |
| AAV CBr-7.2 | 799 | WO2016065001 SEQ ID NO: 5 |
| AAV CBr-7.3 | 800 | WO2016065001 SEQ ID NO: 6 |
| AAV CBr-7.4 | 801 | WO2016065001 SEQ ID NO: 7 |
| AAV CBr-7.5 | 802 | WO2016065001 SEQ ID NO: 8 |
| AAV CBr-7.7 | 803 | WO2016065001 SEQ ID NO: 9 |
| AAV CBr-7.8 | 804 | WO2016065001 SEQ ID NO: 10 |
| AAV CBr-7.10 | 805 | WO2016065001 SEQ ID NO: 11 |
| AAV CKd-N3 | 806 | WO2016065001 SEQ ID NO: 12 |
| AAV CKd-N4 | 807 | WO2016065001 SEQ ID NO: 13 |
| AAV CKd-N9 | 808 | WO2016065001 SEQ ID NO: 14 |
| AAV CLv-L4 | 809 | WO2016065001 SEQ ID NO: 15 |
| AAV CLv-L5 | 810 | WO2016065001 SEQ ID NO: 16 |
| AAV CLv-L6 | 811 | WO2016065001 SEQ ID NO: 17 |
| AAV CLv-K1 | 812 | WO2016065001 SEQ ID NO: 18 |
| AAV CLv-K3 | 813 | WO2016065001 SEQ ID NO: 19 |
| AAV CLv-K6 | 814 | WO2016065001 SEQ ID NO: 20 |
| AAV CLv-M1 | 815 | WO2016065001 SEQ ID NO: 21 |
| AAV CLv-M11 | 816 | WO2016065001 SEQ ID NO: 22 |
| AAV CLv-M2 | 817 | WO2016065001 SEQ ID NO: 23 |
| AAV CLv-M5 | 818 | WO2016065001 SEQ ID NO: 24 |
| AAV CLv-M6 | 819 | WO2016065001 SEQ ID NO: 25 |
| AAV CLv-M7 | 820 | WO2016065001 SEQ ID NO: 26 |
| AAV CLv-M8 | 821 | WO2016065001 SEQ ID NO: 27 |
| AAV CLv-M9 | 822 | WO2016065001 SEQ ID NO: 28 |
| AAV CHt-P1 | 823 | WO2016065001 SEQ ID NO: 29 |
| AAV CHt-P6 | 824 | WO2016065001 SEQ ID NO: 30 |
| AAV CHt-P8 | 825 | WO2016065001 SEQ ID NO: 31 |
| AAV CHt-6.1 | 826 | WO2016065001 SEQ ID NO: 32 |
| AAV CHt-6.10 | 827 | WO2016065001 SEQ ID NO: 33 |
| AAV CHt-6.5 | 828 | WO2016065001 SEQ ID NO: 34 |
| AAV CHt-6.6 | 829 | WO2016065001 SEQ ID NO: 35 |
| AAV CHt-6.7 | 830 | WO2016065001 SEQ ID NO: 36 |
| AAV CHt-6.8 | 831 | WO2016065001 SEQ ID NO: 37 |
| AAV CSp-8.10 | 832 | WO2016065001 SEQ ID NO: 38 |
| AAV CSp-8.2 | 833 | WO2016065001 SEQ ID NO: 39 |
| AAV CSp-8.4 | 834 | WO2016065001 SEQ ID NO: 40 |
| AAV CSp-8.5 | 835 | WO2016065001 SEQ ID NO: 41 |
| AAV CSp-8.6 | 836 | WO2016065001 SEQ ID NO: 42 |
| AAV CSp-8.7 | 837 | WO2016065001 SEQ ID NO: 43 |
| AAV CSp-8.8 | 838 | WO2016065001 SEQ ID NO: 44 |
| AAV CSp-8.9 | 839 | WO2016065001 SEQ ID NO: 45 |
| AAV CBr-B7.3 | 840 | WO2016065001 SEQ ID NO: 46 |
| AAV CBr-B7.4 | 841 | WO2016065001 SEQ ID NO: 47 |
| AAV3B | 842 | WO2016065001 SEQ ID NO: 48 |
| AAV4 | 843 | WO2016065001 SEQ ID NO: 49 |
| AAV5 | 844 | WO2016065001 SEQ ID NO: 50 |
| AAV CHt-P2 | 845 | WO2016065001 SEQ ID NO: 51 |
| AAV CHt-P5 | 846 | WO2016065001 SEQ ID NO: 52 |
| AAV CHt-P9 | 847 | WO2016065001 SEQ ID NO: 53 |
| AAV CBr-7.1 | 848 | WO2016065001 SEQ ID NO: 54 |
| AAV CBr-7.2 | 849 | WO2016065001 SEQ ID NO: 55 |
| AAV CBr-7.3 | 850 | WO2016065001 SEQ ID NO: 56 |
| AAV CBr-7.4 | 851 | WO2016065001 SEQ ID NO: 57 |
| AAV CBr-7.5 | 852 | WO2016065001 SEQ ID NO: 58 |
| AAV CBr-7.7 | 853 | WO2016065001 SEQ ID NO: 59 |
| AAV CBr-7.8 | 854 | WO2016065001 SEQ ID NO: 60 |
| AAV CBr-7.10 | 855 | WO2016065001 SEQ ID NO: 61 |
| AAV CKd-N3 | 856 | WO2016065001 SEQ ID NO: 62 |
| AAV CKd-N4 | 857 | WO2016065001 SEQ ID NO: 63 |
| AAV CKd-N9 | 858 | WO2016065001 SEQ ID NO: 64 |
| AAV CLv-L4 | 859 | WO2016065001 SEQ ID NO: 65 |
| AAV CLv-L5 | 860 | WO2016065001 SEQ ID NO: 66 |
| AAV CLv-L6 | 861 | WO2016065001 SEQ ID NO: 67 |
| AAV CLv-K1 | 862 | WO2016065001 SEQ ID NO: 68 |
| AAV CLv-K3 | 863 | WO2016065001 SEQ ID NO: 69 |
| AAV CLv-K6 | 864 | WO2016065001 SEQ ID NO: 70 |
| AAV CLv-M1 | 865 | WO2016065001 SEQ ID NO: 71 |
| AAV CLv-M11 | 866 | WO2016065001 SEQ ID NO: 72 |
| AAV CLv-M2 | 867 | WO2016065001 SEQ ID NO: 73 |
| AAV CLv-M5 | 868 | WO2016065001 SEQ ID NO: 74 |
| AAV CLv-M6 | 869 | WO2016065001 SEQ ID NO: 75 |
| AAV CLv-M7 | 870 | WO2016065001 SEQ ID NO: 76 |
| AAV CLv-M8 | 871 | WO2016065001 SEQ ID NO: 77 |
| AAV CLv-M9 | 872 | WO2016065001 SEQ ID NO: 78 |
| AAV CHt-P1 | 873 | WO2016065001 SEQ ID NO: 79 |
| AAV CHt-P6 | 874 | WO2016065001 SEQ ID NO: 80 |
| AAV CHt-P8 | 875 | WO2016065001 SEQ ID NO: 81 |
| AAV CHt-6.1 | 876 | WO2016065001 SEQ ID NO: 82 |
| AAV CHt-6.10 | 877 | WO2016065001 SEQ ID NO: 83 |
| AAV CHt-6.5 | 878 | WO2016065001 SEQ ID NO: 84 |
| AAV CHt-6.6 | 879 | WO2016065001 SEQ ID NO: 85 |
| AAV CHt-6.7 | 880 | WO2016065001 SEQ ID NO: 86 |
| AAV CHt-6.8 | 881 | WO2016065001 SEQ ID NO: 87 |
| AAV CSp-8.10 | 882 | WO2016065001 SEQ ID NO: 88 |
| AAV CSp-8.2 | 883 | WO2016065001 SEQ ID NO: 89 |
| AAV CSp-8.4 | 884 | WO2016065001 SEQ ID NO: 90 |
| AAV CSp-8.5 | 885 | WO2016065001 SEQ ID NO: 91 |
| AAV CSp-8.6 | 886 | WO2016065001 SEQ ID NO: 92 |
| AAV CSp-8.7 | 887 | WO2016065001 SEQ ID NO: 93 |
| AAV CSp-8.8 | 888 | WO2016065001 SEQ ID NO: 94 |
| AAV CSp-8.9 | 889 | WO2016065001 SEQ ID NO: 95 |
| AAV CBr-B7.3 | 890 | WO2016065001 SEQ ID NO: 96 |
| AAV CBr-B7.4 | 891 | WO2016065001 SEQ ID NO: 97 |
| AAV3B | 892 | WO2016065001 SEQ ID NO: 98 |
| AAV4 | 893 | WO2016065001 SEQ ID NO: 99 |
| AAV5 | 894 | WO2016065001 SEQ ID NO: 100 |
| AAVPHP.B or G2B-26 | 895 | WO2015038958 SEQ ID NO: 8 and 13; GenBankALU85156.1 |
| AAVPHP.B | 896 | WO2015038958 SEQ ID NO: 9 |
| AAVG2B-13 | 897 | WO2015038958 SEQ ID NO: 12 |
| AAVTH1.1-32 | 898 | WO2015038958 SEQ ID NO: 14 |
| AAVTH1.1-35 | 899 | WO2015038958 SEQ ID NO: 15 |

Each of the patents, applications and/or publications listed in Table 4 are hereby incorporated by reference in their entirety.

In one embodiment, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 153 and 154 respectively herein), PHP.B (SEQ ID NO: 8 and 9 of WO2015038958, herein SEQ ID NO: 895 and 896), G2B-13 (SEQ ID NO: 12 of WO2015038958, herein SEQ ID NO: 897), G2B-26 (SEQ ID NO: 13 of WO2015038958, herein SEQ ID NO: 895 and 896), TH1.1-32 (SEQ ID NO: 14 of WO2015038958, herein SEQ ID NO: 898), TH1.1-35 (SEQ ID NO: 15 of WO2015038958, herein SEQ ID NO: 899) or variants thereof. Further, any of the targeting peptides or amino acid inserts described in WO2015038958, may be inserted into any parent AAV serotype, such as, but not limited to, AAV9 (SEQ ID NO: 153 for the DNA sequence and SEQ ID NO: 154 for the amino acid sequence). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 900), KFPVALT (SEQ ID NO: 3 of WO2015038958; herein SEQ ID NO: 901), LAVPFK (SEQ ID NO: 31 of WO2015038958; herein SEQ ID NO: 902), AVPFK (SEQ ID NO: 32 of WO2015038958; herein SEQ ID NO: 903), VPFK (SEQ ID NO: 33 of WO2015038958; herein SEQ ID NO: 904), TLAVPF (SEQ ID NO: 34 of WO2015038958; herein SEQ ID NO: 905), TLAVP (SEQ ID NO: 35 of WO2015038958; herein SEQ ID NO: 906), TLAV (SEQ ID NO: 36 of WO2015038958; herein SEQ ID NO: 907), SVSKPFL (SEQ ID NO: 28 of WO2015038958; herein SEQ ID NO: 908), FTLTTPK (SEQ ID NO: 29 of WO2015038958; herein SEQ ID NO: 909), MNATKNV (SEQ ID NO: 30 of WO2015038958; herein SEQ ID NO: 910), QSSQTPR (SEQ ID NO: 54 of WO2015038958; herein SEQ ID NO: 911), ILGTGTS (SEQ ID NO: 55 of WO2015038958; herein SEQ ID NO: 912), TRTNPEA (SEQ ID NO: 56 of WO2015038958; herein SEQ ID NO: 913), NGGTSSS (SEQ ID NO: 58 of WO2015038958; herein SEQ ID NO: 914), or YTLSQGW (SEQ ID NO: 60 of WO2015038958; herein SEQ ID NO: 915). Non-limiting examples of nucleotide sequences that may encode the amino acid inserts include the following, AAGTTTCCTGTGGCGTTGACT (for SEQ ID NO: 3 of WO2015038958; herein SEQ ID NO: 916), ACTTTGGCGGTGCCTTTTAAG (SEQ ID NO: 24 and 49 of WO2015038958; herein SEQ ID NO: 917), AGTGTGAGTAAGCCTTTTTG (SEQ ID NO: 25 of WO2015038958; herein SEQ ID NO: 918), TTTACGTTGACGACGCCTAAG (SEQ ID NO: 26 of WO2015038958; herein SEQ ID NO: 919), ATGAATGCTACGAAGAATGTG (SEQ ID NO: 27 of WO2015038958; herein SEQ ID NO: 920), CAGTCGTCGCAGACGCCTAGG (SEQ ID NO: 48 of WO2015038958; herein SEQ ID NO: 921), ATTCTGGGGACTGGTACTTCG (SEQ ID NO: 50 and 52 of WO2015038958; herein SEQ ID NO: 922), ACGCGGACTAATCCTGAGGCT (SEQ ID NO: 51 of WO2015038958; herein SEQ ID NO: 923), AATGGGGGACTAGTAGTTCT (SEQ ID NO: 53 of WO2015038958; herein SEQ ID NO: 924), or TATACTTTGTCGCAGGGTTGG (SEQ ID NO: 59 of WO2015038958; herein SEQ ID NO: 925).

In one embodiment, the AAV serotype may be engineered to comprise at least one AAV capsid CD8+ T-cell epitope. Hui et al. (Molecular Therapy—Methods & Clinical Development (2015) 2, 15029 doi:10.1038/mtm.2015.29; the contents of which are herein incorporated by reference in its entirety) identified AAV capsid-specific CD8+ T-cell epitopes for AAV1 and AAV2 (see e.g., Table 2 in the publication). As a non-limiting example, the capsid-specific CD8+ T-cell epitope may be for an AAV2 serotype. As a non-limiting example, the capsid-specific CD8+ T-cell epitope may be for an AAV1 serotype.

In one embodiment, the AAV serotype may be engineered to comprise at least one AAV capsid CD8+ T-cell epitope for AAV2 such as, but not limited to, SADNNNSEY (SEQ ID NO: 926), LIDQYLYYL (SEQ ID NO: 927), VPQYGYLTL (SEQ ID NO: 928), TTSTRTWAL (SEQ ID NO: 929), YHLNGRDSL (SEQ ID NO: 930), SQAVGRSSF (SEQ ID NO: 931), VPANPSTTF (SEQ ID NO: 932), FPQSGVLIF (SEQ ID NO: 933), YFDFNRFHCHFSPRD (SEQ ID NO: 934), VGNSSGNWHCDSTWM (SEQ ID NO: 935), QFSQAGASDIRDQSR (SEQ ID NO: 936), GASDIRQSRNWLP (SEQ ID NO: 937) and GNRQAATADVNTQGV (SEQ ID NO: 938).

In one embodiment, the AAV serotype may be engineered to comprise at least one AAV capsid CD8+ T-cell epitope for AAV1 such as, but not limited to, LDRLMNPLI (SEQ ID NO: 939), TTSTRTWAL (SEQ ID NO: 929), and QPAKKRLNF (SEQ ID NO: 940)).

In one embodiment, peptides for inclusion in an AAV serotype may be identified using the methods described by Hui et al. (Molecular Therapy—Methods & Clinical Development (2015) 2, 15029 doi:10.1038/mtm.2015.29; the contents of which are herein incorporated by reference in its entirety). As a non-limiting example, the procedure includes isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the HLA restriction of 15-mers identified by IFN-gamma ELISpot, identification of candidate reactive 9-mer epitopes for a given HLA allele, synthesis candidate 9-mers, second IFN-gamma ELISpot screening of splenocytes from subjects carrying the HLA alleles to which identified AAV epitopes are predicted to bind, determine the AAV capsid-reactive CD8+ T cell epitopes and determine the frequency of subjects reacting to a given AAV epitope.

In one embodiment, the AAV may be a serotype generated by Cre-recombination-based AAV targeted evolution (CREATE) as described by Deverman et al., (Nature Biotechnology 34(2):204-209 (2016)), the contents of which are herein incorporated by reference in their entirety. In one embodiment, AAV serotypes generated in this manner have improved CNS transduction and/or neuronal and astrocytic tropism, as compared to other AAV serotypes. As non-limiting examples, the AAV serotype may be PHP.B, PHP.B2, PHP.B3, PHP.A, G2A12, G2A15. In one embodiment, these AAV serotypes may be AAV9 (SEQ ID NO: 153 and 154) derivatives with a 7-amino acid insert between amino acids 588-589. Non-limiting examples of these 7-amino acid inserts include TLAVPFK (SEQ ID NO: 900), SVSKPFL (SEQ ID NO: 908), FTLTTPK (SEQ ID NO: 909), YTLSQGW (SEQ ID NO: 915), QAVRTSL (SEQ ID NO: 941) and/or LAKERLS (SEQ ID NO: 942).

In one embodiment, the AAV serotype may be as described in Jackson et al (Frontiers in Molecular Neuroscience 9:154 (2016)), the contents of which are herein incorporated by reference in their entirety. In some embodiments, the AAV serotype is PHP.B or AAV9. In some embodiments, the AAV serotype is paired with a synapsin promoter to enhance neuronal transduction, as compared to when more ubiquitous promoters are used (i.e., CBA or CMV).

In one embodiment, peptides for inclusion in an AAV serotype may be identified by isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the given allele restriction of 15-mers identified by IFN-gamma ELISpot, identification of candidate reactive 9-mer epitopes for a given allele, synthesis candidate 9-mers, second IFN-gamma ELISpot screening of splenocytes from subjects carrying the specific alleles to which identified AAV epitopes are predicted to bind, determine the AAV capsid-reactive CD8+ T cell epitopes and determine the frequency of subjects reacting to a given AAV epitope.

AAV vectors comprising the nucleic acid sequence for the siRNA molecules may be prepared or derived from various serotypes of AAVs, including, but not limited to, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A, and/or AAV-PHP.B. In some cases, different serotypes of AAVs may be mixed together or with other types of viruses to produce chimeric AAV vectors. As a non-limiting example, the AAV vector is derived from the AAV9 serotype.

Viral Genome Component: Inverted Terminal Repeats (ITRs)

The AAV particles of the present invention comprise a viral genome with at least one ITR region and a payload region. In one embodiment the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the invention may be comprised of naturally occurring polynucleotide sequences or recombinantly derived polynucleotide sequences.

The ITRs may be derived from the same serotype as the capsid, selected from any of the serotypes listed in Table 6, or a derivative thereof. The ITR may be of a different serotype than the capsid. In one embodiment the AAV particle has more than one ITR. In a non-limiting example, the AAV particle has a viral genome comprising two ITRs. In one embodiment the ITRs are of the same serotype as one another. In another embodiment the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment the ITRs are 140-142 nucleotides in length. Non limiting examples of ITR length are 102, 140, 141, 142, 145 nucleotides in length, and those having at least 95% identity thereto.

In one embodiment, the encoded siRNA molecule may be located near the 5' end of the flip ITR in an expression vector. In another embodiment, the encoded siRNA molecule may be located near the 3' end of the flip ITR in an expression vector. In yet another embodiment, the encoded siRNA molecule may be located near the 5' end of the flop ITR in an expression vector. In yet another embodiment, the encoded siRNA molecule may be located near the 3' end of the flop ITR in an expression vector. In one embodiment, the encoded siRNA molecule may be located between the 5' end of the flip ITR and the 3' end of the flop ITR in an expression vector. In one embodiment, the encoded siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

Viral Genome Component: Promoters

A person skilled in the art may recognize that a target cell may require a specific promoter including but not limited to a promoter that is species specific, inducible, tissue-specific, or cell cycle-specific (Parr et al., Nat. Med.3:1145-9 (1997); the contents of which are herein incorporated by reference in its entirety).

In one embodiment, the promoter is a promoter deemed to be efficient to drive the expression of the modulatory polynucleotide.

In one embodiment, the promoter is a promoter having a tropism for the cell being targeted.

In one embodiment, the promoter is a weak promoter which provides expression of a payload e.g., a modulatory polynucleotide, e.g., siRNA or dsRNA, for a period of time in targeted tissues such as, but not limited to, nervous system tissues. Expression may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues.

In one embodiment, the promoter may be a promoter which is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. As a non-limiting example, the promoter is a combination of a 382 nucleotide CMV-enhancer sequence and a 260 nucleotide CBA-promoter sequence.

In one embodiment, the vector genome comprises at least one element to enhance the target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miR-NAs, post-transcriptional regulatory elements (PREs), polyadenylation (PolyA) signal sequences and upstream enhancers (USEs), CMV enhancers and introns.

In one embodiment, the vector genome comprises at least one element to enhance the target specificity and expression (See e.g., Powell et al. Viral Expression Cassette Elements to Enhance Transgene Target Specificity and Expression in Gene Therapy, 2015; the contents of which are herein incorporated by reference in its entirety) such as promoters.

Promoters for which promote expression in most tissues include, but are not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting example of tissue-specific expression elements for neurons include neuron-specific enolase (NSE), platelet-derived growth factor (PDGF), platelet-derived growth factor B-chain (PDGF-β), the synapsin (Syn), the methyl-CpG binding protein 2 (MeCP2), CaMKII, mGluR2, NFL, NFH, nf32, PPE, Enk and EAAT2 promoters. A non-limiting example of tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In one embodiment, the vector genome comprises a ubiquitous promoter. Non-limiting examples of ubiquitous promoters include H1, U6, CMV, CBA (including derivatives CAG, CBh, etc.), EF-1α, PGK, UBC, GUSB (hGBp), and UCOE (promoter of HNRPA2B1-CBX3). Yu et al. (Molecular Pain 2011, 7:63; the contents of which are herein incorporated by reference in its entirety) evaluated the expression of eGFP under the CAG, EFIa, PGK and UBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in its entirety) the expression of eGFP in AAV8 with CMV and UBC promoters and AAV2 with the CMV promoter after injection in the motor cortex. Intranasal administration of a plasmid containing a UBC or EFIa promoter showed a sustained airway expression greater than the expression with the CMV promoter (See e.g., Gill et al., Gene Therapy 2001, Vol. 8, 1539-1546; the contents of which are herein incorporated by reference in its entirety). Husain et al. (Gene Therapy 2009; the contents of which are herein incorporated by reference in its entirety) evaluated a HβH construct with a hGUSB promoter, a HSV-1LAT promoter and a NSE promoter and found that the HβH construct showed weaker expression than NSE in mice brain. Passini and Wolfe (J. Virol. 2001, 12382-12392, the contents of which are herein incorporated by reference in its entirety) evaluated the long term effects of the Hf3H vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. 2007 and Raymond et al. 2004; the contents of each of which are herein incorporated by reference in their entireties).

In one embodiment, the vector genome comprises an UBC promoter. The UBC promoter may have a size of 300-350 nucleotides. As a non-limiting example, the UBC promoter is 332 nucleotides.

In one embodiment, the vector genome comprises a GUSB promoter. The GUSB promoter may have a size of 350-400 nucleotides. As a non-limiting example, the GUSB promoter is 378 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a NFL promoter. The NFL promoter may have a size of 600-700 nucleotides. As a non-limiting example, the NFL promoter is 650 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a NFH promoter. The NFH promoter may have a size of 900-950 nucleotides. As a non-limiting example, the NFH promoter is 920 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a scn8a promoter. The scn8a promoter may have a size of 450-500 nucleotides. As a non-limiting example, the scn8a promoter is 470 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a FXN promoter.

In one embodiment, the vector genome comprises a PGK promoter.

In one embodiment, the vector genome comprises a CBA promoter.

In one embodiment, the vector genome comprises a CMV promoter.

In one embodiment, the vector genome comprises a H1 promoter.

In one embodiment, the vector genome comprises a U6 promoter.

In one embodiment, the vector genome comprises a liver or a skeletal muscle promoter. Non-limiting examples of liver promoters include hAAT and TBG. Non-limiting examples of skeletal muscle promoters include Desmin, MCK and C5-12.

In one embodiment, the AAV vector comprises an enhancer element, a promoter and/or a 5'UTR intron. The enhancer may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter; (9) GFAP promoter, (10) H1 promoter; and (11) U6 promoter.

In one embodiment, the AAV vector has an engineered promoter.

Viral Genome Component: Introns

In one embodiment, the vector genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The promoter may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV vector may comprise an SV40 intron or fragment or variant thereof. As a non-limiting example, the promoter may be CMV. As another non-limiting example, the promoter may be CBA. As yet another non-limiting example, the promoter may be H1.

In one embodiment, the AAV vector may comprise a beta-globin intron or a frament or variant thereof. As a non-limiting example, the promoter may be CMV. As another non-limiting example, the promoter may be CBA. As yet another non-limiting example, the promoter may be H1.

In one embodiment, the encoded siRNA molecule may be located downstream of an intron in an expression vector such as, but not limited to, SV40 intron or beta globin intron or others known in the art. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter with an intron and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the intron and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the intron and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% of the sequence downstream from the intron and/or upstream of the polyadenylation sequence in an expression vector.

Viral Genome Component: Polyadenylation Sequence

In one embodiment, the viral genome of the AAV particles of the present invention comprise at least one polyadenylation sequence. The viral genome of the AAV particle may comprise a polyadenylation sequence between the 3' end of the payload coding sequence and the 5' end of the 3' ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

In one embodiment, the encoded siRNA molecule may be located upstream of the polyadenylation sequence in an expression vector. Further, the encoded siRNA molecule may be located downstream of a promoter such as, but not limited to, CMV, U6, H1, CBA or a CBA promoter with a SV40 or a human betaglobin intron in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

Expression Vector

In one embodiment, an expression vector (e.g., AAV vector) may comprise at least one of the modulatory polynucleotides encoding at least one of the siRNA sequences or duplexes described herein.

In one embodiment, an expression vector may comprise, from ITR to ITR recited 5' to 3', an ITR, a promoter, an intron, a modulatory polynucleotide, a polyA sequence and an ITR.

Genome Size

In one embodiment, the vector genome which comprises a nucleic acid sequence encoding the modulatory polynucleotides described herein may be single stranded or double stranded vector genome. The size of the vector genome may be small, medium, large or the maximum size. Additionally, the vector genome may comprise a promoter and a polyA tail.

In one embodiment, the vector genome which comprises a nucleic acid sequence encoding the modulatory polynucleotides described herein may be a small single stranded vector genome. A small single stranded vector genome may be 2.7 to 3.5 kb in size such as about 2.7, 2.8, 2.9, 3.0, 3.1, 3.2, 3.3, 3.4, and 3.5 kb in size. As a non-limiting example, the small single stranded vector genome may be 3.2 kb in size. Additionally, the vector genome may comprise a promoter and a polyA tail.

In one embodiment, the vector genome which comprises a nucleic acid sequence encoding the modulatory polynucleotides described herein may be a small double stranded vector genome. A small double stranded vector genome may be 1.3 to 1.7 kb in size such as about 1.3, 1.4, 1.5, 1.6, and 1.7 kb in size. As a non-limiting example, the small double stranded vector genome may be 1.6 kb in size. Additionally, the vector genome may comprise a promoter and a polyA tail.

In one embodiment, the vector genome which comprises a nucleic acid sequence encoding the modulatory polynucleotides described herein e.g., siRNA or dsRNA, may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. As a non-limiting example, the medium single stranded vector genome may be 4.0 kb in size. Additionally, the vector genome may comprise a promoter and a polyA tail.

In one embodiment, the vector genome which comprises a nucleic acid sequence encoding the modulatory polynucleotides described herein may be a medium double stranded vector genome. A medium double stranded vector genome may be 1.8 to 2.1 kb in size such as about 1.8, 1.9, 2.0, and 2.1 kb in size. As a non-limiting example, the medium double stranded vector genome may be 2.0 kb in size. Additionally, the vector genome may comprise a promoter and a polyA tail.

In one embodiment, the vector genome which comprises a nucleic acid sequence encoding the modulatory polynucleotides described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size. Additionally, the vector genome may comprise a promoter and a polyA tail.

In one embodiment, the vector genome which comprises a nucleic acid sequence encoding the modulatory polynucleotides described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size. Additionally, the vector genome may comprise a promoter and a polyA tail.

Viral Production

The present disclosure provides a method for the generation of parvoviral particles, e.g. AAV particles, by viral genome replication in a viral replication cell comprising contacting the viral replication cell with an AAV polynucleotide or AAV genome.

The present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In one embodiment, the present invention provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

Cells

The present disclosure provides a cell comprising an AAV polynucleotide and/or AAV genome.

Viral production disclosed herein describes processes and methods for producing AAV particles that contact a target cell to deliver a payload construct, e.g. a recombinant viral construct, which comprises a nucleotide encoding a payload molecule.

In one embodiment, the AAV particles may be produced in a viral replication cell that comprises an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present invention. Cell lines may be used from Spodoptera frugiperda, including, but not limited to the Sf9 or Sf21 cell lines, Drosophila cell lines, or mosquito cell lines, such as Aedes albopictus derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., J. Vir.63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir.219:37-44 (1996); Zhao et al., Vir.272: 382-93 (2000); and Samulski et al., U.S. Pat. No. 6,204,059, the contents of each of which is herein incorporated by reference in its entirety.

The viral replication cell may be selected from any biological organism, including prokaryotic (e.g., bacterial) cells, and eukaryotic cells, including, insect cells, yeast cells and mammalian cells. Viral replication cells may comprise mammalian cells such as A549, WEH1, 3T3, 10T1/2, BHK, MDCK, COS 1, COS 7, BSC 1, BSC 40, BMT 10, VERO. W138, HeLa, HEK293, Saos, C2C12, L cells, HT1080, HepG2 and primary fibroblast, hepatocyte and myoblast cells derived from mammals. Viral replication cells comprise cells derived from mammalian species including, but not limited to, human, monkey, mouse, rat, rabbit, and hamster or cell type, including but not limited to fibroblast, hepatocyte, tumor cell, cell line transformed cell, etc.

Small Scale Production of AAV Particles

Viral production disclosed herein describes processes and methods for producing AAV particles that contact a target cell to deliver a payload, e.g. a recombinant viral construct, which comprises a nucleotide encoding a payload.

In one embodiment, the AAV particles may be produced in a viral replication cell that comprises a mammalian cell.

Viral replication cells commonly used for production of recombinant AAV particles include, but are not limited to 293 cells, COS cells, HeLa cells, KB cells, and other mammalian cell lines as described in U.S. Pat. Nos. 6,156, 303, 5,387,484, 5,741,683, 5,691,176, and 5,688,676; U.S. patent application 2002/0081721, and International Patent Applications WO 00/47757, WO 00/24916, and WO 96/17947, the contents of each of which are herein incorporated by reference in their entireties.

In one embodiment, AAV particles are produced in mammalian-cells wherein all three VP proteins are expressed at a stoichiometry approaching 1:1:10 (VP1:VP2:VP3). The regulatory mechanisms that allow this controlled level of expression include the production of two mRNAs, one for VP1, and the other for VP2 and VP3, produced by differential splicing.

In another embodiment, AAV particles are produced in mammalian cells using a triple transfection method wherein a payload construct, parvoviral Rep and parvoviral Cap and a helper construct are comprised within three different constructs. The triple transfection method of the three components of AAV particle production may be utilized to produce small lots of virus for assays including transduction efficiency, target tissue (tropism) evaluation, and stability.

Baculovirus

Particle production disclosed herein describes processes and methods for producing AAV particles that contact a target cell to deliver a payload construct which comprises a nucleotide encoding a payload.

Briefly, the viral construct vector and the AAV payload construct vector are each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the AAV payload construct expression vector. The two baculoviruses may be used to infect a single viral replication cell population for production of AAV particles.

Baculovirus expression vectors for producing viral particles in insect cells, including but not limited to Spodoptera frugiperda (Sf9) cells, provide high titers of viral particle product. Recombinant baculovirus encoding the viral construct expression vector and AAV payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al., J Virol. 2006 February; 80 (4):1874-85, the contents of which are herein incorporated by reference in their entirety.

Production of AAV particles with baculovirus in an insect cell system may address known baculovirus genetic and physical instability. In one embodiment, the production system addresses baculovirus instability over multiple passages by utilizing a titerless infected-cells preservation and scale-up system. Small scale seed cultures of viral producing cells are transfected with viral expression constructs encoding the structural, non-structural, components of the viral particle. Baculovirus-infected viral producing cells are harvested into aliquots that may be cryopreserved in liquid nitrogen; the aliquots retain viability and infectivity for infection of large scale viral producing cell culture Wasilko D J et al., Protein Expr Purif. 2009 June; 65(2):122-32, the contents of which are herein incorporated by reference in their entirety.

A genetically stable baculovirus may be used to produce source of the one or more of the components for producing AAV particles in invertebrate cells. In one embodiment, defective baculovirus expression vectors may be maintained episomally in insect cells. In such an embodiment the bacmid vector is engineered with replication control elements, including but not limited to promoters, enhancers, and/or cell-cycle regulated replication elements.

In one embodiment, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In one embodiment, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

Large-Scale Production

In some embodiments, AAV particle production may be modified to increase the scale of production. Large scale viral production methods according to the present disclosure may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Methods of increasing viral particle production scale typically comprise increasing the number of viral replication cells. In some embodiments, viral replication cells comprise adherent cells. To increase the scale of viral particle production by adherent viral replication cells, larger cell culture surfaces are required. In some cases, large-scale production methods comprise the use of roller bottles to increase cell culture surfaces. Other cell culture substrates with increased surface areas are known in the art. Examples of additional adherent cell culture products with increased surface areas include, but are not limited to CellSTACK®, CellCube® (Corning Corp., Corning, N.Y.) and Nunc™ Cell Factory™ (Thermo Scientific, Waltham, Mass.) In some cases, large-scale adherent cell surfaces may comprise from about 1,000 cm2 to about 100,000 cm2. In some cases, large-scale adherent cell cultures may comprise from about 107 to about 109 cells, from about 108 to about 1010 cells, from about 109 to about 1012 cells or at least 1012 cells. In some cases, large-scale adherent cultures may produce from about 109 to about $10^{12}$, from about 1010 to about $10^{13}$, from about 1011 to about 1014, from about 1012 to about 1015 or at least 1015 viral particles.

In some embodiments, large-scale viral production methods of the present disclosure may comprise the use of suspension cell cultures. Suspension cell culture allows for significantly increased numbers of cells. Typically, the number of adherent cells that can be grown on about 10-50 cm2 of surface area can be grown in about 1 cm3 volume in suspension.

Transfection of replication cells in large-scale culture formats may be carried out according to any methods known in the art. For large-scale adherent cell cultures, transfection methods may include, but are not limited to the use of inorganic compounds (e.g. calcium phosphate), organic compounds [e.g. polyethyleneimine (PEI)] or the use of non-chemical methods (e.g. electroporation.) With cells grown in suspension, transfection methods may include, but are not limited to the use of calcium phosphate and the use of PEI. In some cases, transfection of large scale suspension cultures may be carried out according to the section entitled "Transfection Procedure" described in Feng, L. et al., 2008. Biotechnol Appl. Biochem. 50:121-32, the contents of which are herein incorporated by reference in their entirety. According to such embodiments, PEI-DNA complexes may be formed for introduction of plasmids to be transfected. In some cases, cells being transfected with PEI-DNA complexes may be 'shocked' prior to transfection. This comprises lowering cell culture temperatures to 4° C. for a period of about 1 hour. In some cases, cell cultures may be shocked for a period of from about 10 minutes to about 5 hours. In some cases, cell cultures may be shocked at a temperature of from about 0° C. to about 20° C.

In some cases, transfections may include one or more vectors for expression of an RNA effector molecule to reduce expression of nucleic acids from one or more AAV payload construct. Such methods may enhance the production of viral particles by reducing cellular resources wasted on expressing payload constructs. In some cases, such methods may be carried according to those taught in US Publication No. US2014/0099666, the contents of which are herein incorporated by reference in their entirety.

Bioreactors

In some embodiments, cell culture bioreactors may be used for large scale viral production. In some cases, bioreactors comprise stirred tank reactors. Such reactors generally comprise a vessel, typically cylindrical in shape, with a stirrer (e.g. impeller.) In some embodiments, such bioreactor vessels may be placed within a water jacket to control vessel temperature and/or to minimize effects from ambient temperature changes. Bioreactor vessel volume may range in size from about 500 ml to about 2 L, from about 1 L to about 5 L, from about 2.5 L to about 20 L, from about 10 L to about 50 L, from about 25 L to about 100 L, from about 75 L to about 500 L, from about 250 L to about 2,000 L, from about 1,000 L to about 10,000 L, from about 5,000 L to about 50,000 L or at least 50,000 L. Vessel bottoms may be rounded or flat. In some cases, animal cell cultures may be maintained in bioreactors with rounded vessel bottoms.

In some cases, bioreactor vessels may be warmed through the use of a thermocirculator. Thermocirculators pump heated water around water jackets. In some cases, heated water may be pumped through pipes (e.g. coiled pipes) that are present within bioreactor vessels. In some cases, warm air may be circulated around bioreactors, including, but not limited to air space directly above culture medium. Additionally, pH and CO2 levels may be maintained to optimize cell viability.

In some cases, bioreactors may comprise hollow-fiber reactors. Hollow-fiber bioreactors may support the culture of both anchorage dependent and anchorage independent cells. Further bioreactors may include, but are not limited to packed-bed or fixed-bed bioreactors. Such bioreactors may comprise vessels with glass beads for adherent cell attachment. Further packed-bed reactors may comprise ceramic beads.

In some cases, viral particles are produced through the use of a disposable bioreactor. In some embodiments, such bioreactors may include WaveTM disposable bioreactors.

In some embodiments, AAV particle production in animal cell bioreactor cultures may be carried out according to the methods taught in U.S. Pat. Nos. 5,064,764, 6,194,191, 6,566,118, 8,137,948 or US Patent Application No. US2011/0229971, the contents of each of which are herein incorporated by reference in their entirety.

Cell Lysis

Cells of the invention, including, but not limited to viral production cells, may be subjected to cell lysis according to any methods known in the art. Cell lysis may be carried out to obtain one or more agents (e.g. viral particles) present within any cells of the invention. In some embodiments, cell lysis may be carried out according to any of the methods listed in U.S. Pat. Nos. 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935, 7,968,333, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Cell lysis methods may be chemical or mechanical. Chemical cell lysis typically comprises contacting one or more cells with one or more lysis agent. Mechanical lysis typically comprises subjecting one or more cells to one or more lysis condition and/or one or more lysis force.

In some embodiments, chemical lysis may be used to lyse cells. As used herein, the term "lysis agent" refers to any agent that may aid in the disruption of a cell. In some cases, lysis agents are introduced in solutions, termed lysis solutions or lysis buffers. As used herein, the term "lysis solution" refers to a solution (typically aqueous) comprising one or more lysis agent. In addition to lysis agents, lysis solutions may include one or more buffering agents, solubilizing agents, surfactants, preservatives, cryoprotectants, enzymes, enzyme inhibitors and/or chelators. Lysis buffers are lysis solutions comprising one or more buffering agent. Additional components of lysis solutions may include one or more solubilizing agent. As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity.

Exemplary lysis agents may include any of those described in U.S. Pat. Nos. 8,685,734, 7,901,921, 7,732,129, 7,223,585, 7,125,706, 8,236,495, 8,110,351, 7,419,956, 7,300,797, 6,699,706 and 6,143,567, the contents of each of which are herein incorporated by reference in their entirety. In some cases, lysis agents may be selected from lysis salts, amphoteric agents, cationic agents, ionic detergents and non-ionic detergents. Lysis salts may include, but are not limited to sodium chloride (NaCl) and potassium chloride (KCl.) Further lysis salts may include any of those described in U.S. Pat. Nos. 8,614,101, 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935 and 7,968,333, the contents of each of which are herein incorporated by reference in their entirety. Concentrations of salts may be increased or decreased to obtain an effective concentration for rupture of cell membranes. Amphoteric agents, as referred to herein, are compounds capable of reacting as an acid or a base. Amphoteric agents may include, but are not limited to lysophosphatidylcholine, 3-((3-Cholamidopropyl) dimethylammonium)-1-propanesulfonate (CHAPS), Zwittergent® and the like. Cationic agents may include, but are not limited to cetyltrimethylammonium bromide (C (16) TAB) and Benzalkonium chloride. Lysis agents comprising detergents may include ionic detergents or non-ionic detergents. Detergents may function to break apart or dissolve cell structures including, but not limited to cell membranes, cell walls, lipids, carbohydrates, lipoproteins and glycoproteins. Exemplary ionic detergents include any of those taught in U.S. Pat. Nos. 7,625,570 and 6,593,123 or US Publication No. US2014/0087361, the contents of each of which are herein incorporated by reference in their entirety. Some ionic detergents may include, but are not limited to sodium dodecyl sulfate (SDS), cholate and deoxycholate. In some cases, ionic detergents may be included in lysis solutions as a solubilizing agent. Non-ionic detergents may include, but are not limited to octylglucoside, digitonin, lubrol, C12E8, TWEEN®-20, TWEEN®-80, Triton X-100 and Noniodet P-40. Non-ionic detergents are typically weaker lysis agents, but may be included as solubilizing agents for solubilizing cellular and/or viral proteins. Further lysis agents may include enzymes and urea. In some cases, one or more lysis agents may be combined in a lysis solution in order to enhance one or more of cell lysis and protein solubility. In some cases, enzyme inhibitors may be included in lysis solutions in order to prevent proteolysis that may be triggered by cell membrane disruption.

In some embodiments, mechanical cell lysis is carried out. Mechanical cell lysis methods may include the use of one or more lysis condition and/or one or more lysis force. As used herein, the term "lysis condition" refers to a state or circumstance that promotes cellular disruption. Lysis conditions may comprise certain temperatures, pressures, osmotic purity, salinity and the like. In some cases, lysis conditions comprise increased or decreased temperatures. According to some embodiments, lysis conditions comprise changes in temperature to promote cellular disruption. Cell lysis carried out according to such embodiments may include freeze-thaw lysis. As used herein, the term "freeze-thaw lysis" refers to cellular lysis in which a cell solution is subjected to one or more freeze-thaw cycle. According to freeze-thaw lysis methods, cells in solution are frozen to induce a mechanical disruption of cellular membranes caused by the formation and expansion of ice crystals. Cell solutions used according freeze-thaw lysis methods, may further comprise one or more lysis agents, solubilizing agents, buffering agents, cryoprotectants, surfactants, preservatives, enzymes, enzyme inhibitors and/or chelators. Once cell solutions subjected to freezing are thawed, such components may enhance the recovery of desired cellular products. In some cases, one or more cyroprotectants are included in cell solutions undergoing freeze-thaw lysis. As used herein, the term "cryoprotectant" refers to an agent used to protect one or more substance from damage due to freezing. Cryoprotectants may include any of those taught in US Publication No. US2013/0323302 or U.S. Pat. Nos. 6,503,888, 6,180,613, 7,888,096, 7,091,030, the contents of each of which are herein incorporated by reference in their entirety. In some cases, cryoprotectants may include, but are not limited to dimethyl sulfoxide, 1,2-propanediol, 2,3-butanediol, formamide, glycerol, ethylene glycol, 1,3-propanediol and n-dimethyl formamide, polyvinylpyrrolidone, hydroxyethyl starch, agarose, dextrans, inositol, glucose, hydroxyethylstarch, lactose, sorbitol, methyl glucose, sucrose and urea. In some embodiments, freeze-thaw lysis may be carried out according to any of the methods described in U.S. Pat. No. 7,704,721, the contents of which are herein incorporated by reference in their entirety.

As used herein, the term "lysis force" refers to a physical activity used to disrupt a cell. Lysis forces may include, but are not limited to mechanical forces, sonic forces, gravitational forces, optical forces, electrical forces and the like. Cell lysis carried out by mechanical force is referred to herein as "mechanical lysis." Mechanical forces that may be used according to mechanical lysis may include high shear fluid forces. According to such methods of mechanical lysis, a microfluidizer may be used. Microfluidizers typically comprise an inlet reservoir where cell solutions may be applied. Cell solutions may then be pumped into an interaction chamber via a pump (e.g. high-pressure pump) at high speed and/or pressure to produce shear fluid forces. Resulting lysates may then be collected in one or more output reservoir. Pump speed and/or pressure may be adjusted to modulate cell lysis and enhance recovery of products (e.g. viral particles.) Other mechanical lysis methods may include physical disruption of cells by scraping.

Cell lysis methods may be selected based on the cell culture format of cells to be lysed. For example, with adherent cell cultures, some chemical and mechanical lysis methods may be used. Such mechanical lysis methods may include freeze-thaw lysis or scraping. In another example, chemical lysis of adherent cell cultures may be carried out through incubation with lysis solutions comprising surfactant, such as Triton-X-100. In some cases, cell lysates generated from adherent cell cultures may be treated with one more nuclease to lower the viscosity of the lysates caused by liberated DNA.

In one embodiment, a method for harvesting AAV particles without lysis may be used for efficient and scalable AAV particle production. In a non-limiting example, AAV particles may be produced by culturing an AAV particle lacking a heparin binding site, thereby allowing the AAV particle to pass into the supernatant, in a cell culture, collecting supernatant from the culture; and isolating the AAV particle from the supernatant, as described in US Patent Application 20090275107, the contents of which are incorporated herein by reference in their entirety.

Clarification

Cell lysates comprising viral particles may be subjected to clarification. Clarification refers to initial steps taken in purification of viral particles from cell lysates. Clarification serves to prepare lysates for further purification by removing larger, insoluble debris. Clarification steps may include, but are not limited to centrifugation and filtration. During clarification, centrifugation may be carried out at low speeds to remove larger debris, only. Similarly, filtration may be carried out using filters with larger pore sizes so that only larger debris is removed. In some cases, tangential flow filtration may be used during clarification. Objectives of viral clarification include high throughput processing of cell lysates and to optimize ultimate viral recovery. Advantages of including a clarification step include scalability for processing of larger volumes of lysate. In some embodiments, clarification may be carried out according to any of the methods presented in U.S. Pat. Nos. 8,524,446, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498, 7,491,508, US Publication Nos. US2013/0045186, US2011/0263027, US2011/0151434, US2003/0138772, and International Publication Nos. WO2002012455, WO1996039530, WO1998010088, WO1999014354, WO1999015685, WO1999047691, WO2000055342, WO2000075353 and WO2001023597, the contents of each of which are herein incorporated by reference in their entirety.

Methods of cell lysate clarification by filtration are well understood in the art and may be carried out according to a variety of available methods including, but not limited to passive filtration and flow filtration. Filters used may comprise a variety of materials and pore sizes. For example, cell lysate filters may comprise pore sizes of from about 1 µM to about 5 µM, from about 0.5 µM to about 2 µM, from about 0.1 µM to about 1 µM from about 0.05 µM to about 0.05 µM and from about 0.001 µM to about 0.1 µM. Exemplary pore sizes for cell lysate filters may include, but are not limited to, 2.0, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.22, 0.21, 0.20, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, 0.001 and 0.001 µM. In one embodiment, clarification may comprise filtration through a filter with 2.0 µM pore size to remove large debris, followed by passage through a filter with 0.45 µM pore size to remove intact cells.

Filter materials may be composed of a variety of materials. Such materials may include, but are not limited to polymeric materials and metal materials (e.g. sintered metal and pored aluminum.) Exemplary materials may include, but are not limited to nylon, cellulose materials (e.g. cellulose acetate), polyvinylidene fluoride (PVDF), polyethersulfone, polyamide, polysulfone, polypropylene, and polyethylene terephthalate. In some cases, filters useful for clarification of cell lysates may include, but are not limited to ULTIPLEAT PROFILE™ filters (Pall Corporation, Port Washington, N.Y.), SUPOR™ membrane filters (Pall Corporation, Port Washington, N.Y.)

In some cases, flow filtration may be carried out to increase filtration speed and/or effectiveness. In some cases, flow filtration may comprise vacuum filtration. According to such methods, a vacuum is created on the side of the filter opposite that of cell lysate to be filtered. In some cases, cell lysates may be passed through filters by centrifugal forces. In some cases, a pump is used to force cell lysate through clarification filters. Flow rate of cell lysate through one or more filters may be modulated by adjusting one of channel size and/or fluid pressure.

According to some embodiments, cell lysates may be clarified by centrifugation. Centrifugation may be used to pellet insoluble particles in the lysate. During clarification, centrifugation strength [expressed in terms of gravitational units (g), which represents multiples of standard gravitational force] may be lower than in subsequent purification steps. In some cases, centrifugation may be carried out on cell lysates at from about 200 g to about 800 g, from about 500 g to about 1500 g, from about 1000 g to about 5000 g, from about 1200 g to about 10000 g or from about 8000 g to about 15000 g. In some embodiments, cell lysate centrifugation is carried out at 8000 g for 15 minutes. In some cases, density gradient centrifugation may be carried out in order to partition particulates in the cell lysate by sedimentation rate. Gradients used according to methods of the present disclosure may include, but are not limited to cesium chloride gradients and iodixanol step gradients.

Purification: Chromatography

In some cases, AAV particles may be purified from clarified cell lysates by one or more methods of chromatography. Chromatography refers to any number of methods known in the art for separating out one or more elements from a mixture. Such methods may include, but are not limited to ion exchange chromatography (e.g. cation exchange chromatography and anion exchange chromatography), immunoaffinity chromatography and size-exclusion chromatography. In some embodiments, methods of viral chromatography may include any of those taught in U.S. Pat. Nos. 5,756,283, 6,258,595, 6,261,551, 6,270,996, 6,281, 010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety.

In some embodiments, ion exchange chromatography may be used to isolate viral particles. Ion exchange chromatography is used to bind viral particles based on charge-charge interactions between capsid proteins and charged sites present on a stationary phase, typically a column through which viral preparations (e.g. clarified lysates) are passed. After application of viral preparations, bound viral particles may then be eluted by applying an elution solution to disrupt the charge-charge interactions. Elution solutions may be optimized by adjusting salt concentration and/or pH to enhance recovery of bound viral particles. Depending on the charge of viral capsids being isolated, cation or anion exchange chromatography methods may be selected. Methods of ion exchange chromatography may include, but are not limited to any of those taught in U.S. Pat. Nos. 7,419, 817, 6,143,548, 7,094,604, 6,593,123, 7,015,026 and 8,137, 948, the contents of each of which are herein incorporated by reference in their entirety.

In some embodiments, immunoaffinity chromatography may be used. Immunoaffinity chromatography is a form of chromatography that utilizes one or more immune compounds (e.g. antibodies or antibody-related structures) to retain viral particles. Immune compounds may bind specifically to one or more structures on viral particle surfaces, including, but not limited to one or more viral coat protein. In some cases, immune compounds may be specific for a particular viral variant. In some cases, immune compounds may bind to multiple viral variants. In some embodiments, immune compounds may include recombinant single-chain antibodies. Such recombinant single chain antibodies may include those described in Smith, R. H. et al., 2009. Mol. Ther. 17(11):1888-96, the contents of which are herein incorporated by reference in their entirety. Such immune compounds are capable of binding to several AAV capsid variants, including, but not limited to AAV1, AAV2, AAV6 and AAV8.

In some embodiments, size-exclusion chromatography (SEC) may be used. SEC may comprise the use of a gel to separate particles according to size. In viral particle purification, SEC filtration is sometimes referred to as "polishing." In some cases, SEC may be carried out to generate a final product that is near-homogenous. Such final products may in some cases be used in pre-clinical studies and/or clinical studies (Kotin, R. M. 2011. Human Molecular Genetics. 20(1):R2-R6, the contents of which are herein incorporated by reference in their entirety.) In some cases, SEC may be carried out according to any of the methods taught in U.S. Pat. Nos. 6,143,548, 7,015,026, 8,476,418, 6,410,300, 8,476,418, 7,419,817, 7,094,604, 6,593,123, and 8,137,948, the contents of each of which are herein incorporated by reference in their entirety.

In one embodiment, the compositions comprising at least one AAV particle may be isolated or purified using the methods described in U.S. Pat. No. 6,146,874, the contents of which are herein incorporated by reference in its entirety.

In one embodiment, the compositions comprising at least one AAV particle may be isolated or purified using the methods described in U.S. Pat. No. 6,660,514, the contents of which are herein incorporated by reference in its entirety.

In one embodiment, the compositions comprising at least one AAV particle may be isolated or purified using the methods described in U.S. Pat. No. 8,283,151, the contents of which are herein incorporated by reference in its entirety.

In one embodiment, the compositions comprising at least one AAV particle may be isolated or purified using the methods described in U.S. Pat. No. 8,524,446, the contents of which are herein incorporated by reference in its entirety.

II. Formulation and Delivery

Pharmaceutical Compositions and Formulation

Although the descriptions of pharmaceutical compositions, e.g., those modulatory polynucleotides (including the encoding plasmids or expression vectors, such as viruses, e.g., AAV) comprising a payload to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the viral vector carrying the payload or to the modulatory polynucleotide payload molecule delivered by a viral vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

The modulatory polynucleotides or viral vectors encoding them can be formulated using one or more excipients to: (1) increase stability; (2) increase cell transfection or transduction; (3) permit the sustained or delayed release; or (4) alter the biodistribution (e.g., target the viral vector to specific tissues or cell types).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between .5 and 50%, between 1-30%, between 5-80%, at least 80% (w/w) active ingredient.

In some embodiments, the formulations described herein may contain at least one payload molecule. As a non-limiting example, the formulations may contain 1, 2, 3, 4 or 5 modulatory polynucleotide payload molecules. In one embodiment the formulation may contain a modulatory polynucleotide payload construct targeting proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In one embodiment, the formulation contains at least three payload construct targeting proteins.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by the United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, modulatory polynucleotide formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of viral vectors carrying modulatory polynucleotide disclosed herein may include cations or anions. In one embodiment, the formulations include metal cations such as, but not limited to, Zn2+, Ca2+, Cu2+, Mg+ and combinations thereof. As a non-limiting example, formulations may include polymers and modulatory polynucleotides complexed with a metal cation (See e.g., U.S. Pat. Nos. 6,265,389 and 6,555,525, each of which is herein incorporated by reference in its entirety).

Delivery

In one embodiment, the viral vector comprising a modulatory polynucleotide may be administered or delivered using the methods for the delivery of AAV virions described in European Patent Application No. EP1857552, the contents of which are herein incorporated by reference in their entirety.

In one embodiment, the viral vector comprising a modulatory polynucleotide may be administered or delivered using the methods for delivering proteins using AAV vectors described in European Patent Application No. EP2678433, the contents of which are herein incorporated by reference in their entirety.

In one embodiment, the viral vector comprising a modulatory polynucleotide may be administered or delivered using the methods for delivering DNA molecules using AAV vectors described in U.S. Pat. No. 5,858,351, the contents of which are herein incorporated by reference in their entirety.

In one embodiment, the viral vector comprising a modulatory polynucleotide may be administered or delivered using the methods for delivering DNA to the bloodstream described in U.S. Pat. No. 6,211,163, the contents of which are herein incorporated by reference in their entirety.

In one embodiment, the viral vector comprising a modulatory polynucleotide may be administered or delivered using the methods for delivering AAV virions described in U.S. Pat. No. 6,325,998, the contents of which are herein incorporated by reference in their entirety.

In one embodiment, the viral vector comprising a modulatory polynucleotide may be administered or delivered using the methods for delivering DNA to muscle cells described in U.S. Pat. No. 6,335,011, the contents of which are herein incorporated by reference in their entirety.

In one embodiment, the viral vector comprising a modulatory polynucleotide may be administered or delivered using the methods for delivering DNA to muscle cells and tissues described in U.S. Pat. No. 6,610,290, the contents of which are herein incorporated by reference in their entirety.

In one embodiment, the viral vector comprising a modulatory polynucleotide may be administered or delivered using the methods for delivering DNA to muscle cells described in U.S. Pat. No. 7,704,492, the contents of which are herein incorporated by reference in their entirety.

In one embodiment, the viral vector comprising a modulatory polynucleotide may be administered or delivered using the methods for delivering a payload to skeletal muscles described in U.S. Pat. No. 7,112,321, the contents of which are herein incorporated by reference in their entirety.

In one embodiment, the viral vector may be administered or delivered using the methods for delivering a payload to the central nervous system described in U.S. Pat. No. 7,588,757, the contents of which are herein incorporated by reference in their entirety.

In one embodiment, the viral vector comprising a modulatory polynucleotide may be administered or delivered using the methods for delivering a payload described in U.S. Pat. No. 8,283,151, the contents of which are herein incorporated by reference in their entirety.

In one embodiment, the viral vector comprising a modulatory polynucleotide may be administered or delivered using the methods for delivering a payload for the treatment of Alzheimer disease described in U.S. Pat. No. 8,318,687, the contents of which are herein incorporated by reference in their entirety.

In one embodiment, the viral vector comprising a modulatory polynucleotide may be administered or delivered using the methods for delivering a payload described in International Patent Publication No. WO2012144446, the contents of which are herein incorporated by reference in their entirety.

In one embodiment, the viral vector comprising a modulatory polynucleotide may be administered or delivered using the methods for delivering a payload using a glutamic acid decarboxylase (GAD) delivery vector described in International Patent Publication No. WO2001089583, the contents of which are herein incorporated by reference in their entirety.

In one embodiment, the viral vector comprising a modulatory polynucleotide may be administered or delivered using the methods for delivering a payload described in International Patent Publication No. WO2001096587, the contents of which are herein incorporated by reference in their entirety.

In one embodiment, the viral vector comprising a modulatory polynucleotide may be administered or delivered using the methods for delivering a payload to muscle tissue described in International Patent Publication No. WO2002014487, the contents of which are herein incorporated by reference in their entirety.

In one embodiment, the viral vector comprising a modulatory polynucleotide may be administered or delivered using the methods for delivering a payload to neural cells described in International Patent Publication No. WO2012057363, the contents of which are herein incorporated by reference in their entirety.

The pharmaceutical compositions of viral vectors described herein may be characterized by one or more of bioavailability, therapeutic window and/or volume of distribution.

In one embodiment, the viral vectors comprising a modulatory polynucleotide may be formulated. As a non-limiting example the baricity and/or osmolality of the formulation may be optimized to ensure optimal drug distribution in the central nervous system or a region or component of the central nervous system.

In one embodiment, the viral vectors comprising a modulatory polynucleotide may be delivered to a subject via a single route administration.

In one embodiment, the viral vectors comprising a modulatory polynucleotide may be delivered to a subject via a multi-site route of administration. A subject may be administered the viral vectors comprising a modulatory polynucleotide at 2, 3, 4, 5 or more than 5 sites.

In one embodiment, a subject may be administered the viral vectors comprising a modulatory polynucleotide described herein using a bolus infusion.

In one embodiment, a subject may be administered the viral vectors comprising a modulatory polynucleotide described herein using sustained delivery over a period of minutes, hours or days. The infusion rate may be changed depending on the subject, distribution, formulation or another delivery parameter.

In one embodiment, the catheter may be located at more than one site in the spine for multi-site delivery. The viral vectors comprising a modulatory polynucleotide may be delivered in a continuous and/or bolus infusion. Each site of delivery may be a different dosing regimen or the same dosing regimen may be used for each site of delivery. As a non-limiting example, the sites of delivery may be in the cervical and the lumbar region. As another non-limiting example, the sites of delivery may be in the cervical region. As another non-limiting example, the sites of delivery may be in the lumbar region.

In one embodiment, a subject may be analyzed for spinal anatomy and pathology prior to delivery of the viral vectors comprising a modulatory polynucleotide described herein. As a non-limiting example, a subject with scoliosis may have a different dosing regimen and/or catheter location compared to a subject without scoliosis.

In one embodiment, the orientation of the spine subject during delivery of the viral vectors comprising a modulatory polynucleotide may be vertical to the ground.

In another embodiment, the orientation of the spine of the subject during delivery of the viral vectors comprising a modulatory polynucleotide may be horizontal to the ground.

In one embodiment, the spine of the subject may be at an angle as compared to the ground during the delivery of the viral vectors comprising a modulatory polynucleotide subject. The angle of the spine of the subject as compared to the ground may be at least 10, 20, 30, 40, 50, 60, 70, 80, 90, 100, 110, 120, 130, 140, 150 or 180 degrees.

In one embodiment, the delivery method and duration is chosen to provide broad transduction in the spinal cord. As a non-limiting example, intrathecal delivery is used to provide broad transduction along the rostral-caudal length of the spinal cord. As another non-limiting example, multi-site infusions provide a more uniform transduction along the rostral-caudal length of the spinal cord. As yet another non-limiting example, prolonged infusions provide a more uniform transduction along the rostral-caudal length of the spinal cord.

Introduction Into Cells

The modulatory polynucleotides of the invention can be introduced into host cells using any of a variety of approaches. Infection with a viral vector comprising the modulatory polynucleotide can be affected. Examples of suitable viral vectors include replication defective retroviral vectors, adenoviral vectors, adeno-associated vectors and lentiviral vectors.

According to the present invention, viral vectors for use in therapeutics and/or diagnostics comprise a virus that has been distilled or reduced to the minimum components necessary for transduction of a nucleic acid payload or cargo of interest.

In this manner, viral vectors are engineered as vehicles for specific delivery while lacking the deleterious replication and/or integration features found in wild-type virus.

As used herein, a "vector" is any molecule or moiety which transports, transduces or otherwise acts as a carrier of a heterologous molecule such as the modulatory polynucleotides of the invention. A "viral vector" is a vector which comprises one or more polynucleotide regions encoding or comprising payload molecules of interest, e.g., a transgene, a polynucleotide encoding a polypeptide or multi-polypeptide or a modulatory nucleic acid. Viral vectors of the present invention may be produced recombinantly and may be based on adeno-associated virus (AAV) parent or reference sequences. Serotypes which may be useful in the present invention include any of those arising from AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, AAV-DJ8, AAV-PHP.A and/or AAV-PHP.B.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

In one embodiment, the AAV vector used in the present invention is a scAAV.

In one embodiment, the modulatory polynucleotides may be introduced into cells from any relevant species, such as, but not limited to, human, dog, mouse, rat or monkey.

In one embodiment, the modulatory polynucleotides may be introduced into cells which are relevant to the disease to be treated. As a non-limiting example, the disease is ALS and the target cells are motor neurons and astrocytes.

In one embodiment, the modulatory polynucleotides may be introduced into cells which have a high level of endogenous expression of the target sequence.

In another embodiment, the modulatory polynucleotides may be introduced into cells which have a low level of endogenous expression of the target sequence.

In one embodiment, the cells may be those which have a high efficiency of AAV transduction.

In one embodiment, the cells which may be used for in vitro analysis of the modulatory polynucleotides include, but are not limited to, HEK293, HeLa, human primary astrocytes, human astrocyte cell line (U251MG), SH-SY5Y-neurons and human iPSC-derived motor neuron progenitors.

III. Administration and Dosing

Administration

The viral vectors comprising modulatory polynucleotides of the present invention may be administered by any route which results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), subpial (between the pia and the underlying tissue), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intrailieal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions may be administered in a way which allows them to cross the blood-brain barrier, vascular barrier, or other epithelial barrier. In one embodiment, a formulation for a route of administration may include at least one inactive ingredient.

Dosing

The present invention provides methods comprising administering viral vectors and their modulatory polynucleotide payload or complexes in accordance with the invention to a subject in need thereof. Viral vector pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific modulatory polynucleotide payload employed; the duration of the treatment; drugs used in combination or coincidental with the specific compound employed; and like factors well known in the medical arts.

In certain embodiments, viral vector pharmaceutical compositions in accordance with the present invention may be administered at modulatory polynucleotide dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect (see e.g., the range of unit doses described in International Publication No WO2013078199, herein incorporated by reference in its entirety). The desired modulatory polynucleotide dosage may be delivered more than once (e.g., more than one administration in a day). In certain embodiments, the desired modulatory polynucleotide dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any modulatory polynucleotide therapeutic administered in one dose/at one time/single route/single point of contact, i.e., single administration event. As used herein, a "total daily dose" is an amount given or prescribed in 24 hour period. It may be administered as a single unit dose. In one embodiment, the viral vectors comprising the modulatory polynucleotides of the present invention are administered to a subject in split doses. They may be formulated in buffer only or in a formulation described herein.

In one embodiment, delivery of the compositions in accordance with the present invention to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions in accordance with the present invention to cells may comprise a total concentration per subject between about $1\times10^6$ VG and about $1\times10^{16}$ VG. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{23}$, $6\times10^{13}$, $6.7\times10^{13}$, $7\times10^{13}$, $8\times10^{13}$, $9\times10^{13}$, $1\times10^{14}$, $2\times10^{10}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/subject.

In one embodiment, delivery of compositions in accordance with the present invention to cells may comprise a total concentration per subject between about $1\times10^6$ VG/kg and about $1\times10^{16}$ VG/kg. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{11}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{11}$, $8.2\times10^{12}$, $8.3\times10^{12}$, $8.4\times10^{12}$, $8.5\times10^{11}$, $8.6\times10^{11}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{11}$, $3\times10^{14}$, $4\times10^{15}$, $3\times10^{15}$, $4\times10^{15}$, $5\times10^{15}$, $6\times10^{15}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/kg.

In one embodiment, about $10^5$ to $10^6$ viral genome (unit) may be administered per dose.

In one embodiment, delivery of the compositions in accordance with the present invention to cells may comprise a total concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^{16}$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{th}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{11}$, $4.3\times10^{11}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{11}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10$, $8\times1^{14}$, $9\times10^{11}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL.

Bioavailability

Viral vectors comprising a modulatory polynucleotide of the present invention, when formulated into compositions with delivery/formulation agents or vehicles as described herein, may exhibit increased bioavailability as compared to compositions lacking delivery agents as described herein. As used herein, the term "bioavailability" refers to the systemic availability of a given amount of a particular agent administered to a subject. Bioavailability may be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound may be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in their entirety.

$C_{max}$ values are maximum concentrations of compounds achieved in serum or plasma of a subject following administration of compounds to the subject. $C_{max}$ values of particular compounds may be measured using methods known to those of ordinary skill in the art. As used herein, the phrases "increasing bioavailability" or "improving the pharmacokinetics," refer to actions that may increase the systemic availability of a viral vector of the present invention (as measured by AUC, $C_{max}$, or $C_{min}$) in a subject. In some embodiments, such actions may comprise co-administration with one or more delivery agents as described herein. In some embodiments, the bioavailability of viral vectors may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Therapeutic Window

Viral vectors comprising a modulatory polynucleotide of the present invention, when formulated with one or more delivery agents as described herein, may exhibit increases in the therapeutic window of compound and/or composition administration as compared to the therapeutic window of viral vectors administered without one or more delivery agents as described herein. As used herein, the term "therapeutic window" refers to the range of plasma concentrations, or the range of levels of therapeutically active substance at the site of action, with a high probability of eliciting a therapeutic effect. In some embodiments, therapeutic windows of viral vectors when administered in a formulation may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Volume of Distribution

Viral vectors comprising a modulatory polynucleotide of the present invention, when formulated with one or more delivery agents as described herein, may exhibit an improved volume of distribution ($V_{dist}$), e.g., reduced or targeted, relative to formulations lacking one or more delivery agents as described herein. $V_{dist}$ relates the amount of an agent in the body to the concentration of the same agent in the blood or plasma. As used herein, the term "volume of distribution" refers to the fluid volume that would be required to contain the total amount of an agent in the body at the same concentration as in the blood or plasma: $V_{dist}$ equals the amount of an agent in the body/concentration of the agent in blood or plasma. For example, for a 10 mg dose of a given agent and a plasma concentration of 10 mg/L, the volume of distribution would be 1 liter. The volume of distribution reflects the extent to which an agent is present in the extravascular tissue. Large volumes of distribution reflect the tendency of agents to bind to the tissue components as compared with plasma proteins. In clinical settings, $V_{dist}$ may be used to determine loading doses to achieve steady state concentrations. In some embodiments, volumes of distribution of viral vector compositions of the present invention when co-administered with one or more delivery agents as described herein may decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Combinations

The viral vectors comprising the modulatory polynucleotide may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

IV. Methods of Use

Reduce Expression of a Target Gene

In some embodiments, the present invention provides methods for inhibiting/silencing gene expression in a cell. Accordingly, the modulatory polynucleotides encoding siRNA duplexes or encoded dsRNA can be used to substantially inhibit gene expression in a cell, in particular in a neuron. In some aspects, the inhibition of gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing gene expression in a cell, in particular in a medium spiny neuron. In some aspects, the inhibition of gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing gene expression in a cell, in particular in a motor neuron. In some aspects, the inhibition of gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing gene expression in a cell, in particular in an astrocyte. In some aspects, the inhibition of gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95$^0$ 0, 55-100%, 60-70%, 60-80%, 60-90%, 60-95%, 60-100%, 70-80%, 70-90%, 70-95% , 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA may be used to reduce the expression of protein by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of protein expression may be reduced by 50-90%. As a non-limiting example, the expression of protein expression may be reduced by 30-70%. As a non-limiting example, the expression of protein expression may be reduced by 20-70%. As a non-limiting example, the expression of protein expression may be reduced by 15-30%.

In one embodiment, the modulatory polynucleotides encoding siRNA duplexes or encoded dsRNA may be used to reduce the expression of mRNA by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of mRNA expression may be reduced by 50-90%. As a non-limiting example, the expression of mRNA expression may be reduced by 30-70%. As a non-limiting example, the expression of mRNA expression may be reduced by 20-70%. As a non-limiting example, the expression of mRNA expression may be reduced by 15-30%.

In one embodiment, the siRNA duplexes or encoded dsRNA may be used to reduce the expression of protein and/or mRNA in at least one region of the CNS such as, but not limited to the midbrain. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100° A in at least one region of the CNS. As a non-limiting example, the expression of protein and mRNA in the striatum and/or cortex is reduced by 50-90%. As a non-limiting example, the expression of protein and mRNA in the striatum is reduced by 40-50%. As a non-limiting example, the expression of protein and mRNA in the striatum is reduced by 20-50%. As a non-limiting example, the expression of protein and mRNA in the striatum is reduced by 15-50%. As a non-limiting example, the expression of protein and mRNA in the cortex is reduced by 40-50%. As a non-limiting example, the expression of protein and mRNA in the cortex is reduced by 30-70%. As a non-limiting example, the expression of protein and mRNA in the cortex is reduced by 20-70%. As a non-limiting example, the expression of protein and mRNA in the cortex is reduced by 15-70%. As a non-limiting example, the expression of protein and mRNA in the striatum and/or cortex is reduced by 20-70%. As a non-limiting example, the expression of protein and mRNA in the striatum and/or cortex is reduced by 20-70%. As a non-limiting example, the expression of protein and mRNA in the striatum and/or cortex is reduced by 15-70%. As a non-limiting example, the expression of protein and mRNA in the striatum and/or cortex is reduced by 40-70%. As a non-limiting example, the expression of protein and mRNA in the striatum and/or cortex is reduced by 40-50%. As a non-limiting example, the expression of protein and mRNA in the striatum and/or cortex is reduced by 50-70%. As a non-limiting example, the expression of protein and mRNA in the striatum and/or cortex is reduced by 50-60%. As a non-limiting example, the expression of protein and mRNA in the striatum and/or cortex is reduced by 50%. As a non-limiting example, the expression of protein and mRNA in the striatum and/or cortex is reduced by 51%. As a non-limiting example, the expression of protein and mRNA in the striatum and/or cortex is reduced by 52%. As a non-limiting example, the expression of protein and mRNA in the striatum and/or cortex is reduced by 53%. As a non-limiting example, the expression of protein and mRNA in the striatum and/or cortex is reduced by 54%. As a non-limiting example, the expression of protein and mRNA in the striatum and/or cortex is reduced by 55%. As a non-limiting example, the expression of protein and mRNA in the striatum and/or cortex is reduced by 56%. As a non-limiting example, the expression of protein and mRNA in the striatum and/or cortex is reduced by 57%. As a non-limiting example, the expression of protein and mRNA in the striatum and/or cortex is reduced by 58%. As a non-limiting example, the expression of protein and mRNA in the striatum and/or cortex is reduced by 59%. As a non-limiting example, the expression of protein and mRNA in the striatum and/or cortex is reduced by 60%.

In one embodiment, the modulatory polynucleotides encoding siRNA duplexes or encoded dsRNA may be used to reduce the expression of protein and/or mRNA in at least one region of the CNS such as, but not limited to the forebrain. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of protein and mRNA in the putamen is reduced by 50-90%. As a non-limiting example, the expression of protein and mRNA in the striatum is reduced by 40-50%. As a non-limiting example, the expression of protein and mRNA in the cortex is reduced by 40-50%. As a non-limiting example, the expression of protein and mRNA in the cortex is reduced by 30-70%. As a non-limiting example, the expression of protein and mRNA in the cortex is reduced by 20-70%. As a non-limiting example, the expression of protein and mRNA in the cortex is reduced by 15-70%. As a non-limiting example, the expression of protein and mRNA in the striatum and/or cortex is reduced by 20-70%. As a non-limiting example, the expression of protein and mRNA in the striatum and/or cortex is reduced by 15-70%. As a non-limiting example, the expression of protein and mRNA in the striatum and/or cortex is reduced by 40-70%. As a non-limiting example, the expression of protein and mRNA in the striatum and/or cortex is reduced by 40-50%. As a non-limiting example, the expression of protein and mRNA in the striatum and/or cortex is reduced by 50-70%. As a non-limiting example, the expression of protein and mRNA in the striatum and/or cortex is reduced by 50-60%. As a non-limiting example, the expression of protein and mRNA in the striatum and/or cortex is reduced by 50%. As a non-limiting example, the expression of protein and mRNA in the striatum and/or cortex is reduced by 51%. As a non-limiting example, the expression of protein and mRNA in the striatum and/or cortex is reduced by 52%. As a non-limiting example, the expression of protein and mRNA in the striatum and/or cortex is reduced by 53%. As a non-limiting example, the expression of protein and mRNA in the striatum and/or cortex is reduced by 54%. As a non-limiting example, the expression of protein and mRNA in the striatum and/or cortex is reduced by 55%. As a non-limiting example, the expression of protein and mRNA in the striatum and/or cortex is reduced by 56%. As a non-limiting example, the expression of protein and mRNA in the striatum and/or cortex is reduced by 57%. As a non-limiting example, the expression of protein and mRNA in the striatum and/or cortex is reduced by 58%. As a non-limiting example, the expression of protein and mRNA in the striatum and/or cortex is reduced by 59%. As a non-limiting example, the expression of protein and mRNA in the striatum and/or cortex is reduced by 60%. As a non-limiting example, the expression of protein and mRNA in the striatum and/or cortex is reduced by 61%. As a non-limiting example, the expression of protein and mRNA in the striatum and/or cortex is reduced by 62%. As a non-limiting example, the expression of protein and mRNA in the striatum and/or cortex is reduced by 63%. As a non-limiting example, the expression of protein and mRNA in the striatum and/or cortex is reduced by 64%. As a non-limiting example, the expression of protein and mRNA in the striatum and/or cortex is reduced by 65%. As a non-limiting example, the expression of protein and mRNA in the striatum and/or cortex is reduced by 66%. As a non-limiting example, the expression of protein and mRNA in the striatum and/or cortex is reduced by 67%. As a non-limiting example, the expression of protein and mRNA in the striatum and/or cortex is reduced by 68%. As a non-limiting example, the expression of protein and mRNA in the striatum and/or cortex is reduced by 69%. As a non-limiting example, the expression of protein and mRNA in the striatum and/or cortex is reduced by 70%.

In one embodiment, the modulatory polynucleotides encoding siRNA duplexes or encoded dsRNA may be used to reduce the expression of protein and/or mRNA in the putamen. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of protein and mRNA in the putamen is reduced by 40-70%. As a non-limiting example, the expression of protein and mRNA in the putamen is reduced by 40-50%. As a non-limiting example, the expression of protein and mRNA in the putamen is reduced by 50-70%. As a non-limiting example, the expression of protein and mRNA in the putamen is reduced by 50-60%. As a non-limiting example, the expression of protein and mRNA in the putamen is reduced by 50%. As a non-limiting example, the expression of protein and mRNA in the putamen is reduced by 51%. As a non-limiting example, the expression of protein and mRNA in the putamen is reduced by 52%. As a non-limiting example, the expression of protein and mRNA in the putamen is reduced by 53%. As a non-limiting example, the expression of protein and mRNA in the putamen is reduced by 54%. As a non-limiting example, the expression of protein and mRNA in the putamen is reduced by 55%. As a non-limiting example, the expression of protein and mRNA in the putamen is reduced by 56%. As a non-limiting example, the expression of protein and mRNA in the putamen is reduced by 57%. As a non-limiting example, the expression of protein and mRNA in the putamen is reduced by 58%. As a non-limiting example, the expression of protein and mRNA in the putamen is reduced by 59%. As a non-limiting example, the expression of protein and mRNA in the putamen is reduced by 60%. As a non-limiting example, the expression of protein and mRNA in the putamen is reduced by 61%. As a non-limiting example, the expression of protein and mRNA in the putamen is reduced by 62%. As a non-limiting example, the expression of protein and mRNA in the putamen is reduced by 63%. As a non-limiting example, the expression of protein and mRNA in the putamen is reduced by 64%. As a non-limiting example, the expression of protein and mRNA in the putamen is reduced by 65%. As a non-limiting example, the expression of protein and mRNA in the putamen is reduced by 66%. As a non-limiting example, the expression of protein and mRNA in the putamen is reduced by 67%. As a non-limiting example, the expression of protein and mRNA in the putamen is reduced by 68%. As a non-limiting example, the expression of protein and mRNA in the putamen is reduced by 69%. As a non-limiting example, the expression of protein and mRNA in the putamen is reduced by 70%.

In one embodiment, the modulatory polynucleotides encoding siRNA duplexes or encoded dsRNA may be used to reduce the expression of protein and/or mRNA in the cortex. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of protein and mRNA in the cortex is reduced by 40-50%. As a non-limiting example, the expression of protein and mRNA in the cortex is reduced by 30-70%. As a non-limiting example, the expression of protein and mRNA in the cortex is reduced by at least 30%. As a non-limiting example, the expression of protein and mRNA in the cortex is reduced by 40-70%. As a non-limiting example, the expression of protein and mRNA in the cortex is reduced by 40-50%. As a non-limiting example, the expression of protein and mRNA in the cortex is reduced by 50-70%. As a non-limiting example, the expression of protein and mRNA in the cortex is reduced by 50-60%. As a non-limiting example, the expression of protein and mRNA in the cortex is reduced by 50%. As a non-limiting example, the expression of protein and mRNA in the cortex is reduced by 51%. As a non-limiting example, the expression of protein and mRNA in the cortex is reduced by 52%. As a non-limiting example, the expression of protein and mRNA in the cortex is reduced by 53%. As a non-limiting example, the expression of protein and mRNA in the cortex is reduced by 54%. As a non-limiting example, the expression of protein and mRNA in the cortex is reduced by 55%. As a non-limiting example, the expression of protein and mRNA in the cortex is reduced by 56%. As a non-limiting example, the expression of protein and mRNA in the cortex is reduced by 57%. As a non-limiting example, the expression of protein and mRNA in the cortex is reduced by 58%. As a non-limiting example, the expression of protein and mRNA in the cortex is reduced by 59%. As a non-limiting example, the expression of protein and mRNA in the cortex is reduced by 60%. As a non-limiting example, the expression of protein and mRNA in the cortex is reduced by 61%. As a non-limiting example, the expression of protein and mRNA in the cortex is reduced by 62%. As a non-limiting example, the expression of protein and mRNA in the cortex is reduced by 63%. As a non-limiting example, the expression of protein and mRNA in the cortex is reduced by 64%. As a non-limiting example, the expression of protein and mRNA in the cortex is reduced by 65%. As a non-limiting example, the expression of protein and mRNA in the cortex is reduced by 66%. As a non-limiting example, the expression of protein and mRNA in the cortex is reduced by 67%. As a non-limiting example, the expression of protein and mRNA in the cortex is reduced by 68%. As a non-limiting example, the expression of protein and mRNA in the cortex is reduced by 69%. As a non-limiting example, the expression of protein and mRNA in the cortex is reduced by 70%.

In one embodiment, the modulatory polynucleotides encoding siRNA duplexes or encoded dsRNA may be used to reduce the expression of protein and/or mRNA in the motor cortex. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of protein and mRNA in the motor cortex is reduced by 40-50%. As a non-limiting example, the expression of protein and mRNA in the motor cortex is reduced by 30-70%. As a non-limiting example, the expression of protein and mRNA in the motor cortex is reduced by 20-70%. As a non-limiting example, the expression of protein and mRNA in the motor cortex is reduced by 15-70%. As a non-limiting example, the expression of protein and mRNA in the motor cortex is reduced by at least 30%. As a non-limiting example, the expression of protein and mRNA in the motor cortex is reduced by 40-70%. As a non-limiting example, the expression of protein and mRNA in the motor cortex is reduced by 50-70%. As a non-limiting example, the expression of protein and mRNA in the motor cortex is reduced by 50-60%. As a non-limiting example, the expression of protein and mRNA in the motor cortex is reduced by 50%. As a non-limiting example, the expression of protein and mRNA in the motor cortex is reduced by 51%. As a non-limiting example, the expression of protein and mRNA in the motor cortex is reduced by 52%. As a non-limiting example, the expression of protein and mRNA in the motor cortex is reduced by 53%. As a non-limiting example, the expression of protein and mRNA in the motor cortex is reduced by 54%. As a non-limiting example, the expression of protein and mRNA in the motor cortex is reduced by 55%. As a non-limiting example, the expression of protein and mRNA in the motor cortex is reduced by 56%. As a non-limiting example, the expression of protein and mRNA in the motor cortex is reduced by 57%. As a non-limiting example, the expression of protein and mRNA in the motor cortex is reduced by 58%. As a non-limiting example, the expression of protein and mRNA in the motor cortex is reduced by 59%. As a non-limiting example, the expression of protein and mRNA in the motor cortex is reduced by 60%. As a non-limiting example, the expression of protein and mRNA in the motor cortex is reduced by 61%. As a non-limiting example, the expression of protein and mRNA in the motor cortex is reduced by 62%. As a non-limiting example, the expression of protein and mRNA in the motor cortex is reduced by 63%. As a non-limiting example, the expression of protein and mRNA in the motor cortex is reduced by 64%. As a non-limiting example, the expression of protein and mRNA in the motor cortex is reduced by 65%. As a non-limiting example, the expression of protein and mRNA in the motor cortex is reduced by 66%. As a non-limiting example, the expression of protein and mRNA in the motor cortex is reduced by 67%. As a non-limiting example, the expression of protein and mRNA in the motor cortex is reduced by 68%. As a non-limiting example, the expression of protein and mRNA in the motor cortex is reduced by 69%. As a non-limiting example, the expression of protein and mRNA in the motor cortex is reduced by 70%.

In one embodiment, the modulatory polynucleotides encoding siRNA duplexes or encoded dsRNA may be used to reduce the expression of protein and/or mRNA in the somatosensory cortex. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of protein and mRNA in the somatosensory cortex is reduced by 40-50%. As a non-limiting example, the expression of protein and mRNA in the somatosensory cortex is reduced by 30-70%. As a non-limiting example, the expression of protein and mRNA in the somatosensory cortex is reduced by 20-70%. As a non-limiting example, the expression of protein and mRNA in the somatosensory cortex is reduced by 15-70%. As a non-limiting example, the expression of protein and mRNA in the somatosensory cortex is reduced by at least 30%. As a non-limiting example, the expression of protein and mRNA in the somatosensory cortex is reduced by 40-70%. As a non-limiting example, the expression of protein and mRNA in the somatosensory cortex is reduced by 50-70%. As a non-limiting example, the expression of protein and mRNA in the somatosensory cortex is reduced by 50-60%. As a non-limiting example, the expression of protein and mRNA in the somatosensory cortex is reduced by 50%. As a non-limiting example, the expression of protein and mRNA in the somatosensory cortex is reduced by 51%. As a non-limiting example, the expression of protein and mRNA in the somatosensory cortex is reduced by 52%. As a non-limiting example, the expression of protein and mRNA in the somatosensory cortex is reduced by 53%. As a non-limiting example, the expression of protein and mRNA in the somatosensory cortex is reduced by 54%. As a non-limiting example, the expression of protein and mRNA in the somatosensory cortex is reduced by 55%. As a non-limiting example, the expression of protein and mRNA in the somatosensory cortex is reduced by 56%. As a non-limiting example, the expression of protein and mRNA in the somatosensory cortex is reduced by 57%. As a non-limiting example, the expression of protein and mRNA in the somatosensory cortex is reduced by 58%. As a non-limiting example, the expression of protein and mRNA in the somatosensory cortex is reduced by 59%. As a non-limiting example, the expression of protein and mRNA in the somatosensory cortex is reduced by 60%. As a non-limiting example, the expression of protein and mRNA in the somatosensory cortex is reduced by 61%. As a non-limiting example, the expression of protein and mRNA in the somatosensory cortex is reduced by 62%. As a non-limiting example, the expression of protein and mRNA in the somatosensory cortex is reduced by 63%. As a non-limiting example, the expression of protein and mRNA in the somatosensory cortex is reduced by 64%. As a non-limiting example, the expression of protein and mRNA in the somatosensory cortex is reduced by 65%. As a non-limiting example, the expression of protein and mRNA in the somatosensory cortex is reduced by 66%. As a non-limiting example, the expression of protein and mRNA in the somatosensory cortex is reduced by 67%. As a non-limiting example, the expression of protein and mRNA in the somatosensory cortex is reduced by 68%. As a non-limiting example, the expression of protein and mRNA in the somatosensory cortex is reduced by 69%. As a non-limiting example, the expression of protein and mRNA in the somatosensory cortex is reduced by 70%.

In one embodiment, the modulatory polynucleotides encoding siRNA duplexes or encoded dsRNA may be used to reduce the expression of protein and/or mRNA in the temporal cortex. The expression of protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of protein and mRNA in the temporal cortex is reduced by 40-50%. As a non-limiting example, the expression of protein and mRNA in the temporal cortex is reduced by 30-70%. As a non-limiting example, the expression of protein and mRNA in the temporal cortex is reduced by 20-70%. As a non-limiting example, the expression of protein and mRNA in the temporal cortex is reduced by 15-70%. As a non-limiting example, the expression of protein and mRNA in the temporal cortex is reduced by at least 30%. As a non-limiting example, the expression of protein and mRNA in the temporal cortex is reduced by 40-70%. As a non-limiting example, the expression of protein and mRNA in the temporal cortex is reduced by 50-70%. As a non-limiting example, the expression of protein and mRNA in the temporal cortex is reduced by 50-60%. As a non-limiting example, the expression of protein and mRNA in the temporal cortex is reduced by 50%. As a non-limiting example, the expression of protein and mRNA in the temporal cortex is reduced by 51%. As a non-limiting example, the expression of protein and mRNA in the temporal cortex is reduced by 52%. As a non-limiting example, the expression of protein and mRNA in the temporal cortex is reduced by 53%. As a non-limiting example, the expression of protein and mRNA in the temporal cortex is reduced by 54%. As a non-limiting example, the expression of protein and mRNA in the temporal cortex is reduced by 55%. As a non-limiting example, the expression of protein and mRNA in the temporal cortex is reduced by 56%. As a non-limiting example, the expression of protein and mRNA in the temporal cortex is reduced by 57%. As a non-limiting example, the expression of protein and mRNA in the temporal cortex is reduced by 58%. As a non-limiting example, the expression of protein and mRNA in the temporal cortex is reduced by 59%. As a non-limiting example, the expression of protein and mRNA in the temporal cortex is reduced by 60%. As a non-limiting example, the expression of protein and mRNA in the temporal cortex is reduced by 61%. As a non-limiting example, the expression of protein and mRNA in the temporal cortex is reduced by 62%. As a non-limiting example, the expression of protein and mRNA in the temporal cortex is reduced by 63%. As a non-limiting example, the expression of protein and mRNA in the temporal cortex is reduced by 64%. As a non-limiting example, the expression of protein and mRNA in the temporal cortex is reduced by 65%. As a non-limiting example, the expression of protein and mRNA in the temporal cortex is reduced by 66%. As a non-limiting example, the expression of protein and mRNA in the temporal cortex is reduced by 67%. As a non-limiting example, the expression of protein and mRNA in the temporal cortex is reduced by 68%. As a non-limiting example, the expression of protein and mRNA in the temporal cortex is reduced by 69%. As a non-limiting example, the expression of protein and mRNA in the temporal cortex is reduced by 70%.

In some embodiments, the present invention provides methods for treating, or ameliorating a disease and/or disorder of the central nervous system by inhibiting the expression of a gene and/or protein in a subject in need of treatment, the method comprising administering to the subject a pharmaceutically effective amount of at least one modulatory polynucleotides encoding siRNA duplex or a nucleic acid encoding an siRNA duplex targeting the gene, delivering the modulatory polynucleotides encoding siRNA duplex (or encoded duplex) into targeted cells, inhibiting gene expression and protein production, and ameliorating symptoms of the disease and/or disorder of the central nervous system in the subject.

V. Kits and Devices

Kits

The invention provides a variety of kits for conveniently and/or effectively carrying out methods of the present invention. Typically, kits will comprise sufficient amounts and/or numbers of components to allow a user to perform multiple treatments of a subject(s) and/or to perform multiple experiments.

Any of the vectors, constructs, modulatory polynucleotides, polynucleotides or polypeptides of the present invention may be comprised in a kit. In some embodiments, kits may further include reagents and/or instructions for creating and/or synthesizing compounds and/or compositions of the present invention. In some embodiments, kits may also include one or more buffers. In some embodiments, kits of the invention may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably aliquotted. Where there are more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present invention may also typically include means for containing compounds and/or compositions of the present invention, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, compounds and/or compositions of the present invention may be combined with, coated onto or embedded in a device. Devices may include, but are not limited to, dental implants, stents, bone replacements, artificial joints, valves, pacemakers and/or other implantable therapeutic device.

The present invention provides for devices which may incorporate viral vectors that encode one or more modulatory polynucleotide payload molecules. These devices contain in a stable formulation the viral vectors which may be immediately delivered to a subject in need thereof, such as a human patient.

Devices for administration may be employed to deliver the viral vectors comprising a modulatory polynucleotide of the present invention according to single, multi- or split-dosing regimens taught herein.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

The modulatory polynucleotides of the present invention may be used in the treatment, prophylaxis or amelioration of any disease or disorder characterized by aberrant or undesired target expression.

VI. Definitions

At various places in the present specification, substituents of compounds of the present disclosure are disclosed in groups or in ranges. It is specifically intended that the present disclosure include each and every individual sub-combination of the members of such groups and ranges.

About: As used herein, the term "about" means +/−10% of the recited value.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a modulatory polynucleotide of the present invention may be considered biologically active if even a portion of the polynucleotides is biologically active or mimics an activity considered biologically relevant.

Induced pluripotent stem cells: As used herein, "induced pluripotent stem cells" are cells that may be induced to form any of several distinct cell types.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a modulatory polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least one modulatory polynucleotide and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form modulatory polynucleotide multimers (e.g., through linkage of two or more modulatory polynucleotides molecules) or modulatory polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof., Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the invention. Molecules may be modified in many ways including chemically, structurally, and functionally.

Naturally occurring: As used herein, "naturally occurring" means existing in nature without artificial aid.

Neutralizing antibody: As used herein, a "neutralizing antibody" refers to an antibody which binds to its antigen and defends a cell from an antigen or infectious agent by neutralizing or abolishing any biological activity it has.

Non-human vertebrate: As used herein, a "non human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein the alkyl is optionally substituted"). It is not intended to mean that the feature "X" (e.g. alkyl)per se is optional.

Peptide: As used herein, "peptide" is less than or equal to 50 amino acids long, e.g., about 5, 10, 15, 20, 25, 30, 35, 40, 45, or 50 amino acids long.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrates, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-V C H, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A. C. S. Symposium Series, and in *Bioreversible Carriers in Drug Design*, ed. Edward B. Roche, American Pharmaceutical Association and Pergamon Press, 1987, both of which are hereby incorporated by reference in their entirety. In some embodiments, the pri-miRs of the invention may be prodrugs of the pre-miRs. Likewise either pri- or pre-miRs may be prodrugs of the artificial miRs which are processed from them.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Stereoisomer: As used herein, the term "stereoisomer" refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hour period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

VII. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

VIII. Examples

Example 1

Design of Modulatory Polynucleotides (Artificial Pri- or Pre-microRNAs)

Artificial pri- or pre-microRNAs are designed to contain shRNA or stem loop structures encoding an artificial miR (or artificial siRNA or mature miRNA) having at least one strand that can at least partially hybridize with a target nucleic acid, e.g., RNA or DNA and one or more of the following features (a) UG motif at the base of basal stem, (b) a UGUG motif at the 5' end of the miRNA loop, (c) Uridine at the 5' end of guide strand, (d) a loop structure derived from a canonical microRNA such as miR-22, (e) a CNNC at the 3' flanking sequence, (f) flanking regions from a canonical microRNA such as let-7b, (g) one or more wobble base-pairs, bulges and mismatches in the stem after guide and passenger stands, and/or (h) one or more wobble base-pairs, bulges and mismatches between the passenger and guide strand.

Once designed, the sequence is engineered or synthesized or inserted in a plasmid or vector and administered to a cell or organism. Suitable plasmids or vectors are any which transfect or transduce the target cell.

Adeno-associated viral vectors (AAV), viral particles or entire viruses may be used.

Administration results in the processing of the modulatory polynucleotide to generate the artificial microRNA which alters expression levels of the target nucleic acid.

Effective knockdown of a target may be determined by methods in the art and will show little if any off-target effects.

Effective passenger-guide strand duplexes of the modulatory polynucleotides, e.g., pri- or pre-microRNAs demonstrate greater than 8-10-fold guide to passenger strand ratio when processing is measured.

Example 2

Passenger-Guide Strand Optimization

In order to achieve target knockdown or modulation of target expression which is specific and potent, the passenger and guide strands that will form the duplex stem of the stem-loop structure of the pri- or pre-microRNA of the invention may be optimized separately, for example as siRNA (small interfering RNAs).

siRNAs are designed against a target nucleic acid of choice as canonical siRNAs having a 19 base pair central duplex with a dinucleotide overhang on the 3' end of the strands of the duplex and where the antisense strand (guide strand) has perfect complementarity to the target nucleic acid over the 19 nucleotide region.

Alternatively, siRNAs are designed whereby the sense strand (passenger strand) comprises less than 19 nucleotide identity to the target nucleic acid.

Modifications to the sense-antisense (passenger-guide) strand duplex base pairing is made to introduce wobbles, bulges or mismatches. Insertions or deletions or mismatches may be incorporated at the 5' or 3' terminus of the sense strand (passenter strand) and these insertions or deletions may or may not be mirrored on the antisense strand (guide strand).

The resulting siRNA are tested by standard methods known in the art for target knockdown and other relevant physiologic and pharmacokinetic properties and for degree of off-target effects.

siRNA exhibiting sufficient target knockdown with few off target effects are then engineered, either with or without further modifications, as the passenger and guide strands of the pri- or pre-microRNAs of the invention.

Example 3

Pri and Pre-microRNAs Targeting HTT

The passenger-guide strand duplexes found to be efficacious are engineered into expression vectors and transfected into cells of the central nervous system or neuronal cell lines or immortalized cell lines of other origins. Even though overhang utilized in the siRNA knockdown study is a canonical dTdT for siRNA, the overhang in the synthetic pri- or pre-miR may comprise any dinucleotide overhang.

The cells used may be primary cells or derived from induced pluripotent stem cells (iPS cells).

The knockdown of the target is then measured and deep sequencing performed to determine the exact passenger and guide strand processed from each pri- or pre-microRNA administered in the expression vector.

A guide to passenger strand ratio is calculated to determine the efficiency of assembly, e.g., assembly into RNA Induced Silencing Complex (RISC).

The 5' end of guide and passenger strands are sequenced to determine the cleavage site and to determine the 5' end processing precision. It is expected that processing precision will be higher than 85 percent.

HeLa cells are co-transfected in a parallel study to analyze in vitro knockdown of the target. In parallel, a cell-base luciferase reporter assay is established; a luciferase construct containing guide strand target site is used to assess on-target effect and a construct with passenger strand target site is used to determine off-target (passenger strand) effects.

Deep sequencing is again performed.

Example 4

Pri-miRNA Constructs in AAV-miRNA Vectors

Passenger-guide strand duplexes of the designed siRNA are engineered into AAV-miRNA expression vectors. The construct from ITR to ITR, recited 5' to 3', comprises a mutant or wild-type ITR, a promoter (either a CMV, a H1, a U6 or the CBA promoter (which includes a CMVie enhancer, a CB promoter and an SV40 or a human beta-Globin intron)), the pri-miRNA construct for the target, a rabbit globin or human growth hormone polyA and wildtype ITR. In vitro and in vivo studies are performed to test the efficacy of the AAV-miRNA expression vectors.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11193129B2). An electronic copy of the "Sequence Listing" will also be available from the USPTO upon request and payment of the fee set forth in 37 CFR 1.19(b)(3).

We claim:

1. A modulatory polynucleotide for targeting the expression of an Htt gene, comprising:
(a) a stem and a loop which form a stem-loop structure, the sequence of said stem-loop structure comprising, from 5' to 3':
(i) a 5' stem arm comprising a passenger strand and a 5' spacer sequence;
(ii) a loop region, which comprises a nucleotide sequence which is at least 85% identical to SEQ ID NO: 16;
(iii) a 3' stem arm comprising a guide strand and a 3' spacer sequence, wherein the guide strand is at least 60% complementary to a target RNA, and wherein the target RNA is expressed from the Htt gene;
(b) a first flanking region located 5' to said passenger strand, said first flanking region comprising the 5' spacer sequence and a 5' flanking sequence, wherein the first flanking region comprises a nucleotide sequence which is at least 90% identical to SEQ ID NO: 5; and
(c) a second flanking region located 3' to said guide strand, said second flanking region comprising the 3' spacer sequence and a 3' flanking sequence, wherein said second flanking region comprises a nucleotide sequence which is at least 90% identical to SEQ ID NO: 21.

2. The modulatory polynucleotide of claim 1, wherein the loop region comprises SEQ ID NO: 16.

3. The modulatory polynucleotide of claim 1, wherein the first flanking region comprises SEQ ID NO: 5.

4. The modulatory polynucleotide of claim 1, wherein the second flanking region comprises SEQ ID NO: 21.

5. The modulatory polynucleotide of claim 1, wherein the loop region comprises SEQ ID NO: 16, wherein the first flanking region comprises SEQ ID NO: 5, and wherein the second flanking region comprises SEQ ID NO: 21.

6. The modulatory polynucleotide of claim 5, wherein the guide strand comprises a microRNA seed sequence comprising positions 2-7, 2-8 or 2-9 of the guide strand.

7. The modulatory polynucleotide of claim 5, wherein the guide strand is 20-22 nucleotides in length.

8. The modulatory polynucleotide of claim 7, wherein the passenger strand is between 15-30 nucleotides in length; wherein the 5' spacer sequence is between 8-20 nucleotides in length; wherein the guide strand is between 15-30 nucleotides in length; and wherein the 3' spacer sequence is between 8-20 nucleotides in length.

9. An adeno-associated virus (AAV) vector genome encoding the modulatory polynucleotide of claim 8.

10. An AAV particle comprising the AAV vector genome of claim 9 and an AAV1 capsid.

11. A modulatory polynucleotide for targeting the expression of an Htt gene, comprising:
(a) a stem and a loop which form a stem-loop structure, the sequence of said stem-loop structure comprising, from 5' to 3':
(i) a 5' stem arm comprising a guide strand and a 5' spacer sequence, wherein the guide strand is at least 60% complementary to a target RNA, and wherein the target RNA is expressed from an Htt gene;
(ii) a loop region which comprises a nucleotide sequence which is at least 85% identical to SEQ ID NO: 16;
(iii) a 3' stem arm comprising a passenger strand and a 3' spacer sequence;
(b) a first flanking region located 5' to said guide strand, said first flanking region comprising the 5' spacer sequence and a 5' flanking sequence, wherein the first flanking region comprises a nucleotide sequence which is at least 90% identical to SEQ ID NO: 5; and
(c) a second flanking region located 3' to said passenger strand, said second flanking region comprising the 3' spacer sequence and a 3' flanking sequence, wherein said second flanking region comprises a nucleotide sequence which is at least 90% identical to SEQ ID NO: 21.

12. The modulatory polynucleotide of claim 11, wherein the loop region comprises SEQ ID NO: 16.

13. The modulatory polynucleotide of claim 11, wherein the first flanking region comprises SEQ ID NO: 5.

14. The modulatory polynucleotide of claim 11, wherein the second flanking region comprises SEQ ID NO: 21.

15. The modulatory polynucleotide of claim 11, wherein the loop region comprises SEQ ID NO: 16, wherein the first flanking region comprises SEQ ID NO: 5, and wherein the second flanking region comprises SEQ ID NO: 21.

16. The modulatory polynucleotide of claim 15, wherein the guide strand comprises a microRNA seed sequence comprising positions 2-7, 2-8 or 2-9 of the guide strand.

17. The modulatory polynucleotide of claim 15, wherein the guide strand is 20-22 nucleotides in length.

18. The modulatory polynucleotide of claim 17, wherein the passenger strand is between 15-30 nucleotides in length; wherein the 5' spacer sequence is between 8-20 nucleotides in length; wherein the guide strand is between 15-30 nucleotides in length; and wherein the 3' spacer sequence is between 8-20 nucleotides in length.

19. An adeno-associated virus (AAV) vector genome encoding the modulatory polynucleotide of claim 18.

20. An AAV particle comprising the AAV vector genome of claim 19 and an AAV1 capsid.

* * * * *